(12) United States Patent
Yancy et al.

(10) Patent No.: US 9,840,737 B2
(45) Date of Patent: Dec. 12, 2017

(54) METHODS AND SYSTEMS FOR SEQUENTIAL DETERMINATION OF GENETIC MUTATIONS AND/OR VARIANTS

(75) Inventors: Jacquline Yancy, Laurel, MD (US); Lingxia Jiang, Boyds, MD (US); Stephanie Buszczak, Rockville, MD (US); Renee Howell, Rockville, MD (US); Deborah Boles, Cary, NC (US)

(73) Assignee: Canon U.S. Life Sciences, Inc., Rockville, MD (US)

( * ) Notice: Subject to any disclaimer, the term of this patent is extended or adjusted under 35 U.S.C. 154(b) by 0 days.

(21) Appl. No.: 13/152,260

(22) Filed: Jun. 2, 2011

(65) Prior Publication Data

US 2012/0088236 A1    Apr. 12, 2012

Related U.S. Application Data

(60) Provisional application No. 61/350,893, filed on Jun. 2, 2010.

(51) Int. Cl.
*C12Q 1/68* (2006.01)

(52) U.S. Cl.
CPC .......... *C12Q 1/6883* (2013.01); *C12Q 1/6827* (2013.01); *C12Q 1/686* (2013.01); *C12Q 2600/156* (2013.01)

(58) Field of Classification Search
None
See application file for complete search history.

(56) References Cited

U.S. PATENT DOCUMENTS

2003/0082582 A1*  5/2003  Gatti ................................ 435/6
2007/0026421 A1*  2/2007  Sundberg et al. ................ 435/6

OTHER PUBLICATIONS

Zhou et al. Clinical Chemistry. 2005. 10: 1770-1777.*
Dobrowolski et al. Human Mutation. 2005. 25: 306-313.*
Audrezet et al. Journal of Molecular Diagnostics. 2008. 10(5): 424-434.*
Montgomery et al. Clinical Chemistry. 2007. 53(11). Data Supplemental.*
Liew et al. Clinical Chemistry. 2004. 50(7): 1156-1164.*
Tsui et al. Cold Spring Harb Perspect Med. 2013. 3:a009472.*
Montgomery et al. Scanning the cystic fibrosis transmembrane conductance regulator gene using high-resolution DNA melting analysis. Clin. Chem. Nov. 2007, vol. 53, No. 11, pp. 1891-1898; abstract; p. 1892, para 6; p. 1892, para 9-p. 1893, para 1; p. 1893, para; Fig. 3.
Greer et al. Comparison of glass etching to xurography prototyping of microfluidic channels for DNA melting analysis. J. Micromech. Microeng. Oct. 27, 2007 (Oct. 27, 2007), vol. 17, pp. 2407-2413; abstract.
Chou et al. A comparison of high-resolution melting analysis with denaturing high-performance liquid chromatography for mutation scanning: cystic fibrosis transmembrane conductance regulator gene as a model. Am. J. Clin. Pathol. Sep. 2005, vol. 124, No. 3, pp. 330-338.

* cited by examiner

*Primary Examiner* — Joseph G Dauner
(74) *Attorney, Agent, or Firm* — Canon U.S.A., Inc. IP Division

(57) ABSTRACT

The present invention relates to methods and systems for genome scanning using high resolution melting analysis for identifying mutations and/or variants in genes of interest.

14 Claims, 56 Drawing Sheets
(54 of 56 Drawing Sheet(s) Filed in Color)

| ACOG Mandated CF Mutations |
|---|
| delF508 |
| G542X |
| G551D |
| W1282X |
| 3849+10kbC>T |
| N1303K |
| 621+1G>T |
| 1717-1G>A |
| R553X |
| G85E |
| 3120+1G>A |
| delI507 |
| R1162X |
| 711+1G>T |
| R334W |
| R117H |
| 2789+5G>A |
| 1898+1G>A |
| 3659delC |
| 2184delA |
| A455E |
| R347P |
| R560T |
| Total: 23 |

FIG. 1

| Primer Pair | Aberrant amplification |
|---|---|
| 1F2/R2 | no |
| 2F1/R1 | small kink |
| 3F1/R1 | no |
| 3F2/R2 | kink |
| 4F1/R1 | small kink |
| 4F2/R2c | small kink |
| 5F/Rb | small kink |
| 6aF1/R1 | no |
| 6bF/R | small kink |
| 7F1/R1 | no |
| 7F2b/R2b | no |
| 8Fd/R | no |
| 9F/R | no |
| 10F1/R1 | no |
| 10F2/R2 | no |
| 10F3/R3 | small kink |
| 11F1/R1 | no |
| 11F2/R2 | no |
| 12Fb/R | kink |
| 13F1/R1 | no |
| 13F2/R2 | small kink |
| 13F3/R3 | small kink |
| 13F4/R4 | no |
| 13F5/R5 | no |
| 13F6/R6 | no |
| 14aF1/R1 | no |
| 14aF2/R2 | no |
| 14bF/R | no |
| 15F1/R1 | no |
| 15F2/R2 | no |
| 16F/R | kink |
| 17aF1/R1 | no |
| 17aF2/R2 | where? |
| 17bF1b/R1 | no amplification |
| 17bF2/R2 | Small kink |
| 18F/Rb | kink |
| 19F1/R1 | no |
| 19F2/R2 | no |
| 20F1/R1 | no |
| 20F2/R2 | kink |
| 21F/R | kink |
| 22F/R | no |
| 23F/R | no |
| 24F2/R2 | no |

FIG. 3

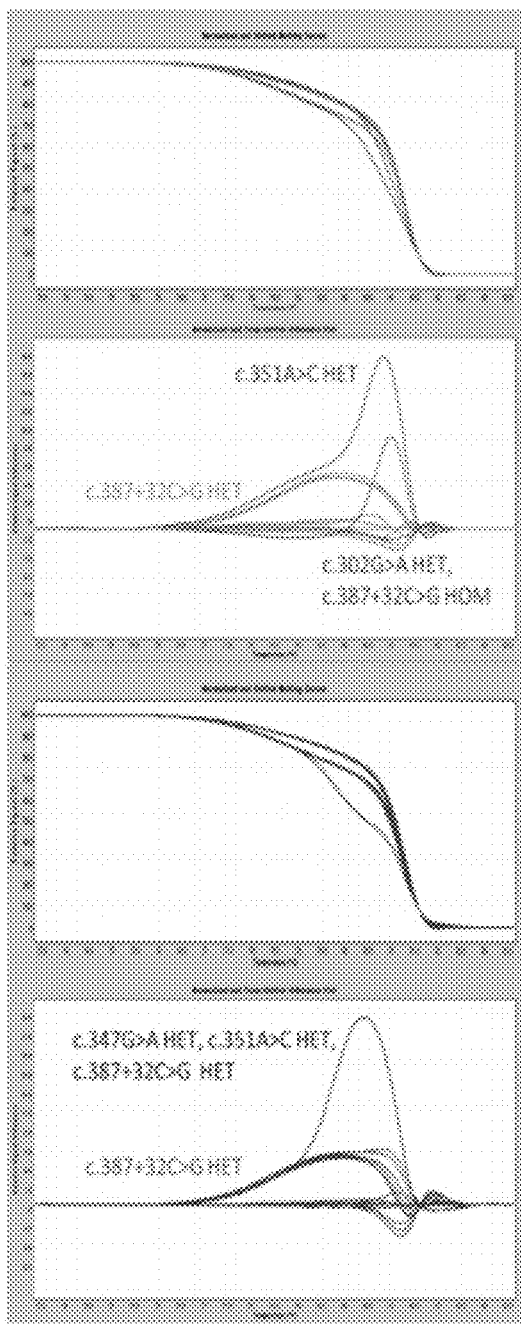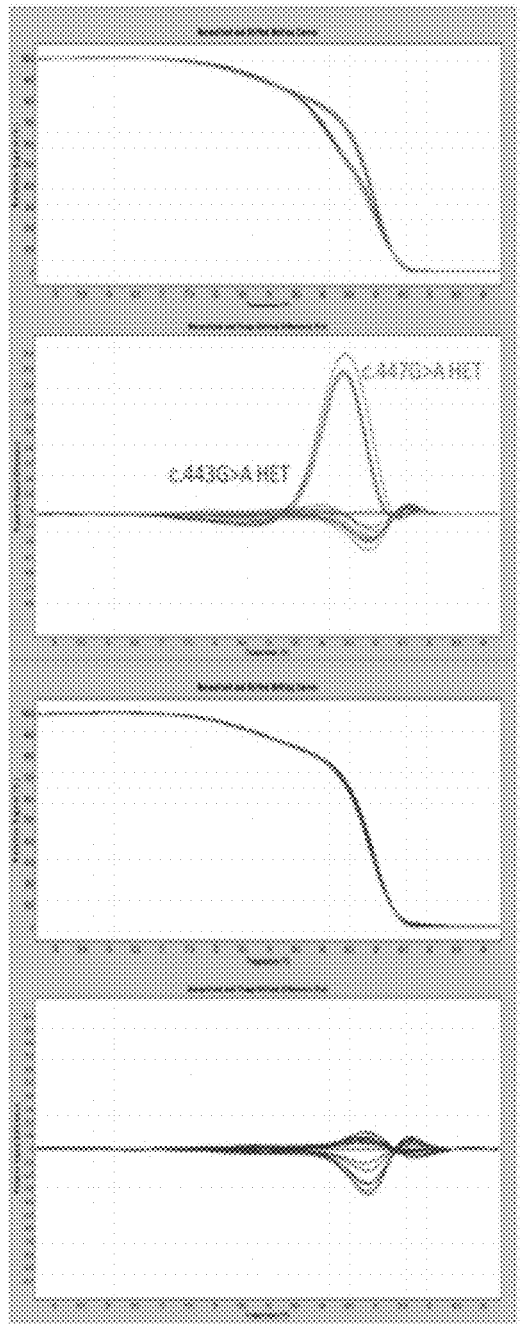
FIG 7C

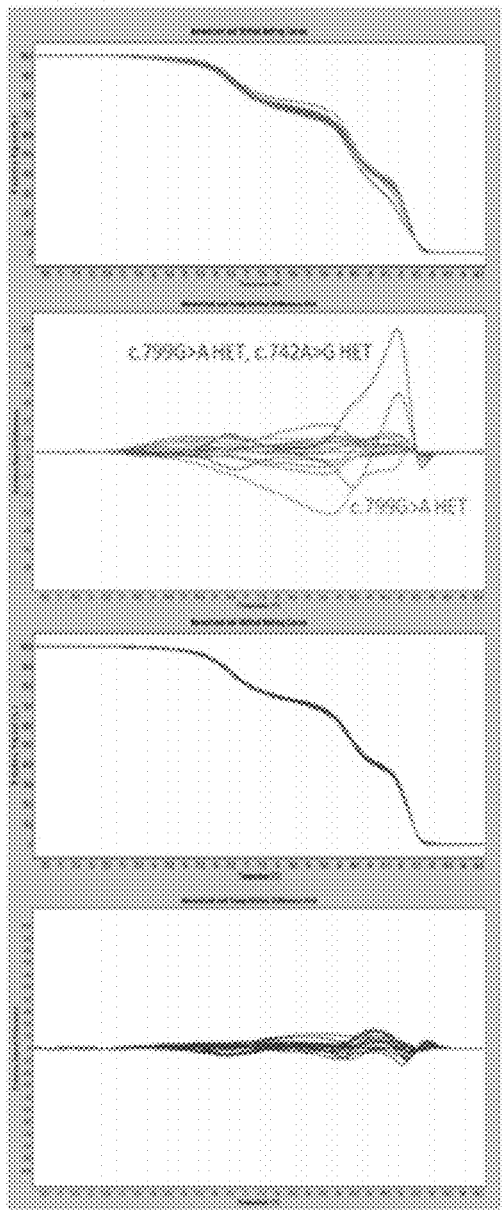
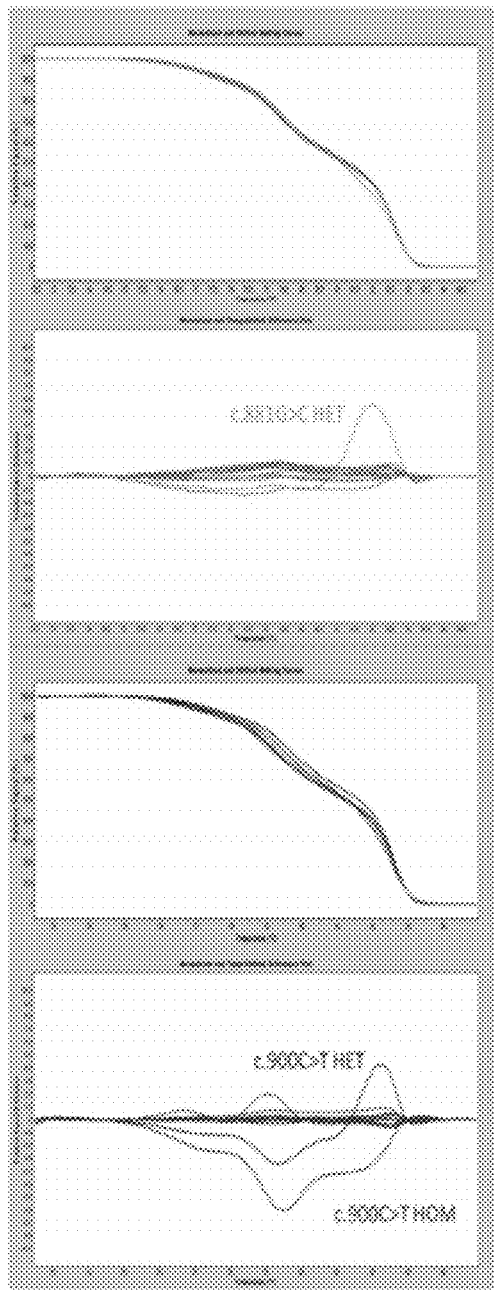
FIG 7E

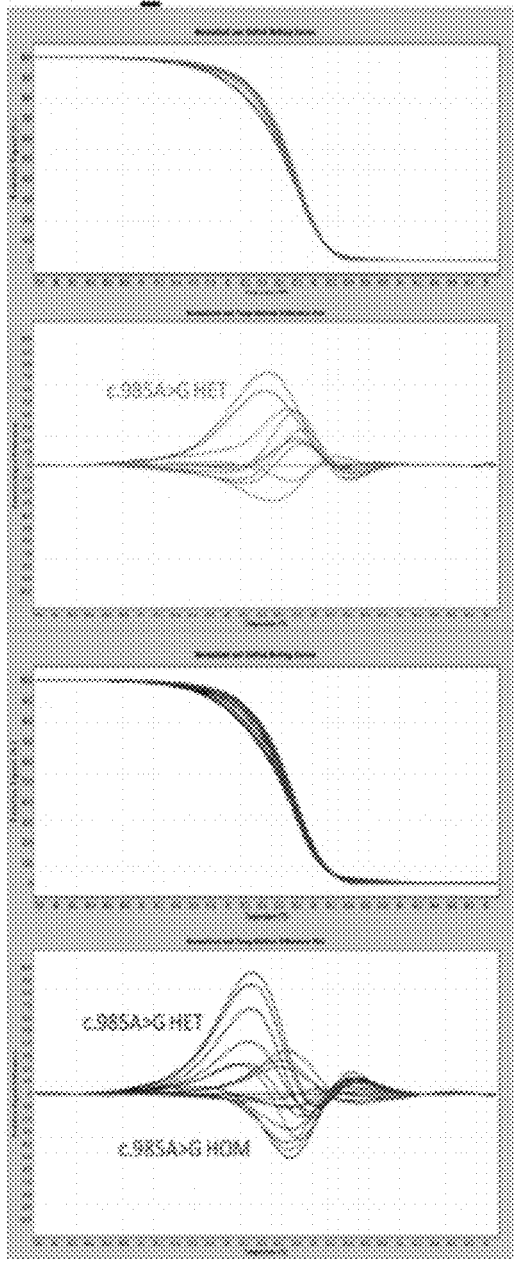
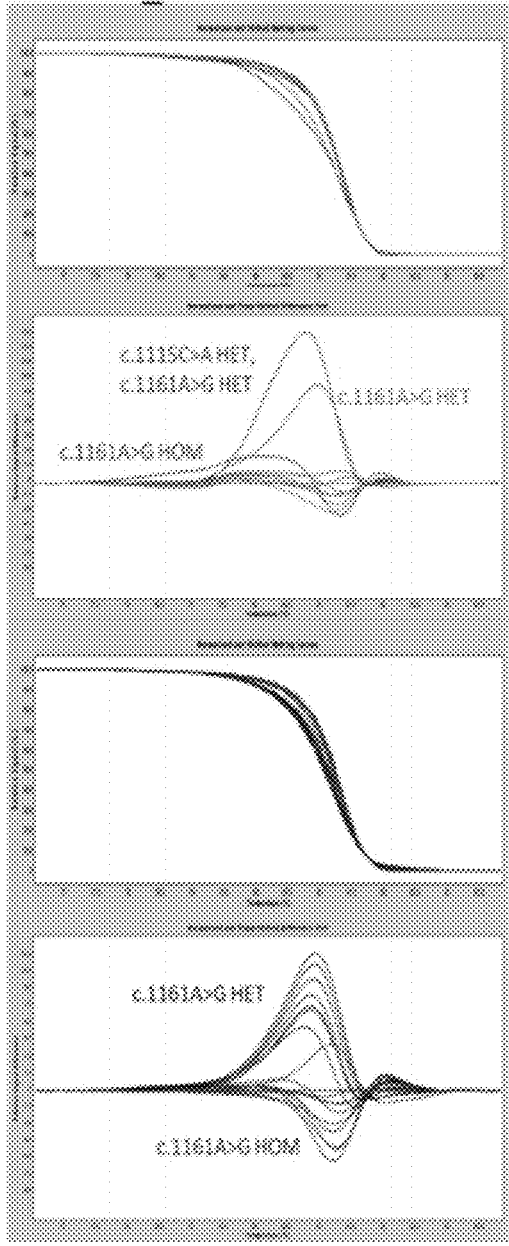
FIG 7F

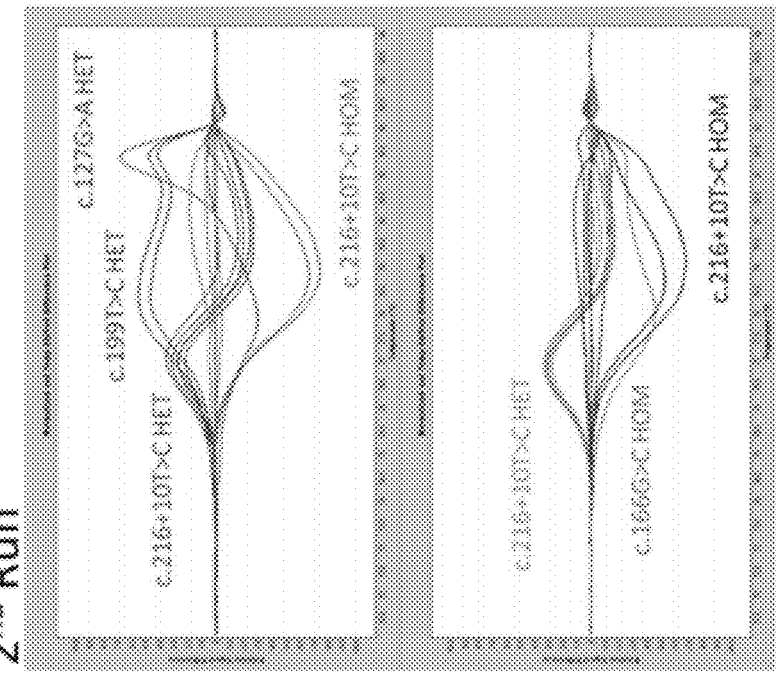
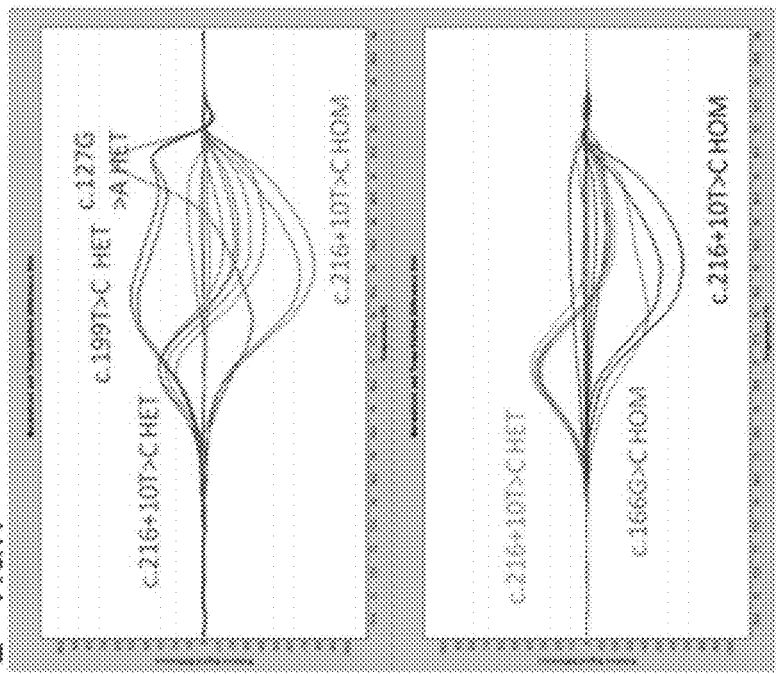
FIG 8A

Exon 9
1st Run
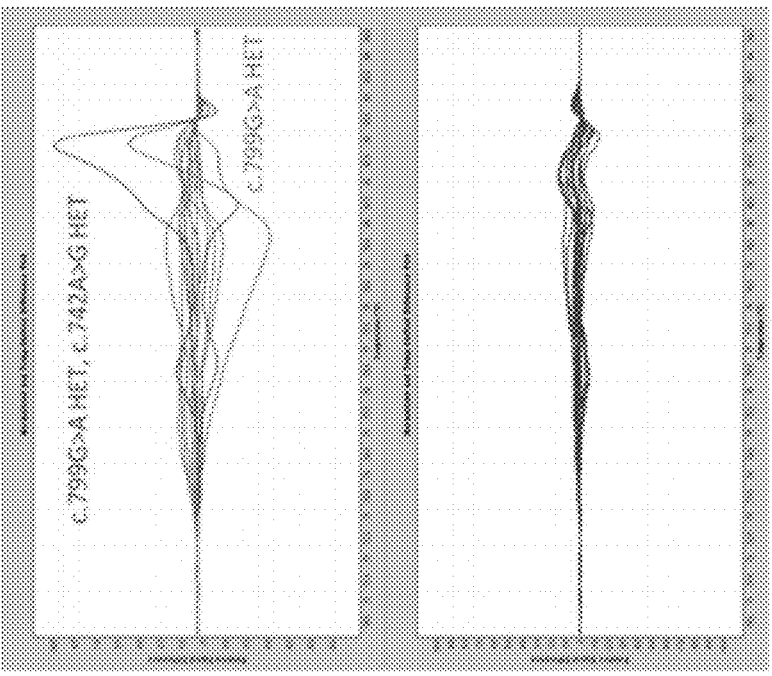
2nd Run
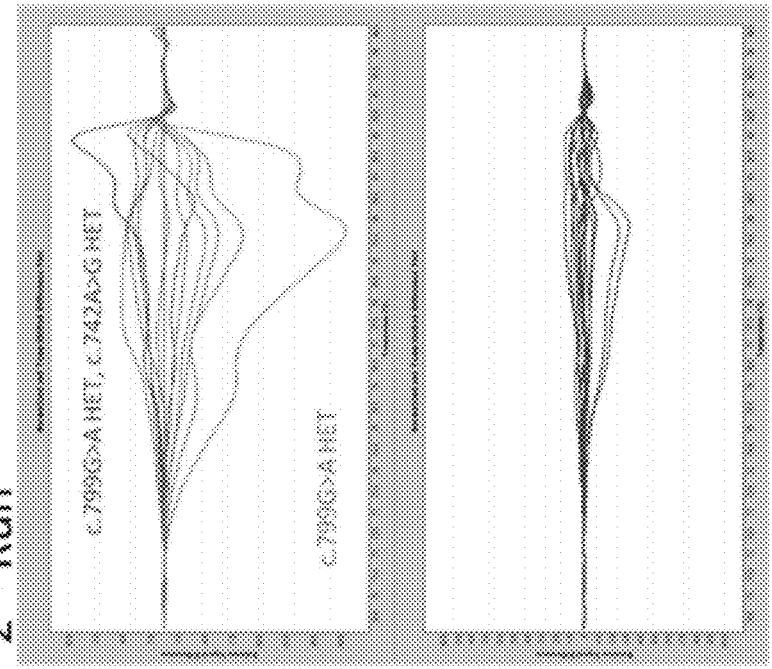
FIG. 8B

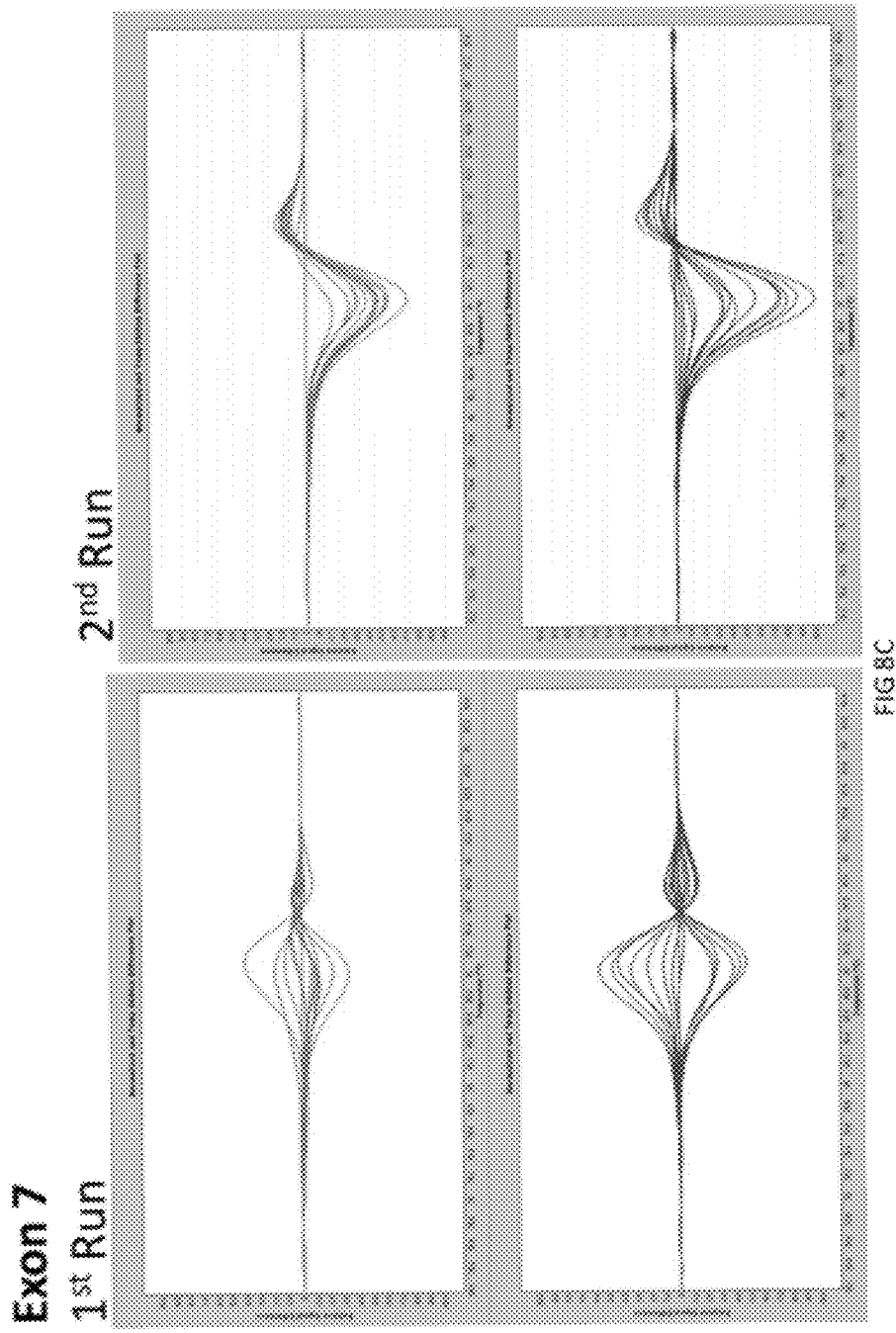

SEQUENCE LISTING

<160> NUMBER OF SEQ ID NOS: 136

<210> SEQ ID NO 1

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gacccgtgta ttattgtccg ag                                                  22

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tgctccgaca ccacaatacc                                                     20

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cagtagtctc ttatctgatt aatgtttaac ttatcaaatt                               40

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
aaagcttcat atgtataagt ttaaagtcaa aagatagaac                               40

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccttgttatc cagttttaac ttttctaaat aattttc                                  37

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cagatagttt gattacataa tcttgtaaaa aatgt                                    35

<210> SEQ ID NO 7
<211> LENGTH: 42
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cattttttac aagattatgt aatcaaacta tctggatttc aa                           42

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gagttccaca attttctta ctcatatgca ttccag                                   36

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
atagtttacc tttatttcta ttgtgatgta ctacatatt                               39

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttcaggagta actatctcat taacaagagc                                         30

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gcatctctga atttacatat ccaat                                              25

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aagtgtgaaa taaagcggca                                                    20

<210> SEQ ID NO 13
<211> LENGTH: 27
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 13
catttaattt catttctctt gttttta     27

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
agaaaaaata tacaaagatg ttttga     26

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
gagcaatcac catgtgttat     20

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 16 aatgtttta ttaaaggaaa gttaagtaat tt     32

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
tgatccctgt tttaggtaat tgc     23

<210> SEQ ID NO 18
<211> LENGTH: 26
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
gagaaacaca ctgaacatac aatttt     26

<210> SEQ ID NO 19
<211> LENGTH: 24
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 19
atagacactt aggcagatat tgtg                                          24

<210> SEQ ID NO 20
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aaattgatta gtttgtggtt taaaaatcat                                    30

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
acttttaagt tttctcaata aatatccttt aat                                33

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tatctccagc aaatgccttt                                               20

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtcgaaatac ctattatgct tct                                           23

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atattctctc tccttgcaaa c                                             21

<210> SEQ ID NO 25
<211> LENGTH: 30
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 25
aaagatattt aacctacact tatattttc                                          30

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
acagtggctt gtgttct                                                       17

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gaaatcatcc cagtggct                                                      18

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
acctacttca ccagttttat ca                                                 22

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atgataaaac tggtgaagta ggta                                               24

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aaagattttt ccctctttaa aatgt                                              25

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 31
ctggctgaaa tggcaatg                                                 18

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctctggtaac tcattctagc                                               20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ggcaatggat ttaatacaga                                               20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gcatccctca ttagtttttc                                               20

<210> SEQ ID NO 35
<211> LENGTH: 38
<212> TYPE: DNA
<213> ORGANISM: Homo sapiens

<400> SEQUENCE: 35
ccgctagagc aaatttgggg ccggaccagg cagcactc                           38

<210> SEQ ID NO 36
<211> LENGTH: 30
<212> TYPE: DNA
<213> ORGANISM: Homo sapiens

<400> SEQUENCE: 36
aagagcaaaa ggaagggtg gtgtgcggag                                     30

<210> SEQ ID NO 37
<211> LENGTH: 203
<212> TYPE: DNA
<213> ORGANISM: Homo sapiens

<400> SEQUENCE: 37
aattggaagc aaatgacatc acagcaggtc agagaaaaag ggttgagcgg caggcaccca    60
gagtagtagg tctttggcat taggagcttg agcccagacg gccctagcag ggaccccagc   120
gcccgagaga ccatgcagag gtcgcctctg gaaaaggcca gcgttgtctc caaacttttt   180
ttcaggtgag aaggtggcca acc 203

<210> SEQ ID NO 38
<211> LENGTH: 17
<212> TYPE: PRT
<213> ORGANISM: Homo sapiens

<400> SEQUENCE: 38

Met Gln Arg Ser Pro Leu Glu Lys Ala Ser Val Val Ser Lys Leu Phe
1               5                   10                  15

Phe

<210> SEQ ID NO 39
<211> LENGTH: 37
<212> TYPE: DNA
<213> ORGANISM: Homo sapiens

<400> SEQUENCE: 39
agacacgtgc ccacgaaaga ggagggcgtg tgtatgg 37

<210> SEQ ID NO 40
<211> LENGTH: 30
<212> TYPE: DNA
<213> ORGANISM: Homo sapiens

<400> SEQUENCE: 40
acagtgtcaa aatgtttgca tttggcatag 30

<210> SEQ ID NO 41
<211> LENGTH: 220
<212> TYPE: DNA
<213> ORGANISM: Homo sapiens

<400> SEQUENCE: 41
gagaccaaat caagtgaata tctgttcctc ctctctttat tttagctgga ccagaccaat 60
tttgaggaaa ggatacagac agcgcctgga attgtcagac atataccaaa tcccttctgt 120
tgattctgct gacaatctat ctgaaaaatt ggaaaggtat gttcatgtac attgtttagt 180
tgaagagaga aattcatatt attaattatt tagagaagag 220

<210> SEQ ID NO 42
<211> LENGTH: 36
<212> TYPE: PRT
<213> ORGANISM: Homo sapiens

<400> SEQUENCE: 42

Trp Thr Arg Pro Ile Leu Arg Lys Gly Tyr Arg Gln Arg Leu Glu Leu
1               5                   10                  15

Ser Asp Ile Tyr Gln Ile Pro Ser Val Asp Ser Ala Asp Asn Leu Ser
            20                  25                  30

Glu Lys Leu Glu
            35

<210> SEQ ID NO 43
<211> LENGTH: 30
<212> TYPE: DNA
<213> ORGANISM: Homo sapiens

<400> SEQUENCE: 43
aagtatggtg gctaatgcct gtaatcccaa 30

```
<210> SEQ ID NO 44
<211> LENGTH: 270
<212> TYPE: DNA
<213> ORGANISM: Homo sapiens

<400> SEQUENCE: 44
ccttggatat acttgtgtga atcaaactat gttaagggaa ataggacaac taaaatattt      60
gcacatgcaa cttattggtc cactttttta ttcttttgca gagaatggga tagagagctg     120
gcttcaaaga aaaatcctaa actcattaat gcccttcggc gatgtttttt ctggagattt     180
atgttctatg gaatcttttt atatttaggg gtaaggatct catttgtaca ttcattatgt     240
atcacataac tatattcatt tttgtgatta                                      270

<210> SEQ ID NO 45
<211> LENGTH: 36
<212> TYPE: PRT
<213> ORGANISM: Homo sapiens

<400> SEQUENCE: 45

Glu Trp Asp Arg Glu Leu Ala Ser Lys Lys Asn Pro Lys Leu Ile Asn
 1               5                  10                  15

Ala Leu Arg Arg Cys Phe Phe Trp Arg Phe Met Phe Tyr Gly Ile Phe
            20                  25                  30

Leu Tyr Leu Gly
        35

<210> SEQ ID NO 46
<211> LENGTH: 60
<212> TYPE: DNA
<213> ORGANISM: Homo sapiens

<400> SEQUENCE: 46
ggtatgaccc tctatataaa ctcatttttaa gtctcctcta aagatgaaaa gtcttgtgtt     60

<210> SEQ ID NO 47
<211> LENGTH: 26
<212> TYPE: DNA
<213> ORGANISM: Homo sapiens

<400> SEQUENCE: 47
gttgaaattc tcagggtatt ttatga                                          26

<210> SEQ ID NO 48
<211> LENGTH: 296
<212> TYPE: DNA
<213> ORGANISM: Homo sapiens

<400> SEQUENCE: 48
aatttctctg ttttccccct tttgtaggaa gtcaccaaag cagtacagcc tctcttactg      60
ggaagaatca tagcttccta tgacccggat aacaaggagg aacgctctat cgcgatttat     120
ctaggcatag gcttatgcct tctctttatt gtgaggacac tgctcctaca cccagccatt     180
tttggccttc atcacattgg aatgcagatg agaatagcta tgtttagttt gatttataag     240
aaggtaatac ttcccttgcac aggccccatg gcacatatat tctgtatcgt acatgt       296

<210> SEQ ID NO 49
<211> LENGTH: 72
<212> TYPE: PRT
<213> ORGANISM: Homo sapiens

<400> SEQUENCE: 49
```

```
Glu Val Thr Lys Ala Val Gln Pro Leu Leu Leu Gly Arg Ile Ile Ala
1               5                   10                  15

Ser Tyr Asp Pro Asp Asn Lys Glu Glu Arg Ser Ile Ala Ile Tyr Leu
                20                  25                  30

Gly Ile Gly Leu Cys Leu Leu Phe Ile Val Arg Thr Leu Leu Leu His
            35                  40                  45

Pro Ala Ile Phe Gly Leu His His Ile Gly Met Gln Met Arg Ile Ala
        50                  55                  60

Met Phe Ser Leu Ile Tyr Lys Lys
65                  70
```

<210> SEQ ID NO 50
<211> LENGTH: 30
<212> TYPE: DNA
<213> ORGANISM: Homo sapiens

<400> SEQUENCE: 50
atttatgaac ctgagaagat agtaagctag                              30

<210> SEQ ID NO 51
<211> LENGTH: 43
<212> TYPE: DNA
<213> ORGANISM: Homo sapiens

<400> SEQUENCE: 51
agaatataat tttcattacc tttacttaat aatgaatgca taa               43

<210> SEQ ID NO 52
<211> LENGTH: 18
<212> TYPE: DNA
<213> ORGANISM: Homo sapiens

<400> SEQUENCE: 52
atttgtattt gtttgttg                                           18

<210> SEQ ID NO 53
<211> LENGTH: 177
<212> TYPE: DNA
<213> ORGANISM: Homo sapiens

<400> SEQUENCE: 53
aaattatcta actttccatt tttcttttag actttaaagc tgtcaagccg tgttctagat    60
aaaataagta ttggacaact tgttagtctc ctttccaaca acctgaacaa atttgatgaa   120
gtatgtacct attgatttaa tcttttaggc actattgtta taaattatac aactgga      177

<210> SEQ ID NO 54
<211> LENGTH: 30
<212> TYPE: PRT
<213> ORGANISM: Homo sapiens

<400> SEQUENCE: 54

```
Thr Leu Lys Leu Ser Ser Arg Val Leu Asp Lys Ile Ser Ile Gly Gln
1               5                   10                  15

Leu Val Ser Leu Leu Ser Asn Asn Leu Asn Lys Phe Asp Glu
                20                  25                  30
```

<210> SEQ ID NO 55
<211> LENGTH: 30
<212> TYPE: DNA
<213> ORGANISM: Homo sapiens

<400> SEQUENCE: 55
ttgatcatat aagctccttt tacttgcttt                                           30

<210> SEQ ID NO 56
<211> LENGTH: 21
<212> TYPE: DNA
<213> ORGANISM: Homo sapiens

<400> SEQUENCE: 56
acacctgttt ttgctgtgct t                                                    21

<210> SEQ ID NO 57
<211> LENGTH: 233
<212> TYPE: DNA
<213> ORGANISM: Homo sapiens

<400> SEQUENCE: 57
gcttttattt tccagggact tgcattggca catttcgtgt ggatcgctcc tttgcaagtg          60
gcactcctca tggggctaat ctgggagttg ttacaggcgt ctgccttctg tggacttggt         120
ttcctgatag tccttgccct ttttcaggct gggctaggga gaatgatgat gaagtacagg         180
tagcaaccta ttttcataac ttgaaagttt taaaaattat gttttcaaaa agc                233

<210> SEQ ID NO 58
<211> LENGTH: 54
<212> TYPE: PRT
<213> ORGANISM: Homo sapiens

<400> SEQUENCE: 58

Gly Leu Ala Leu Ala His Phe Val Trp Ile Ala Pro Leu Gln Val Ala
1               5                   10                  15

Leu Leu Met Gly Leu Ile Trp Glu Leu Leu Gln Ala Ser Ala Phe Cys
            20                  25                  30

Gly Leu Gly Phe Leu Ile Val Leu Ala Leu Phe Gln Ala Gly Leu Gly
        35                  40                  45

Arg Met Met Met Lys Tyr
    50

<210> SEQ ID NO 59
<211> LENGTH: 216
<212> TYPE: DNA
<213> ORGANISM: Homo sapiens

<400> SEQUENCE: 59
taatttgact tgtttttact attagattga ttgattgatt gattgattga tttacagaga          60
tcagagagct gggaagatca gtgaaagact tgtgattacc tcagaaatga ttgaaaatat         120
ccaatctgtt aaggcatact gctgggaaga agcaatggaa aaaatgattg aaaacttaag         180
acagtaagtt gttccaataa tttcaatatt gttagt                                   216

<210> SEQ ID NO 60
<211> LENGTH: 41
<212> TYPE: PRT
<213> ORGANISM: Homo sapiens

<400> SEQUENCE: 60

Asp Gln Arg Ala Gly Lys Ile Ser Glu Arg Leu Val Ile Thr Ser Glu
1               5                   10                  15

Met Ile Glu Asn Ile Gln Ser Val Lys Ala Tyr Cys Trp Glu Glu Ala

```
                    20                  25                  30
Met Glu Lys Met Ile Glu Asn Leu Arg
         35                  40
```

<210> SEQ ID NO 61
<211> LENGTH: 30
<212> TYPE: DNA
<213> ORGANISM: Homo sapiens

<400> SEQUENCE: 61
ccattccaag atccctgata tttgaaaaat                                30

<210> SEQ ID NO 62
<211> LENGTH: 349
<212> TYPE: DNA
<213> ORGANISM: Homo sapiens

<400> SEQUENCE: 62
taacatcctg aattttattg ttattgtttt ttatagaaca gaactgaaac tgactcggaa      60
ggcagcctat gtgagatact tcaatagctc agccttcttc ttctcagggt tctttgtggt     120 gttttatct gtgcttccct atgcactaat caaaggaatc atcctccgga aaatattcac      180
caccatctca ttctgcattg ttctgcgcat ggcggtcact cggcaatttc cctgggctgt     240
acaaacatgg tatgactctc ttggagcaat aaacaaaata caggtaatgt accataatgc     300
tgcattatat actatgattt aaataatcag tcaatagatc agttctaat               349

<210> SEQ ID NO 63
<211> LENGTH: 82
<212> TYPE: PRT
<213> ORGANISM: Homo sapiens

<400> SEQUENCE: 63

```
Thr Glu Leu Lys Leu Thr Arg Lys Ala Ala Tyr Val Arg Tyr Phe Asn
1               5                   10                  15

Ser Ser Ala Phe Phe Phe Ser Gly Phe Val Val Phe Leu Ser Val
                20                  25                  30

Leu Pro Tyr Ala Leu Ile Lys Gly Ile Ile Leu Arg Lys Ile Phe Thr
            35                  40                  45

Thr Ile Ser Phe Cys Ile Val Leu Arg Met Ala Val Thr Arg Gln Phe
    50                  55                  60

Pro Trp Ala Val Gln Thr Trp Tyr Asp Ser Leu Gly Ala Ile Asn Lys
65                  70                  75                  80

Ile Gln
```

<210> SEQ ID NO 64
<211> LENGTH: 30
<212> TYPE: DNA
<213> ORGANISM: Homo sapiens

<400> SEQUENCE: 64
tataagatgt agcacaatga gagtataaag                                30

<210> SEQ ID NO 65
<211> LENGTH: 221
<212> TYPE: DNA
<213> ORGANISM: Homo sapiens

<400> SEQUENCE: 65
agcacaatga gagtataaag tagatgtaat aatgcattaa tgctattctg attctataat      60

```
atgttttgc tctctttat aaataggatt tcttacaaaa gcaagaatat aagacattgg      120
aatataactt aacgactaca gaagtagtga tggagaatgt aacagccttc tgggaggagg    180 tcagaattt taaaaaattg tttgctctaa cacctaact g                          221
```

<210> SEQ ID NO 66
<211> LENGTH: 31
<212> TYPE: PRT
<213> ORGANISM: Homo sapiens

<400> SEQUENCE: 66

```
Asp Phe Leu Gln Lys Gln Glu Tyr Lys Thr Leu Glu Tyr Asn Leu Thr
1               5                   10                  15
Thr Thr Glu Val Val Met Glu Asn Val Thr Ala Phe Trp Glu Glu
            20                  25                  30
```

<210> SEQ ID NO 67
<211> LENGTH: 30
<212> TYPE: DNA
<213> ORGANISM: Homo sapiens

<400> SEQUENCE: 67

```
gtgtatgtgt atgtatacat gtatgtattc                                     30
```

<210> SEQ ID NO 68
<211> LENGTH: 28
<212> TYPE: DNA
<213> ORGANISM: Homo sapiens

<400> SEQUENCE: 68

```
catctattga aaatatctga caaactca                                       28
```

<210> SEQ ID NO 69
<211> LENGTH: 230
<212> TYPE: DNA
<213> ORGANISM: Homo sapiens

<400> SEQUENCE: 69

```
gtgtgtgtgt gtgtgttttt taacaggga tttggggaat tatttgagaa agcaaaacaa     60
aacaataaca atagaaaaac ttctaatggt gatgacagcc tcttcttcag taatttctca    120
cttcttggta ctcctgtcct gaaagatatt aatttcaaga tagaaagagg acagttgttg    180
gcggttgctg gatccactgg agcaggcaag gtagttcttt tgttcttcac                230
```

<210> SEQ ID NO 70
<211> LENGTH: 61
<212> TYPE: PRT
<213> ORGANISM: Homo sapiens

<400> SEQUENCE: 70

```
Gly Phe Gly Glu Leu Phe Glu Lys Ala Lys Gln Asn Asn Asn Asn Arg
1               5                   10                  15
Lys Thr Ser Asn Gly Asp Asp Ser Leu Phe Phe Ser Asn Phe Ser Leu
            20                  25                  30
Leu Gly Thr Pro Val Leu Lys Asp Ile Asn Phe Lys Ile Glu Arg Gly
            35                  40                  45
Gln Leu Leu Ala Val Ala Gly Ser Thr Gly Ala Gly Lys
        50                  55                  60
```

<210> SEQ ID NO 71

-continued

```
<211> LENGTH: 23
<212> TYPE: DNA
<213> ORGANISM: Homo sapiens

<400> SEQUENCE: 71 aacttaatttt ggtgtccatg tct                                           23

<210> SEQ ID NO 72
<211> LENGTH: 294
<212> TYPE: DNA
<213> ORGANISM: Homo sapiens

<400> SEQUENCE: 72
aggatgataa ttggaggcaa gtgaatcctg agcgtgattt gataatgacc taataatgat    60
gggttttatt tccagacttc acttctaatg atgattatgg gagaactgga gccttcagag   120
ggtaaaatta agcacagtgg aagaatttca ttctgttctc agttttcctg gattatgcct   180
ggcaccatta agaaaatat catctttggt gtttcctatg atgaatatag atacagaagc    240
gtcatcaaag catgccaact agaagaggta agaaactatg tgaaaacttt ttga          294

<210> SEQ ID NO 73
<211> LENGTH: 64
<212> TYPE: PRT
<213> ORGANISM: Homo sapiens

<400> SEQUENCE: 73

Thr Ser Leu Leu Met Val Ile Met Gly Glu Leu Glu Pro Ser Glu Gly
1               5                   10                  15

Lys Ile Lys His Ser Gly Arg Ile Ser Phe Cys Ser Gln Phe Ser Trp
            20                  25                  30

Ile Met Pro Gly Thr Ile Lys Glu Asn Ile Ile Phe Gly Val Ser Tyr
        35                  40                  45

Asp Glu Tyr Arg Tyr Arg Ser Val Ile Lys Ala Cys Gln Leu Glu Glu
    50                  55                  60

<210> SEQ ID NO 74
<211> LENGTH: 64
<212> TYPE: DNA
<213> ORGANISM: Homo sapiens

<400> SEQUENCE: 74 atgaacccctt cacactaccc aaattatata tttggctcca tattcaatcg gttagtctac    60
atat                                                                  64

<210> SEQ ID NO 75
<211> LENGTH: 209
<212> TYPE: DNA
<213> ORGANISM: Homo sapiens

<400> SEQUENCE: 75
agattgagca tactaaaagt gactctctaa ttttctatttt tggtaatag acatctcca     60 agtttgcaga gaaagacaat atagttcttg gagaaggtgg aatcacactg agtggaggtc   120
aacgagcaag aatttcttta gcaaggtgaa taactaatta ttggtctagc aagcatttgc   180
tgtaaatgtc attcatgtaa aaaaattac                                      209

<210> SEQ ID NO 76
<211> LENGTH: 31
<212> TYPE: PRT
<213> ORGANISM: Homo sapiens
```

-continued

```
<400> SEQUENCE: 76

Asp Ile Ser Lys Phe Ala Glu Lys Asp Asn Ile Val Leu Gly Glu Gly
1               5                   10                  15

Gly Ile Thr Leu Ser Gly Gly Gln Arg Ala Arg Ile Ser Leu Ala
            20                  25                  30

<210> SEQ ID NO 77
<211> LENGTH: 30
<212> TYPE: DNA
<213> ORGANISM: Homo sapiens

<400> SEQUENCE: 77
tagacatcca acatagaact gagtttgtgt                                      30

<210> SEQ ID NO 78
<211> LENGTH: 27
<212> TYPE: DNA
<213> ORGANISM: Homo sapiens

<400> SEQUENCE: 78
atctgtgagc caaagtaaga cttattc                                         27

<210> SEQ ID NO 79
<211> LENGTH: 22
<212> TYPE: DNA
<213> ORGANISM: Homo sapiens

<400> SEQUENCE: 79
tgctgtaagg tgcacacact tt                                              22

<210> SEQ ID NO 80
<211> LENGTH: 30
<212> TYPE: DNA
<213> ORGANISM: Homo sapiens

<400> SEQUENCE: 80
taagtaaggt tactatcaat cacacctgaa                                      30

<210> SEQ ID NO 81
<211> LENGTH: 67
<212> TYPE: DNA
<213> ORGANISM: Homo sapiens

<400> SEQUENCE: 81
ctgcaccact tttgagaata gtgttatttc agtgaatcga tgtggtgacc atattgtaat     60
gcatgta                                                               67

<210> SEQ ID NO 82
<211> LENGTH: 205
<212> TYPE: DNA
<213> ORGANISM: Homo sapiens

<400> SEQUENCE: 82
taaggcaaat catctacact agatgaccag gaaatagag aggaaatgta atttaatttc      60
cattttcttt ttagagcagt atacaaagat gctgatttgt atttattaga ctctcctttt    120
ggatacctag atgttttaac agaaaagaa atatttgaaa ggtatgttct ttgaataccta    180 tacttataat gctcatgcta aaata                                          205

<210> SEQ ID NO 83
```

```
<211> LENGTH: 28
<212> TYPE: PRT
<213> ORGANISM: Homo sapiens

<400> SEQUENCE: 83

Ala Val Tyr Lys Asp Ala Asp Leu Tyr Leu Leu Asp Ser Pro Phe Gly
1               5                   10                  15

Tyr Leu Asp Val Leu Thr Glu Lys Glu Ile Phe Glu
            20                  25

<210> SEQ ID NO 84
<211> LENGTH: 30
<212> TYPE: DNA
<213> ORGANISM: Homo sapiens

<400> SEQUENCE: 84
aactcaaatc tgatctgccc tactgggcca                                        30

<210> SEQ ID NO 85
<211> LENGTH: 790
<212> TYPE: DNA
<213> ORGANISM: Homo sapiens

<400> SEQUENCE: 85
gtttttatat cttaaagctg tgtctgtaaa ctgatggcta acaaaactag gattttggtc       60
acttctaaaa tggaacattt aaagaaagct gacaaaatat taattttgca tgaaggtagc     120
agctattttt atgggacatt ttcagaactc caaatctac agccagactt agctcaaaa       180 ctcatgggat gtgattcttt cgaccaattt agtgcagaaa gaagaaattc aatcctaact     240
gagaccttac accgtttctc attagaagga gatgctcctg tctcctggac agaaacaaaa     300
aaacaatctt taaacagac tggagagttt ggggaaaaaa ggaagaattc tattctcaat     360
ccaatcaact ctatacgaaa attttccatt gtgcaaaaga ctcccttaca aatgaatggc     420
atcgaagagg attctgatga gcctttagag agaaggctgt ccttagtacc agattctgag     480
cagggagagg cgatactgcc tcgcatcagc gtgatcagca ctggccccac gcttcaggca     540
cgaaggaggc agtctgtcct gaacctgatg acacactcag ttaaccaagg tcagaacatt     600
caccgaaaga caacagcatc cacacgaaaa gtgtcactgg cccctcaggc aaacttgact     660
gaactggata tatattcaag aaggttatct caagaaactg gcttggaaat aagtgaagaa     720
attaacgaag aagacttaaa ggtaggtata catcgcttgg gggtatttca cccacagaat     780
gcaattgagt                                                           790

<210> SEQ ID NO 86
<211> LENGTH: 241
<212> TYPE: PRT
<213> ORGANISM: Homo sapiens

<400> SEQUENCE: 86

Cys Val Cys Lys Leu Met Ala Asn Lys Thr Arg Ile Leu Val Thr Ser
1               5                   10                  15

Lys Met Glu His Leu Lys Lys Ala Asp Lys Ile Leu Ile Leu His Glu
            20                  25                  30

Gly Ser Ser Tyr Phe Tyr Gly Thr Phe Ser Glu Leu Gln Asn Leu Gln
        35                  40                  45

Pro Asp Phe Ser Ser Lys Leu Met Gly Cys Asp Ser Phe Asp Gln Phe
    50                  55                  60

Ser Ala Glu Arg Arg Asn Ser Ile Leu Thr Glu Thr Leu His Arg Phe
```

```
                65                  70                  75                  80
Ser Leu Glu Gly Asp Ala Pro Val Ser Trp Thr Glu Thr Lys Lys Gln
                    85                  90                  95

Ser Phe Lys Gln Thr Gly Glu Phe Gly Glu Lys Arg Lys Asn Ser Ile
                100                 105                 110

Leu Asn Pro Ile Asn Ser Ile Arg Lys Phe Ser Ile Val Gln Lys Thr
                115                 120                 125

Pro Leu Gln Met Asn Gly Ile Glu Glu Asp Ser Asp Glu Pro Leu Glu
            130                 135                 140

Arg Arg Leu Ser Leu Val Pro Asp Ser Glu Gln Gly Glu Ala Ile Leu
145                 150                 155                 160

Pro Arg Ile Ser Val Ile Ser Thr Gly Pro Thr Leu Gln Ala Arg Arg
                165                 170                 175

Arg Gln Ser Val Leu Asn Leu Met Thr His Ser Val Asn Gln Gly Gln
                180                 185                 190

Asn Ile His Arg Lys Thr Thr Ala Ser Thr Arg Lys Val Ser Leu Ala
                195                 200                 205

Pro Gln Ala Asn Leu Thr Glu Leu Asp Ile Tyr Ser Arg Arg Leu Ser
            210                 215                 220

Gln Glu Thr Gly Leu Glu Ile Ser Glu Glu Ile Asn Glu Glu Asp Leu
225                 230                 235                 240

Lys

<210> SEQ ID NO 87
<211> LENGTH: 217
<212> TYPE: DNA
<213> ORGANISM: Homo sapiens

<400> SEQUENCE: 87
caatggtggc atgaaactgt actgtcttat tgtaatagcc ataattcttt tattcaggag    60
tgcttttttg atgatatgga gagcatacca gcagtgacta catggaacac ataccttcga   120
tatattactg tccacaagag cttaattttt gtgctaattt ggtgcttagt aattttttctg  180 gcagaggtaa gaatgttcta ttgtaaagta ttactgg                            217

<210> SEQ ID NO 88
<211> LENGTH: 43
<212> TYPE: PRT
<213> ORGANISM: Homo sapiens

<400> SEQUENCE: 88

Glu Cys Phe Phe Asp Asp Met Glu Ser Ile Pro Ala Val Thr Thr Trp
1               5                   10                  15

Asn Thr Tyr Leu Arg Tyr Ile Thr Val His Lys Ser Leu Ile Phe Val
                20                  25                  30

Leu Ile Trp Cys Leu Val Ile Phe Leu Ala Glu
            35                  40

<210> SEQ ID NO 89
<211> LENGTH: 32
<212> TYPE: DNA
<213> ORGANISM: Homo sapiens

<400> SEQUENCE: 89
aagttaaatt aagatagttt ggggatgtat ac                                  32

<210> SEQ ID NO 90
```

<211> LENGTH: 30
<212> TYPE: DNA
<213> ORGANISM: Homo sapiens

<400> SEQUENCE: 90
ccttgatatt ggtacacaca tcaaatggtg                                    30

<210> SEQ ID NO 91
<211> LENGTH: 141
<212> TYPE: DNA
<213> ORGANISM: Homo sapiens

<400> SEQUENCE: 91
gggaggaata ggtgaagatg ttagaaaaaa aatcaactgt gtcttgttcc attccaggtg    60
gctgcttctt tggttgtgct gtggctcctt ggaaagtgag tattccatgt cctattgtgt   120
agattgtgtt ttatttctgt t                                            141

<210> SEQ ID NO 92
<211> LENGTH: 12
<212> TYPE: PRT
<213> ORGANISM: Homo sapiens

<400> SEQUENCE: 92

Val Ala Ala Ser Leu Val Val Leu Trp Leu Leu Gly
1               5                   10

<210> SEQ ID NO 93
<211> LENGTH: 28
<212> TYPE: DNA
<213> ORGANISM: Homo sapiens

<400> SEQUENCE: 93
tgtaatccac tatgtttgta tgtattgt                                      28

<210> SEQ ID NO 94
<211> LENGTH: 30
<212> TYPE: DNA
<213> ORGANISM: Homo sapiens

<400> SEQUENCE: 94
gcatgctctt ctaatgcaaa atattgtatt                                    30

<210> SEQ ID NO 95
<211> LENGTH: 330
<212> TYPE: DNA
<213> ORGANISM: Homo sapiens

<400> SEQUENCE: 95
ggctgccaaa taacgatttc ctatttgctt tacagcactc ctcttcaaga caaagggaat    60
agtactcata gtagaaataa cagctatgca gtgattatca ccagcaccag ttcgtattat   120
gtgttttaca tttacgtggg agtagccgac actttgcttg ctatgggatt cttcagaggt   180
ctaccactgg tgcatactct aatcacagtg tcgaaaattt tacaccacaa aatgttacat   240
tctgttcttc aagcacctat gtcaacccte aacacgttga agcaggtac tttactaggt    300 ctaagaaatg aaactgctga tccaccatca                                   330

<210> SEQ ID NO 96
<211> LENGTH: 83
<212> TYPE: PRT
<213> ORGANISM: Homo sapiens

<400> SEQUENCE: 96

Thr Pro Leu Gln Asp Lys Gly Asn Ser Thr His Ser Arg Asn Asn Ser
1               5                   10                  15

Tyr Ala Val Ile Ile Thr Ser Thr Ser Ser Tyr Tyr Val Phe Tyr Ile
                20                  25                  30

Tyr Val Gly Val Ala Asp Thr Leu Leu Ala Met Gly Phe Phe Arg Gly
            35                  40                  45

Leu Pro Leu Val His Thr Leu Ile Thr Val Ser Lys Ile Leu His His
    50                  55                  60

Lys Met Leu His Ser Val Leu Gln Ala Pro Met Ser Thr Leu Asn Thr
65                  70                  75                  80

Leu Lys Ala

<210> SEQ ID NO 97
<211> LENGTH: 71
<212> TYPE: DNA
<213> ORGANISM: Homo sapiens

<400> SEQUENCE: 97
tgggttctga atgcgtctac tgtgatccaa acttagtatt gaatatattg atatatcttt    60
aaaaaattag t                                                        71

<210> SEQ ID NO 98
<211> LENGTH: 168
<212> TYPE: DNA
<213> ORGANISM: Homo sapiens

<400> SEQUENCE: 98
tgaggaattt gtcatcttgt atattatagg tgggattctt aatagattct ccaaagatat    60
agcaattttg gatgaccttc tgcctcttac catatttgac ttcatccagg tatgtaaaaa   120
taagtaccgt taagtatgtc tgtattatta aaaaaacaat aacaaaag               168

<210> SEQ ID NO 99
<211> LENGTH: 26
<212> TYPE: PRT
<213> ORGANISM: Homo sapiens

<400> SEQUENCE: 99

Gly Ile Leu Asn Arg Phe Ser Lys Asp Ile Ala Ile Leu Asp Asp Leu
1               5                   10                  15

Leu Pro Leu Thr Ile Phe Asp Phe Ile Gln
            20                  25

<210> SEQ ID NO 100
<211> LENGTH: 30
<212> TYPE: DNA
<213> ORGANISM: Homo sapiens

<400> SEQUENCE: 100
gtttaaagta tgcaaaaaaa aaaaagaaa                                     30

<210> SEQ ID NO 101
<211> LENGTH: 22
<212> TYPE: DNA
<213> ORGANISM: Homo sapiens

<400> SEQUENCE: 101
tgacacactt tgtccacttt gc                                            22

<210> SEQ ID NO 102
<211> LENGTH: 249
<212> TYPE: DNA
<213> ORGANISM: Homo sapiens

<400> SEQUENCE: 102

```
tgaaaatgtt tactcaccaa catgttttct ttgatcttac agttgttatt aattgtgatt      60
ggagctatag cagttgtcgc agttttacaa ccctacatct ttgttgcaac agtgccagtg     120
atagtggctt ttattatgtt gagagcatat ttcctccaaa cctcacagca actcaaacaa     180
ctggaatctg aaggtatgac agtgaatgtg cgatactcat cttgtaaaaa agctataaga     240
gctatttga                                                             249
```

<210> SEQ ID NO 103
<211> LENGTH: 50
<212> TYPE: PRT
<213> ORGANISM: Homo sapiens

<400> SEQUENCE: 103

```
Leu Leu Leu Ile Val Ile Gly Ala Ile Ala Val Val Ala Val Leu Gln
1               5                   10                  15

Pro Tyr Ile Phe Val Ala Thr Val Pro Val Ile Val Ala Phe Ile Met
            20                  25                  30

Leu Arg Ala Tyr Phe Leu Gln Thr Ser Gln Gln Leu Lys Gln Leu Glu
        35                  40                  45

Ser Glu
    50
```

<210> SEQ ID NO 104
<211> LENGTH: 30
<212> TYPE: DNA
<213> ORGANISM: Homo sapiens

<400> SEQUENCE: 104

```
tttgtgatat gattattcta atttagtctt                                       30
```

<210> SEQ ID NO 105
<211> LENGTH: 362
<212> TYPE: DNA
<213> ORGANISM: Homo sapiens

<400> SEQUENCE: 105

```
tcaggtacaa gatattatga aattacattt tgtgtttatg ttatttgcaa tgttttctat      60
ggaaatattt cacaggcagg agtccaattt tcactcatct tgttacaagc ttaaaaggac     120
tatggacact tcgtgccttc ggacggcagc cttactttga aactctgttc cacaaagctc     180
tgaatttaca tactgccaac tggttcttgt acctgtcaac actgcgctgg ttccaaatga     240
gaatagaaat gattttgtc atcttcttca ttgctgttac cttcatttcc attttaacaa     300
caggtactat gaactcatta actttagcta agcatttaag taaaaaattt tcaatgaata     360
aa                                                                    362
```

<210> SEQ ID NO 106
<211> LENGTH: 75
<212> TYPE: PRT
<213> ORGANISM: Homo sapiens

<400> SEQUENCE: 106

```
Arg Ser Pro Ile Phe Thr His Leu Val Thr Ser Leu Lys Gly Leu Trp
```

```
                 1               5                  10                  15
              Thr Leu Arg Ala Phe Gly Arg Gln Pro Tyr Phe Glu Thr Leu Phe His
                           20                  25                  30

Lys Ala Leu Asn Leu His Thr Ala Asn Trp Phe Leu Tyr Leu Ser Thr
                           35                  40                  45

Leu Arg Trp Phe Gln Met Arg Ile Glu Met Ile Phe Val Ile Phe Phe
                           50                  55                  60

Ile Ala Val Thr Phe Ile Ser Ile Leu Thr Thr
               65                  70                  75
```

<210> SEQ ID NO 107
<211> LENGTH: 30
<212> TYPE: DNA
<213> ORGANISM: Homo sapiens

<400> SEQUENCE: 107
gctgtgatga actgagattt aaaaattgtt                                      30

<210> SEQ ID NO 108
<211> LENGTH: 184
<212> TYPE: DNA
<213> ORGANISM: Homo sapiens

<400> SEQUENCE: 108
ataaagtcgt tcacagaaga gagaaataac atgaggttca tttacgtctt ttgtgcatct     60
ataggagaag gagaaggaag agttggtatt atcctgactt tagccatgaa tatcatgagt    120
acattgcagt gggctgtaaa ctccagcata gatgtggata gcttggtaag tcttatcatc    180
tttt                                                                 184

<210> SEQ ID NO 109
<211> LENGTH: 33
<212> TYPE: PRT
<213> ORGANISM: Homo sapiens

<400> SEQUENCE: 109

```
              Glu Gly Glu Gly Arg Val Gly Ile Ile Leu Thr Leu Ala Met Asn Ile
               1               5                  10                  15

Met Ser Thr Leu Gln Trp Ala Val Asn Ser Ser Ile Asp Val Asp Ser
                           20                  25                  30

Leu
```

<210> SEQ ID NO 110
<211> LENGTH: 32
<212> TYPE: DNA
<213> ORGANISM: Homo sapiens

<400> SEQUENCE: 110
ttatgaaaaa aattcagaca agtaacaaag ta                                   32

<210> SEQ ID NO 111
<211> LENGTH: 30
<212> TYPE: DNA
<213> ORGANISM: Homo sapiens

<400> SEQUENCE: 111
cgacaaataa ccaagtgaca aatagcaagt                                      30

<210> SEQ ID NO 112
<211> LENGTH: 41

<210> SEQ ID NO 112
<211> LENGTH: 41
<212> TYPE: DNA
<213> ORGANISM: Homo sapiens

<400> SEQUENCE: 112 tatttttag gaagcatcaa actaattgtg aaattgtctg c                 41

<210> SEQ ID NO 113
<211> LENGTH: 302
<212> TYPE: DNA
<213> ORGANISM: Homo sapiens

<400> SEQUENCE: 113
cttaaaaaca aaatgttgt tattttatt tcagatgcga tctgtgagcc gagtctttaa    60
gttcattgac atgccaacag aaggtaaacc taccaagtca accaaaccat acaagaatgg  120
ccaactctcg aaagttatga ttattgagaa ttcacacgtg aagaaagatg acatctggcc  180
ctcagggggc caaatgactg tcaaagatct cacagcaaaa tacacagaag gtggaaatgc  240
catattagag aacatttcct tctcaataag tcctggccag agggtgagat ttgaacactg  300
ct                                                                302

<210> SEQ ID NO 114
<211> LENGTH: 83
<212> TYPE: PRT
<213> ORGANISM: Homo sapiens

<400> SEQUENCE: 114

Met Arg Ser Val Ser Arg Val Phe Lys Phe Ile Asp Met Pro Thr Glu
 1               5                  10                  15

Gly Lys Pro Thr Lys Ser Thr Lys Pro Tyr Lys Asn Gly Gln Leu Ser
                20                  25                  30

Lys Val Met Ile Ile Glu Asn Ser His Val Lys Lys Asp Asp Ile Trp
         35                  40                  45

Pro Ser Gly Gly Gln Met Thr Val Lys Asp Leu Thr Ala Lys Tyr Thr
     50                  55                  60

Glu Gly Gly Asn Ala Ile Leu Glu Asn Ile Ser Phe Ser Ile Ser Pro
 65                  70                  75                  80

Gly Gln Arg

<210> SEQ ID NO 115
<211> LENGTH: 52
<212> TYPE: DNA
<213> ORGANISM: Homo sapiens

<400> SEQUENCE: 115
tgttagactg tgttcagtaa gtgaatccca gtagcctgaa gcaatgtgtt ag          52

<210> SEQ ID NO 116
<211> LENGTH: 30
<212> TYPE: DNA
<213> ORGANISM: Homo sapiens

<400> SEQUENCE: 116
aggtttgaat gaataagtga aaatcttcca                                   30

<210> SEQ ID NO 117
<211> LENGTH: 30
<212> TYPE: DNA
<213> ORGANISM: Homo sapiens

<400> SEQUENCE: 117

```
tccaatggtt tttattgaag tacaatactg                                    30
```

<210> SEQ ID NO 118
<211> LENGTH: 30
<212> TYPE: DNA
<213> ORGANISM: Homo sapiens

<400> SEQUENCE: 118

```
ttatggcatg gtacctatat gtcacagaag                                    30
```

<210> SEQ ID NO 119
<211> LENGTH: 238
<212> TYPE: DNA
<213> ORGANISM: Homo sapiens

<400> SEQUENCE: 119

```
gtcacagaag tgatcccatc acttttacct tataggtggg cctcttggga agaactggat   60
cagggaagag tactttgtta tcagcttttt tgagactact gaacactgaa ggagaaatcc  120
agatcgatgg tgtgtcttgg gattcaataa ctttgcaaca gtggaggaaa gcctttggag  180
tgataccaca ggtgagcaaa aggacttagc cagaaaaaag gcaactaaat tatatttt    238
```

<210> SEQ ID NO 120
<211> LENGTH: 52
<212> TYPE: PRT
<213> ORGANISM: Homo sapiens

<400> SEQUENCE: 120

Val Gly Leu Leu Gly Arg Thr Gly Ser Gly Lys Ser Thr Leu Leu Ser
1               5                   10                  15

Ala Phe Leu Arg Leu Leu Asn Thr Glu Gly Glu Ile Gln Ile Asp Gly
            20                  25                  30

Val Ser Trp Asp Ser Ile Thr Leu Gln Gln Trp Arg Lys Ala Phe Gly
        35                  40                  45

Val Ile Pro Gln
    50

<210> SEQ ID NO 121
<211> LENGTH: 26
<212> TYPE: DNA
<213> ORGANISM: Homo sapiens

<400> SEQUENCE: 121

```
ctgctatttg atacttgtac tcaaga                                        26
```

<210> SEQ ID NO 122
<211> LENGTH: 30
<212> TYPE: DNA
<213> ORGANISM: Homo sapiens

<400> SEQUENCE: 122

```
ctccaaatat tgctgtagta tttgtttctt                                    30
```

<210> SEQ ID NO 123
<211> LENGTH: 232
<212> TYPE: DNA
<213> ORGANISM: Homo sapiens

<400> SEQUENCE: 123

```
ggtgtttctt attttaaaat aatttttcta cttgaaatat tttacaatac aataagggaa   60
```
aaataaaaag ttatttaagt tattcatact ttcttcttct tttcttttt gctatagaaa      120 gtatttattt tttctggaac atttagaaaa aacttggatc cctatgaaca gtggagtgat      180
caagaaatat ggaaagttgc agatgaggta aggctgctaa ctgaaatgat tt             232

<210> SEQ ID NO 124
<211> LENGTH: 30
<212> TYPE: PRT
<213> ORGANISM: Homo sapiens

<400> SEQUENCE: 124

Lys Val Phe Ile Phe Ser Gly Thr Phe Arg Lys Asn Leu Asp Pro Tyr
1               5                   10                  15

Glu Gln Trp Ser Asp Gln Glu Ile Trp Lys Val Ala Asp Glu
            20                  25                  30

<210> SEQ ID NO 125
<211> LENGTH: 30
<212> TYPE: DNA
<213> ORGANISM: Homo sapiens

<400> SEQUENCE: 125
tgtgccacgt attgttttct tactactttt                                        30

<210> SEQ ID NO 126
<211> LENGTH: 215
<212> TYPE: DNA
<213> ORGANISM: Homo sapiens

<400> SEQUENCE: 126
tttttaactc tgtggtatct gaactatctt ctctaactgc aggttgggct cagatctgtg       60
atagaacagt ttcctgggaa gcttgacttt gtccttgtgg atgggggctg tgtcctaagc      120
catggccaca agcagttgat gtgcttggct agatctgttc tcagtaaggc gaagatcttg      180
ctgcttgatg aacccagtgc tcatttggat ccagt                                 215

<210> SEQ ID NO 127
<211> LENGTH: 57
<212> TYPE: PRT
<213> ORGANISM: Homo sapiens

<400> SEQUENCE: 127

Val Gly Leu Arg Ser Val Ile Glu Gln Phe Pro Gly Lys Leu Asp Phe
1               5                   10                  15

Val Leu Val Asp Gly Gly Cys Val Leu Ser His Gly His Lys Gln Leu
            20                  25                  30

Met Cys Leu Ala Arg Ser Val Leu Ser Lys Ala Lys Ile Leu Leu Leu
        35                  40                  45

Asp Glu Pro Ser Ala His Leu Asp Pro
    50                  55

<210> SEQ ID NO 128
<211> LENGTH: 28
<212> TYPE: DNA
<213> ORGANISM: Homo sapiens

<400> SEQUENCE: 128
agtttcagat gttctgttac ttaatagc                                          28

<210> SEQ ID NO 129
<211> LENGTH: 30

```
<212> TYPE: DNA
<213> ORGANISM: Homo sapiens

<400> SEQUENCE: 129
tgattgtggc taacgctata tcaacattat                                           30

<210> SEQ ID NO 130
<211> LENGTH: 30
<212> TYPE: DNA
<213> ORGANISM: Homo sapiens

<400> SEQUENCE: 130
attactgttc tgtgatatta tgtgtggtat                                           30

<210> SEQ ID NO 131
<211> LENGTH: 30
<212> TYPE: DNA
<213> ORGANISM: Homo sapiens

<400> SEQUENCE: 131
tgaaaagaac ttaaagaaat aagtaattta                                           30

<210> SEQ ID NO 132
<211> LENGTH: 152
<212> TYPE: DNA
<213> ORGANISM: Homo sapiens

<400> SEQUENCE: 132
aacataccaa ataattagaa gaactctaaa acaagcattt gctgattgca cagtaattct          60
ctgtgaacac aggatagaag caatgctgga atgccaacaa ttttttggtga gtctttataa       120 ctttacttaa gatctcattg cccttgtaat tc                                      152

<210> SEQ ID NO 133
<211> LENGTH: 35
<212> TYPE: PRT
<213> ORGANISM: Homo sapiens

<400> SEQUENCE: 133

Thr Tyr Gln Ile Ile Arg Arg Thr Leu Lys Gln Ala Phe Ala Asp Cys
1               5                   10                  15

Thr Val Ile Leu Cys Glu His Arg Ile Glu Ala Met Leu Glu Cys Gln
            20                  25                  30

Gln Phe Leu
        35

<210> SEQ ID NO 134
<211> LENGTH: 285
<212> TYPE: DNA
<213> ORGANISM: Homo sapiens

<400> SEQUENCE: 134
ccttctgtcc cagatctcac taacagccat ttccctaggt catagaagag aacaaagtgc          60
ggcagtacga ttccatccag aaactgctga acgagaggag cctcttccgg caagccatca       120
gcccctccga cagggtgaag ctctttcccc accggaactc aagcaagtgc aagtctaagc       180
cccagattgc tgctctgaaa gaggagacag aagaaggt gcaagataca aggctttaga        240
gagcagcata aatgtgacat gggacatttg ctcatggaat tggag                      285

<210> SEQ ID NO 135
<211> LENGTH: 66
```

-continued

```
<212> TYPE: PRT
<213> ORGANISM: Homo sapiens

<400> SEQUENCE: 135

Val Ile Glu Glu Asn Lys Val Arg Gln Tyr Asp Ser Ile Gln Lys Leu
1               5                  10                  15

Leu Asn Glu Arg Ser Leu Phe Arg Gln Ala Ile Ser Pro Ser Asp Arg
            20                  25                  30

Val Lys Leu Phe Pro His Arg Asn Ser Ser Lys Cys Lys Ser Lys Pro
        35                  40                  45

Gln Ile Ala Ala Leu Lys Glu Glu Thr Glu Glu Glu Val Gln Asp Thr
    50                  55                  60

Arg Leu
65

<210> SEQ ID NO 136
<211> LENGTH: 18
<212> TYPE: DNA
<213> ORGANISM: Homo sapiens

<400> SEQUENCE: 136
tgacatggga catttgct                                                 18
```

METHODS AND SYSTEMS FOR SEQUENTIAL DETERMINATION OF GENETIC MUTATIONS AND/OR VARIANTS

INCORPORATION BY REFERENCE

This application claims priority to U.S. Provisional Application No. 61/350,893 filed Jun. 2, 2010. Reference is also made to the corresponding PCT application filed concurrently herewith under attorney docket number 0800-9622-PCT. The foregoing applications, as well as all documents cited in the foregoing applications ("application documents") and all documents cited or referenced in the application documents are hereby incorporated herein by reference in their entirety. Also, all documents cited in this application ("herein-cited documents") and all documents cited or referenced in herein-cited documents are incorporated herein by reference in their entirety. In addition, any manufacturer's instructions or catalogues for any products cited or mentioned in each of the application documents or herein-cited documents are incorporated by reference in their entirety. Documents incorporated by reference into this text or any teachings therein can be used in the practice of this invention and, technology in each of the documents incorporated herein by reference can be used in the practice of this invention. Documents incorporated by reference into this text are not admitted to be prior art.

SEQUENCE LISTING

The instant application contains a Sequence Listing which has been submitted in ASCII format via EFS-Web and is hereby incorporated by reference in its entirety. Said ASCII copy, created on Dec. 16, 2011, is named 3400000.txt and is 41,1321 bytes in size.

It is noted that in this disclosure, terms such as "comprises", "comprised", "comprising", "contains", "containing" and the like can have the meaning attributed to them in U.S. patent law; e.g., they can mean "includes", "included", "including" and the like. Terms such as "consisting essentially of" and "consists essentially of" have the meaning attributed to them in U.S. patent law, e.g., they allow for the inclusion of additional ingredients or steps that do not detract from the novel or basic characteristics of the invention, i.e., they exclude additional unrecited ingredients or steps that detract from novel or basic characteristics of the invention, and they exclude ingredients or steps of the prior art, such as documents in the art that are cited herein or are incorporated by reference herein, especially as it is a goal of this document to define embodiments that are patentable, e.g., novel, nonobvious, inventive, over the prior art, e.g., over documents cited herein or incorporated by reference herein. And, the terms "consists of" and "consisting of" have the meaning ascribed to them in U.S. patent law; namely, that these terms are closed ended.

FIELD OF THE INVENTION

The present invention relates to methods and systems for the determination of mutations, including insertions, deletions and the like in a given gene.

The identification of a mutation causing a genetic disease or disorder for purposes of carrier screening or diagnosis can be time consuming and labor intensive due to the large number of mutations within a single gene that can be causative of a disease or carrier state. Therefore, the present invention relates to a sequential method of analyzing a genetic sample for mutations in a manner that is both time- and cost-effective. More specifically, embodiments of the present invention relate to methods and systems of analyzing patient samples for mutations sequentially on a microfluidic device including performing amplification reactions, such as PCR, and thermal melt analysis.

BACKGROUND

Numerous disorders, including Cystic Fibrosis (CF) and Medium Chain Acyl-CoA Dehydrogenase (MCAD) Deficiency are caused by any one of a number of mutations within the relevant gene.

In 2001, the American College of Medical Genetics (ACMG) and the American College of Obstetrics and Gynecologist (ACOG) recommended that reproductive couples be offered Cystic Fibrosis (CF) screening. CF is caused by mutations in the cystic fibrosis transmembrane regulator gene (CFTR) and is one of the most common autosomal recessive diseases in the North American Caucasian population with an incidence of 1 in 2500-3000 live births (Rommens (1989) and Palomaki (2002)). The carrier frequency of this disease in Northern European, Ashkenazi Jews, Hispanic, African American and Asian descendents is 1 in 25, 1 in 29, 1 in 46, 1 in 65, and 1 in 90, respectively (Grody (2001), Watson (2004)). There are more than 1500 mutations in the CFTR gene as reported by the Cystic Fibrosis Genetic Analysis Consortium (http://www.genet.sickkids.on.ca/cftr). Each mutation has various frequencies in different populations. For instance, the mutation DF508 is a mutation that results in deletion of the amino acid phenylalanine at residue 508 and accounts for more than 66% of all CF mutations (Bobadilla, 2002). Cystic Fibrosis has been historically detected by a positive immunoreactive trypsinogen test and more recently by sequencing of the CFTR gene.

ACOG has identified the 23 most common CF causing mutations, which are commonly utilized as the industry standard for genetic testing of CF (see FIG. 1).

Medium-chain acyl-coenzyme A dehydrogenase (MCAD) deficiency is a condition that prevents the body from converting certain fats to energy, particularly during periods without food (fasting). MCAD deficiency is an inborn metabolic disorder with an incidence of 1 in 10,000 births and can result in death or serious disability. In the United States, the estimated incidence of MCAD deficiency is 1 in 17,000 people. The condition is more common among individuals of northern European ancestry.

People with MCAD deficiency are at risk for serious complications such as seizures, breathing difficulties, liver problems, brain damage, coma, and sudden death. These outcomes can be prevented via diet modification by early diagnosis.

MCAD deficiency is caused by a mutation in the acyl-Coenzyme A dehydrogenase, C-4 to C-12 straight chain gene (ACADM). More than 80 different mutations in the ACADM gene have been found to cause (MCAD) deficiency. Many of these mutations change single amino acids in the MCAD enzyme. The most common change replaces the amino acid lysine with the amino acid glutamic acid at position 304 in the enzyme (Lys304Glu or K304E). This mutation and other amino acid substitutions alter the enzyme's structure, severely reducing or eliminating its activity. Other types of mutations lead to an abnormally small and unstable enzyme that cannot function.

The presence of a mutation c.985A>G in ACADM exon 11 has been linked to affected phenotype in clinical cases (Matern and Rinaldo, Medium-chain acyl-coenzyme A dehydrogenase deficiency, *In: GeneReviews: Genetic Disease Online Reviews* at GeneTests-GeneClinics (database online: Initial posting: Apr. 20, 2000; last update Jan. 27, 2003), 2003.). Additional studies have shown the prevalence of this mutation in populations other than Caucasian is low (Matern and Rinaldo). A large newborn screening study performed by the state of New York showed that affected individuals were less likely to be homozygous for the c.985A>G mutation than they were to have other types of mutations such as large deletions or nonsense mutations (Arnold et al. 2010. Lack of genotype-phenotype correlations and outcome in MCAD deficiency diagnosed by newborn screening in New York State. *Molecular Genetics and Metabolism* 99:263-268). Another large phenotype-genotype study revealed many genetic variants of unknown significance as well as a mutation, c.199T>C in exon 3, that was present in individuals who expressed a milder form of the disease (Smith et al. 2010. Allelic diversity in MCAD deficiency: The biochemical classification of 54 variants identified during 5 years of ACADM sequencing. *Molecular Genetics and Metabolism*. 100(3):241-50. Epub 2010 Apr 8). These findings suggest that genotype confirmation of MCAD deficiency cannot be limited to detection of a single mutation, and a DNA scanning technique would be useful to rapidly canvass the content of the ACADM gene.

Diagnosis of disorders having a genetic linkage, including CF or MCAD deficiency, or the identification of a carrier individual, requires the analysis of the relevant gene to determine whether a known disease-causing mutation is present. Such analysis may also need to consider whether common variants from the wildtype sequence are present that are not disease-causing.

Methods of DNA analysis including amplification via polymerase chain reaction (PCR), including both standard and asymmetric PCR, and high resolution melting analysis (HRMA) are well known in the art. Recent advances have made such analysis methods available on a microfluidic scale. Description of such advances can be found in, for instance, US 2007/0026241, which is incorporated herein in its entirety.

It has previously been shown that the techniques of scanning (using amplification and HRMA to determine whether a mutation is present, without confirmation of the genotype of the mutation) can be utilized in conjunction with genotyping assays to determine whether mutations are present at a subset of known possible mutation sites and if so, what those mutations are (Zhou et al., "High-Resolution DNA Melting Analysis for Simultaneous Mutation Scanning and Genotyping in Solution", Clinical Chemistry 51(10): 1770-1777 (2005)). However, this methodology requires that the reactants contain primers for all potential genotypes being tested, and the feasibility of such a method decreases as the complexity of the gene being tested increases. Genes such as CFTR, which is known to have over 1200 mutations or variants, many of which are not recognized as disease causing, would be particularly unsuited to such a method as there would be a high probability of the scanning portion of the assay determining that a mutation or variant was present, without the ability to genotype the mutation unless it was one of the few specifically being tested for. Particularly in regards to common variants that are not disease causing, this method would be inefficient.

There is a need in the art for methods and systems to allow fast, efficient, accurate and cost-effective genetic analysis of DNA samples in order to determine the presence or absence of mutations in a gene of interest. The present application addresses this need.

SUMMARY OF THE INVENTION

The present invention provides methods and systems for performing gene scanning by PCR amplification and HRMA as a cost and time efficient alternative to sequencing for identifying sequence mutations and/or variants in genes of interest.

In one object of the present invention, there is provided a method of sequentially analyzing a biological sample for the presence or absence of a disease causing mutation or other variant comprising the steps of (a) screening each exon of a gene of interest for the presence or absence of a mutation and/or variant; and (b) confirming the presence of a mutation or variant in an exon found in step (a) by screening that exon for each particular mutation and/or variant known to occur in that specific exon.

In one object of the invention, the screening methods provided herein utilize high resolution melt analysis.

In another object of the invention, the screening methods provided herein are performed in a microfluidic device.

In one object of the present invention, a positive test for a mutation is indicative of a carrier or disease state. It is within the scope of the present invention that the carrier or disease state is cystic fibrosis or medium chain acyl-CoA dehydrogenase deficiency. It is yet a further object of the present invention that a positive result indicating the presence of a mutation is confirmed by a subsequent test prior to the cessation of further testing.

In another object of the present invention, there is provided a method of sequentially analyzing a biological sample for the presence or absence of a disease causing mutation or a common variant comprising the steps of (a) screening each exon for the presence or absence of a mutation or variant; and (b) confirming the presence of a mutation or variant in an exon found in step (a) by screening that exon for each particular mutation or variant known to occur in that specific exon.

In yet another object of the present invention, there is provided a method of analyzing a biological sample for the presence or absence of a genetic mutation in a gene of interest comprising the steps of (a) selecting one or more primers to amplify an exon of the gene of interest and amplifying the exon; (b) performing a thermal melt analysis on the amplified exon; (c) determining whether the thermal melt analysis results of step (b) indicate the presence or absence of a mutation or common variant in the amplified exon; wherein, (i.) if the comparison of step (c) is indicative of the presence of a mutation in the amplified exon, then (1) selecting one or more primers to amplify at least one portion of the exon from step (a), wherein the at least one amplified portion includes the site of one or more known mutations or common variants; (2) amplifying the exon using the primers from step (1); (3) performing a thermal melt analysis on the amplification products of step (2); and (4) determining whether the thermal melt analysis results of step (3) indicate the presence or absence of a mutation or common variant; (ii.) optionally stopping the analysis if a known mutation or common variant is found; and (d) repeating steps (a) through (c) for each exon in the gene of interest, until the earlier of each exon has been amplified and subjected to thermal melt analysis, or the analysis is optionally stopped in step (c)(ii).

In one object of the present invention, the step of determining whether thermal melt analysis results indicate the presence or absence of a mutation in the amplified exon comprises comparing the thermal melt analysis results for the amplified exon with known thermal melt results for wildtype DNA of the amplified region. In another object of the present invention, the step of determining whether thermal melt analysis results indicate the presence or absence of a mutation in the amplified exon comprises comparing the thermal melt analysis results for the amplified exon with known thermal melt results for DNA of the amplified region comprising a homozygous or heterozygous mutation.

In another object of the present invention, the methods and systems described herein can be utilized for scanning a gene of interest wherein the disease or carrier state being tested is cystic fibrosis or medium chain acyl-CoA dehydrogenase deficiency.

Other features, objects, and advantages of the invention will be apparent from the description and drawings, and from the claims.

BRIEF DESCRIPTION OF THE DRAWINGS

The patent or application file contains at least one drawing executed in color. Copies of this patent or patent application publication with color drawing(s) will be provided upon request and payment of the necessary fee.

The following Detailed Description, given by way of example, but not intended to limit the invention to specific embodiments described, may be understood in conjunction with the accompanying drawings, incorporated herein by reference, in which:

FIG. 1 is a chart depicting the ACOG panel of 23 known cystic fibrosis causing mutations.

FIG. 2A-2H are images of the Amplification Curves (Fluorescence vs. Number of Cycles, on the left) and Melting Peaks (–(d/dT) Fluorescence v. Temperature in ° C., on the right) for the CFTR exons.

FIG. 3 is a chart depicting the result of analysis of the amplification curves for the CFTR exons.

FIG. 6A-AA disclose SEQ ID NOS 35-136, respectively, in order of appearance.

FIG. 7A-7G. Images of the scanning assays for all exons of ACADM (12 exons, 13 assays total). Melt curves and difference plots are shown for whole genome amplified samples and genomic DNA samples separately for each exon. Whole genome amplified samples that appear normal in any given assay are colored light green; genomic DNA samples that appear normal in any given assay are colored dark green. All other variants are labeled with a matching color in the relevant plot. From top to bottom, the four plots for each assay are: Normalized and Shifted Melting Curves—Whole Genome Amplifed samples (Relative Signal % vs. Temperature in ° C.); Normalized and Temperature Shifted Difference Plot—Whole Genome Amplified samples (Relative Signal Difference vs. Temperature in ° C.); Normalized and Shifted Melting Curves—genomic DNA samples (Relative Signal % vs. Temperature in ° C.); and, Normalized and Temperature Shifted Difference Plot—genomic DNA samples (Relative Signal Difference vs. Temperature in ° C.).

FIG. 8 are images of the Normalized and Temperature-Sifted Difference Plots (Relative Signal Difference vs. Temperature in ° C.) demonstrating reproducibility of the examples. The top plot of each pair is the results with whole genome amplified samples and the bottom plot is the results using genomic DNA samples.

DETAILED DESCRIPTION OF THE INVENTION

Figure 2A:
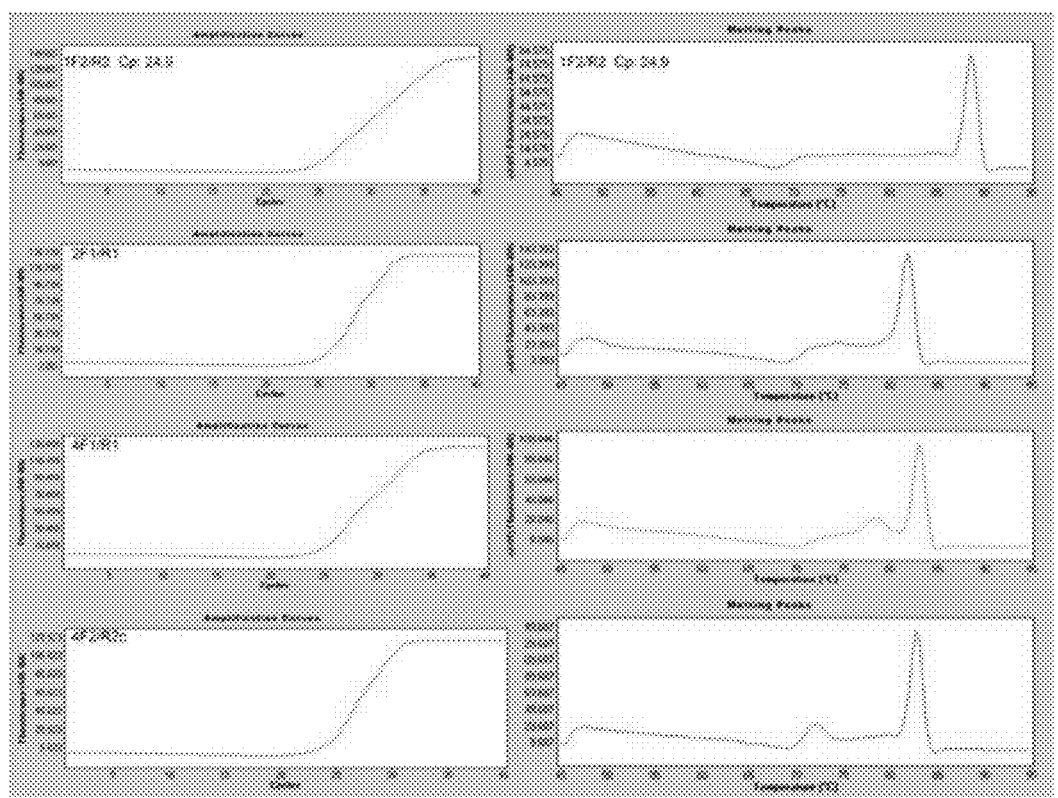
Figure 2B:
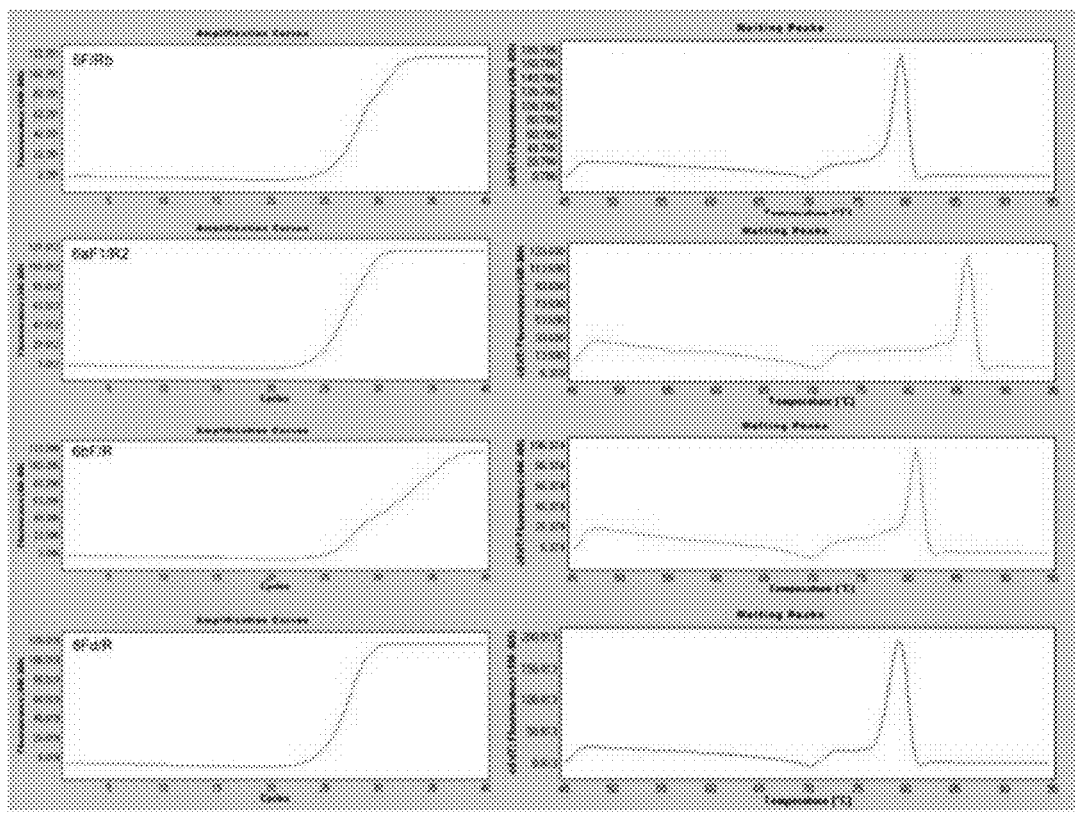
Figure 2C:
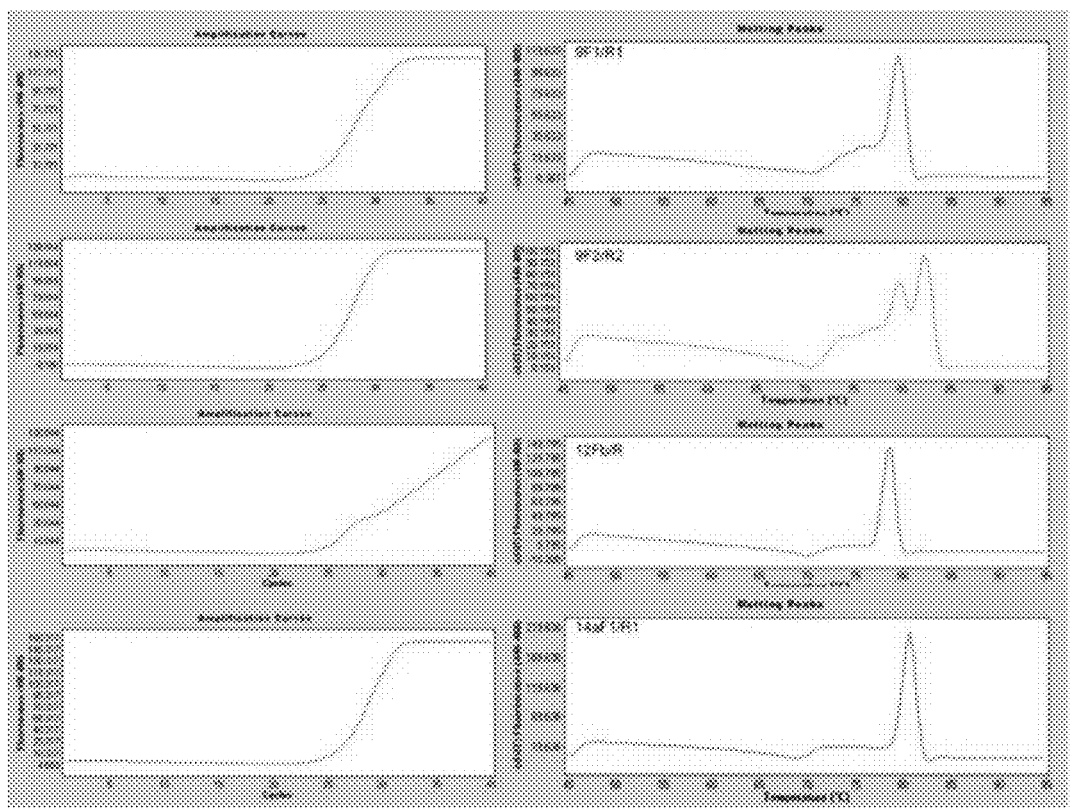
Figure 2D:
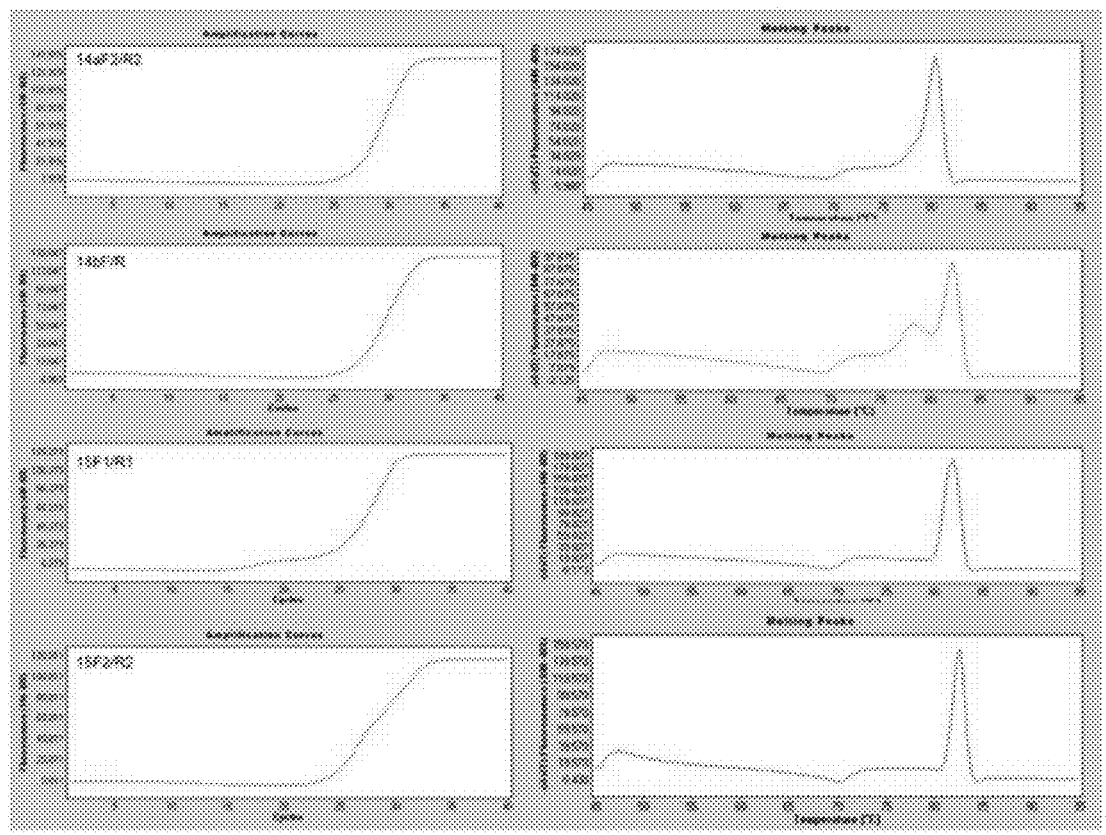
Figure 2E:
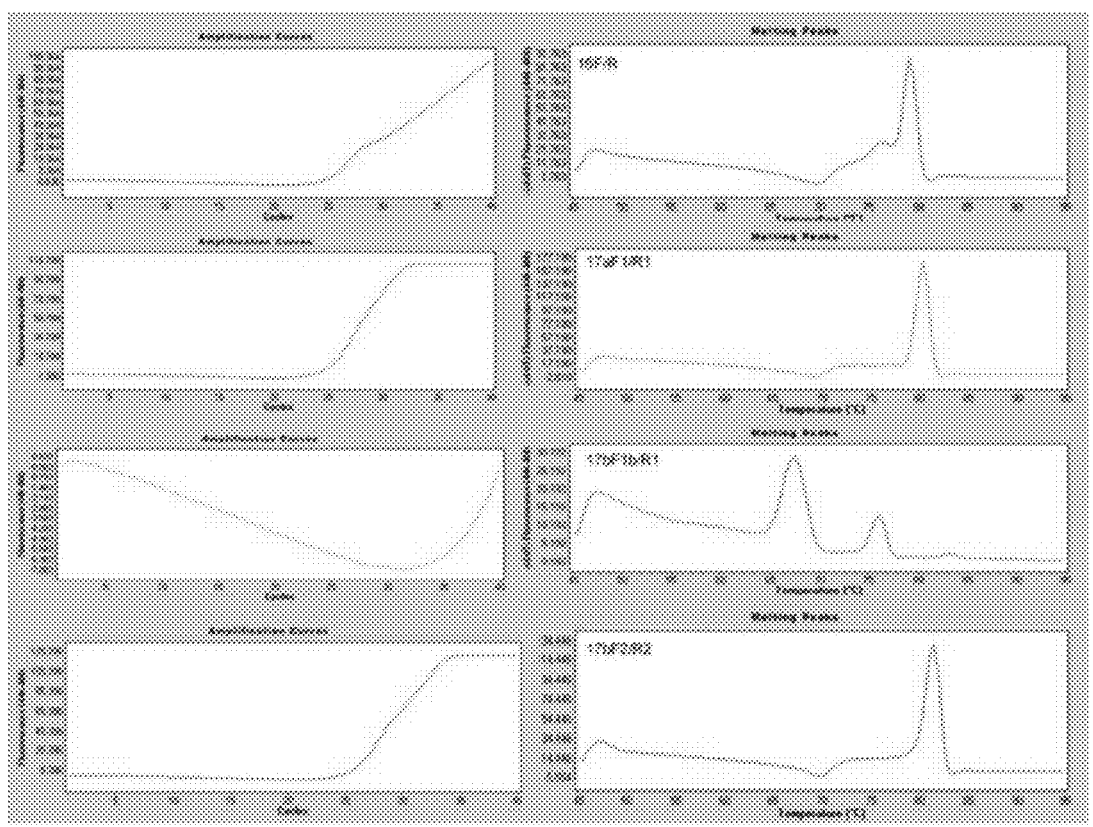
Figure 2F:
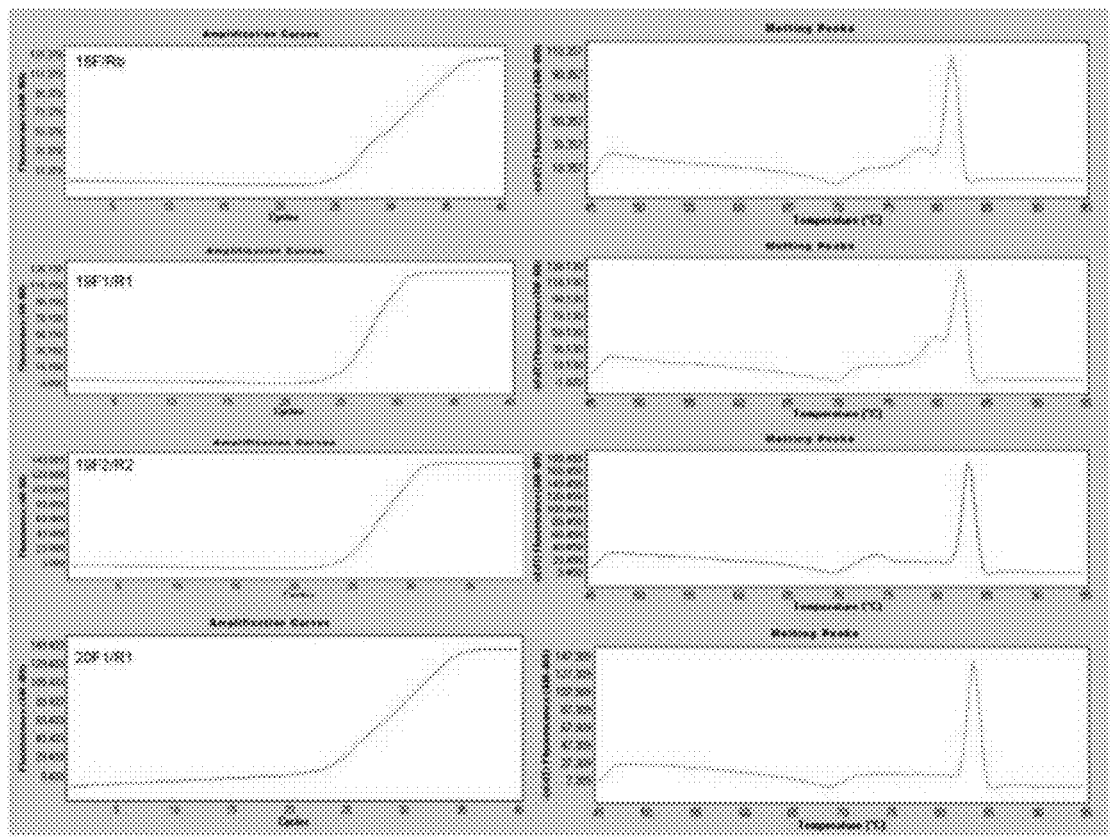
Figure 26:
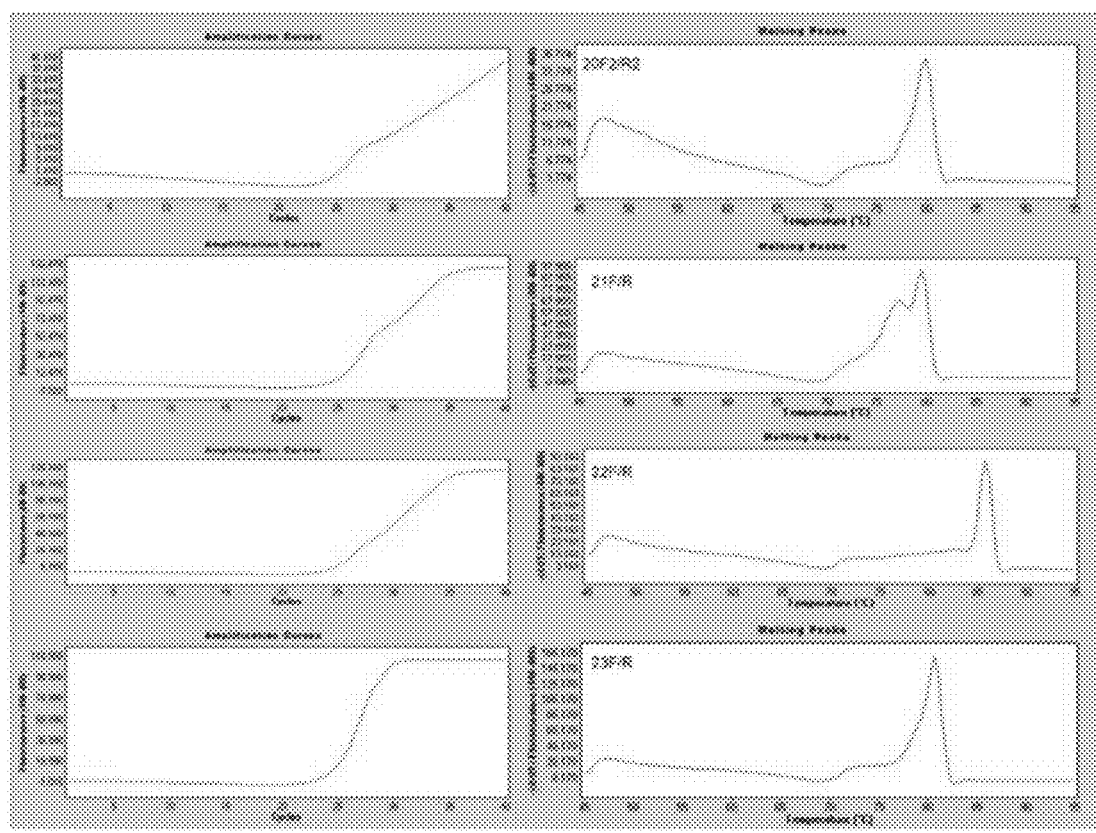
Figure 2H:
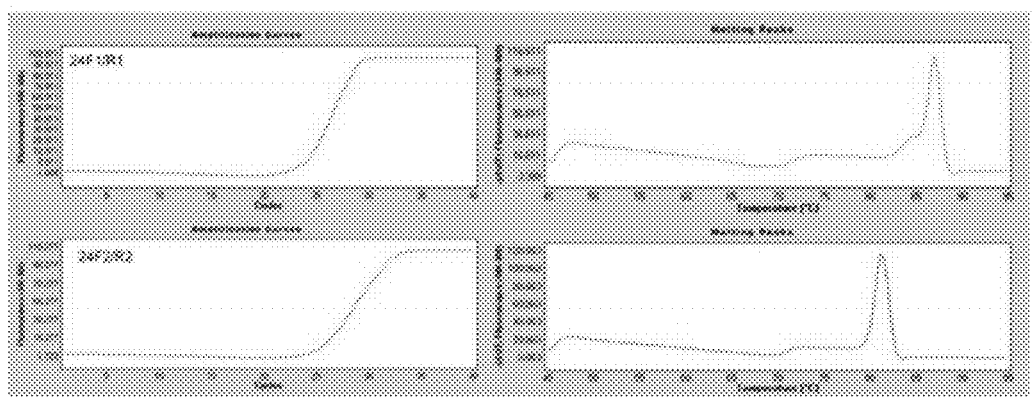
Figure 4A:
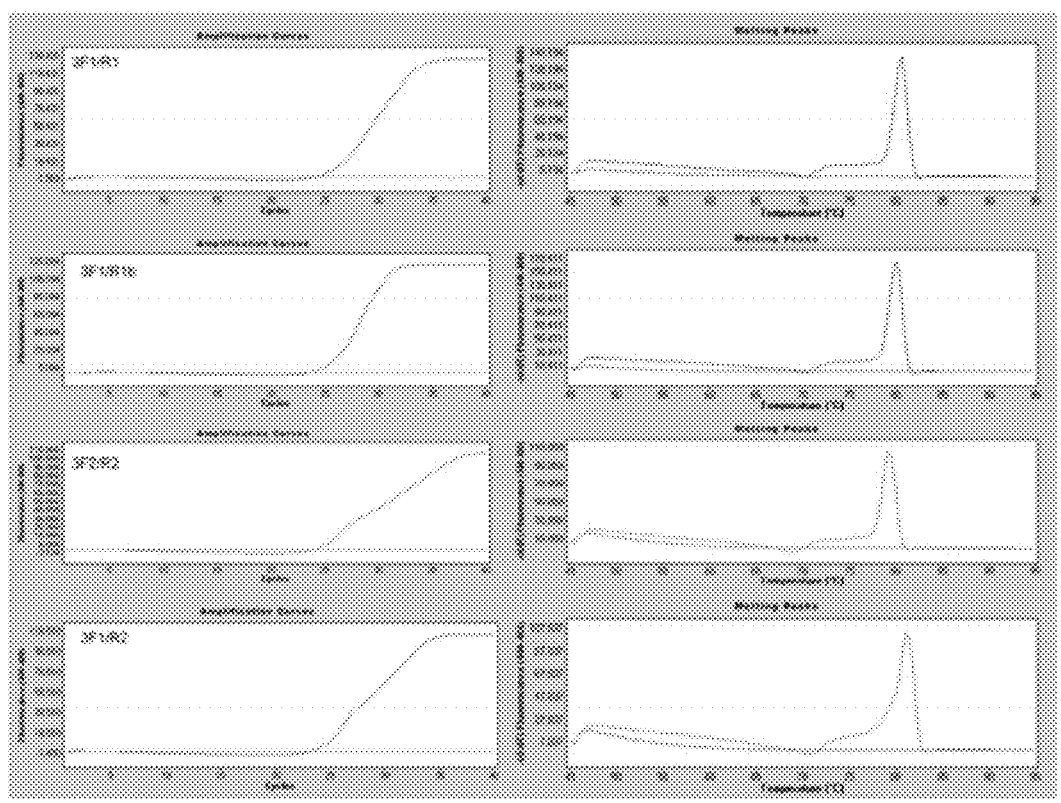
FIG. 4A-4F are images of the Amplification Curves (Fluorescence vs. Number of Cycles, on the left) and Melting Peaks (–(d/dT) Fluorescence v. Temperature in ° C., on the right) for the five CFTR exons used in the blinded study.
Figure 4B:
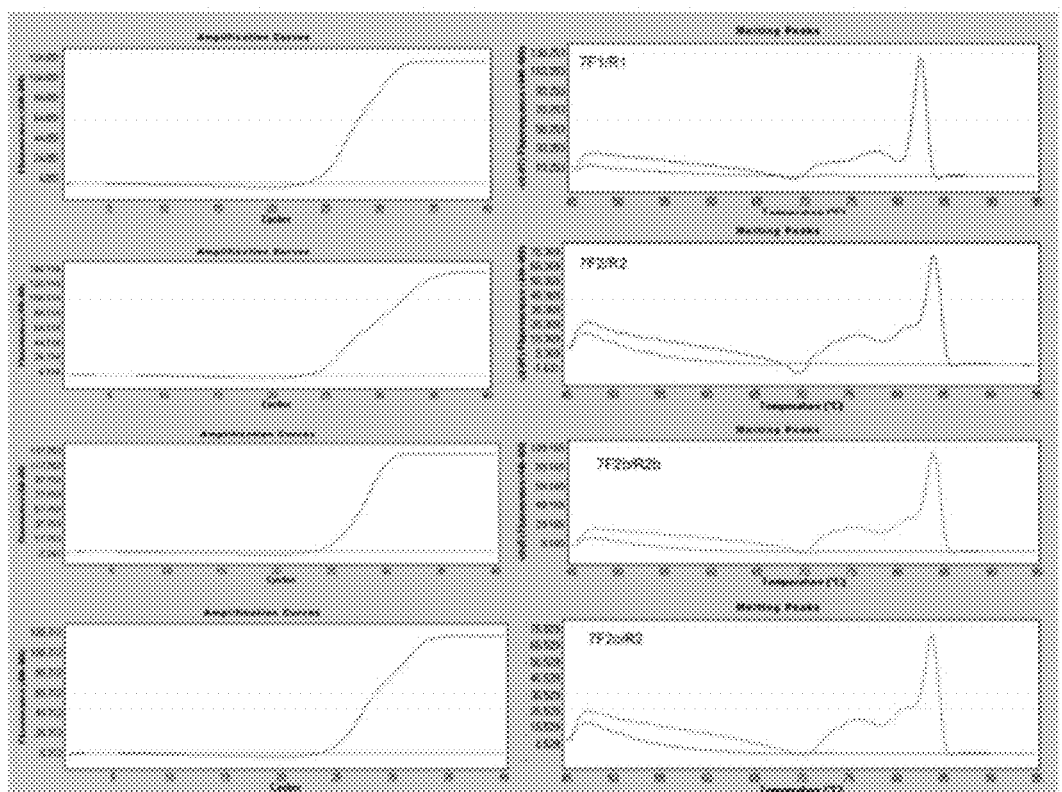
Figure 4C:
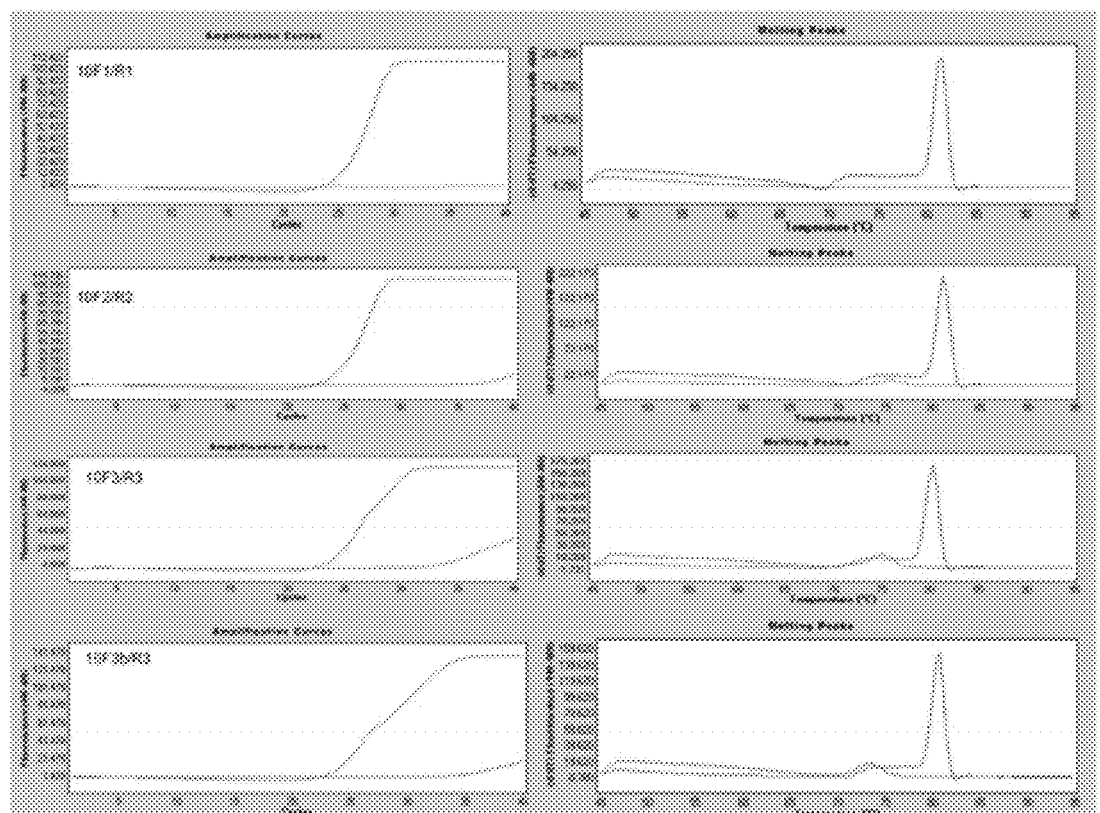
Figure 4D:
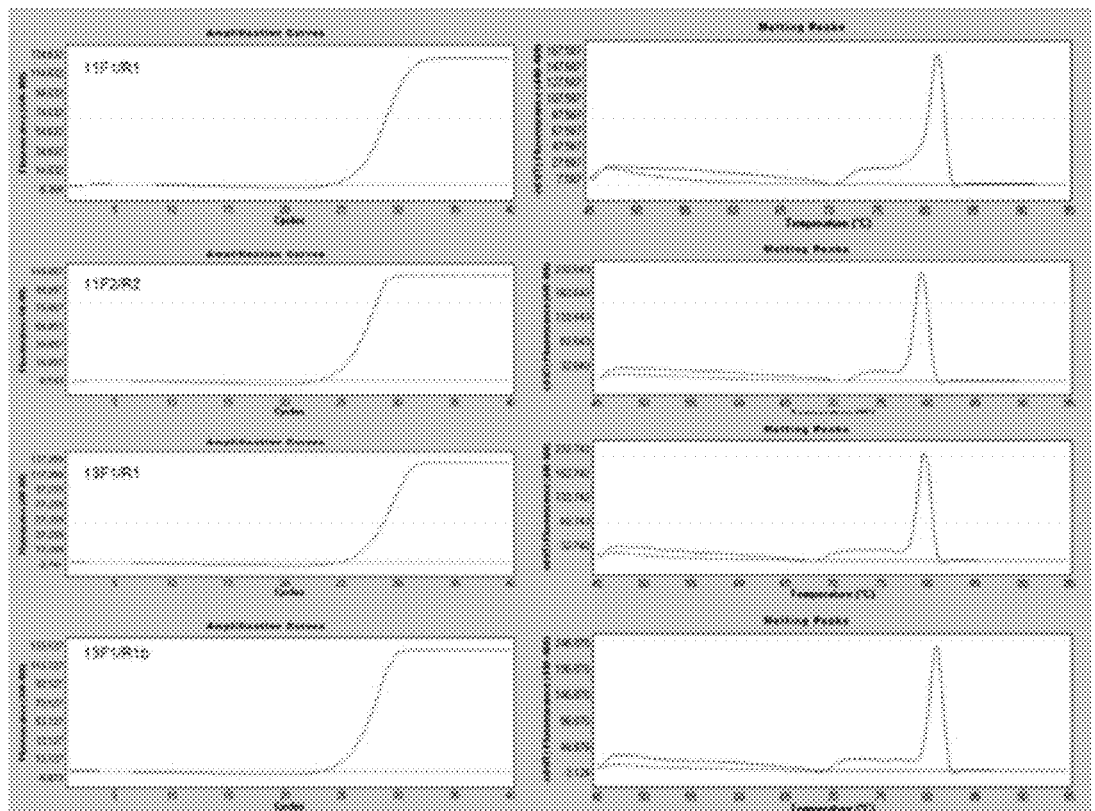
Figure 4E:
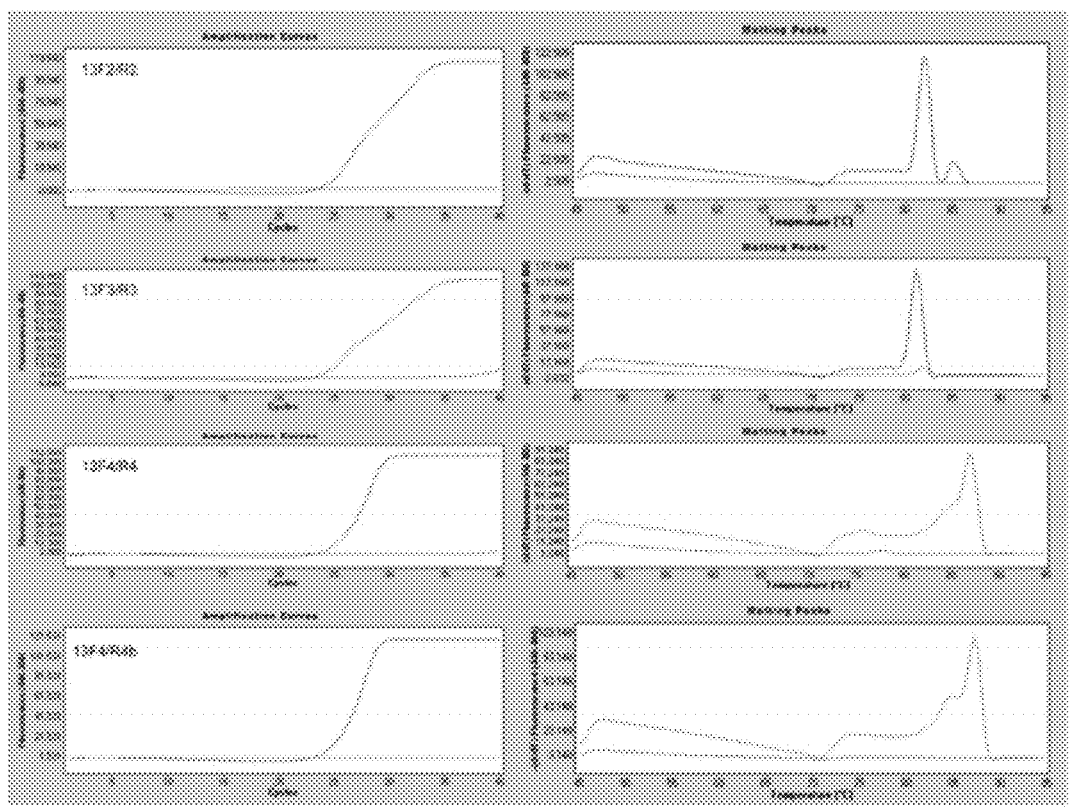
Figure 4F:
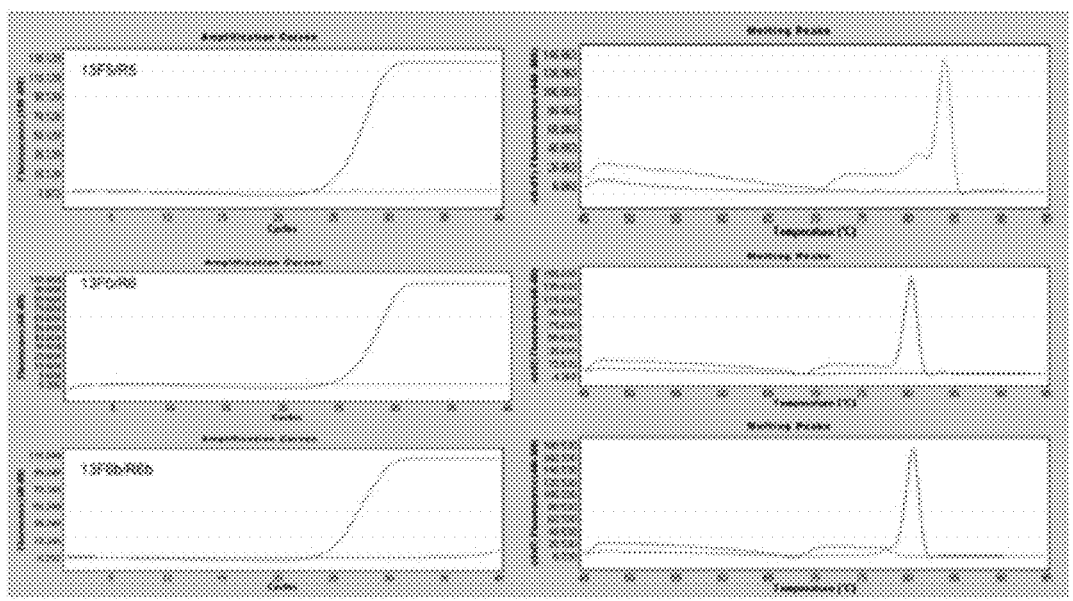

Genome scanning by PCR amplification and HRMA is a cost and time efficient alternative to sequencing for identifying sequence variants. Presented herein is a method to scan all exons of a gene of interest followed by reflexive genotyping assays for confirmation of the presence of mutations of common variants. Specifically, examples are provided herein that demonstrate the application of this method to scanning all 12 exons of the MCAD gene followed by small amplicon genotyping assays for confirmation, and to scanning each of the exons of the CFTR gene, which scanning can be followed by genotyping assays for confirmation.

One embodiment of the present invention is to provide methods and systems for genome scanning using high resolution melting analysis for identifying mutations and/or variants in genes of interest.

Throughout this specification, the term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified", "mutant" or "polymorphic" refers to a gene or gene product which displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically.

The term "target nucleic acid" refers to a nucleic acid molecule containing a sequence that has at least partial complementarity with at least a probe or primer sequence. The target nucleic acid may comprise single- or double-stranded DNA or RNA.

Throughout this application, the term "scan" will be used to mean the amplification of all or part of an exon, followed by HRMA, used to determine whether a mutation or variation is present, without any information regarding the specific genotype of the mutation or variation. "Scanning" may utilize more than one primer pair when desired to reduce the size of the amplification product (i.e., the amplicon). "Genotyping" will be used to mean the amplification of a specific portion of an exon known to contain the location of a possible mutation or variant, followed by HRMA, wherein the testing is performed to positively identify the genotype of the mutation or variant.

In another embodiment of the present invention, there is provided a method of sequentially analyzing a biological sample for the presence or absence of a disease causing mutation or other variant comprising the steps of (a) screening each exon of a gene of interest for the presence or absence of a mutation and/or variant; and (b) confirming the presence of a mutation or variant in an exon found in step (a) by screening that exon for each particular mutation and/or variant known to occur in that specific exon.

In another object of the present invention, there is provided a method of sequentially analyzing a biological sample for the presence or absence of a disease causing mutation or a common variant comprising the steps of (a) screening each exon for the presence or absence of a mutation or variant; and (b) confirming the presence of a mutation or variant in an exon found in step (a) by screening that exon for each particular mutation or variant known to occur in that specific exon.

In yet another object of the present invention, there is provided a method of analyzing a biological sample for the presence or absence of a genetic mutation in a gene of interest comprising the steps of (a) selecting one or more primers to amplify an exon of the gene of interest and amplifying the exon; (b) performing a thermal melt analysis on the amplified exon; (c) determining whether the thermal melt analysis results of step (b) indicate the presence or absence of a mutation or common variant in the amplified exon; wherein, (i.) if the comparison of step (c) is indicative of the presence of a mutation in the amplified exon, then (1) selecting one or more primers to amplify at least one portion of the exon from step (a), wherein the at least one amplified portion includes the site of one or more known mutations or common variants; (2) amplifying the exon using the primers from step (1); (3) performing a thermal melt analysis on the amplification products of step (2); and (4) determining whether the thermal melt analysis results of step (3) indicate the presence or absence of a mutation or common variant; (ii.) optionally stopping the analysis if a known mutation or common variant is found; and (d) repeating steps (a) through (c) for each exon in the gene of interest, until the earlier of each exon has been amplified and subjected to thermal melt analysis, or the analysis is optionally stopped in step (c)(ii).

The methods of the present invention rely on, and are applicable to, any amplification techniques, including polymerase chain reaction, asymmetric polymerase chain reaction, isothermal amplification, and reverse transcriptase PCR (e.g., for screening mRNA) which are known to those of skill in the art. In general, the methods of the present invention include using primer pairs to amplify entire exons of the gene of interest, followed by using primer pairs in specific genotyping assays wherein a portion of an exon that is known to be a site of a mutation or common variant is amplified. In both instances, following amplification, high resolution melt analysis is used to determine the melting temperature (or melting point) of the amplified genetic material. The melting temperature (as shown by a derivative plot of –(d/dT) fluorescence vs. temperature), can then be compared to the melting temperature of a known sample (wildtype, homozygous or heterozygous) in order to determine whether a mutation or other variant is present.

Therefore, it is an embodiment of the present invention that the skilled artisan can select or design one or more appropriate primer pairs to (1) amplify an entire exon of a gene of interest, or (2) to amplify a section of DNA known to contain a common site for a mutation or variant. It is within the scope of the invention that multiple primer pairs may be desired in order to reduce the amplicon size, for instance when amplifying an entire exon. It is also within the scope of the invention that primer pairs may be designed or selection in accordance with any known techniques, and that one of skill in the art will readily recognize and understand the features of a primer pair that would be desirable for the intended section of DNA to be amplified. For instance, it is within the scope of the present invention that primer pairs may be selected or designed to be used in amplification schemes including small amplicon, labeled or unlabelled probe, and snapback primers, utilizing amplification methods such as standard PCR, asymmetric PCR, isothermal amplification or reverse transcriptase PCR. As one embodiment of the present invention relies on the use of HRMA following amplification, it is also within the present invention that primer pairs should be optimized to ensure efficient HRMA. Those of skill in the art will be familiar with methods for such optimizations, including those techniques described in Erali and Wittwer, "High Resolution melting Analysis for Gene Scanning", Methods 2010 April; 50(4): 250-261, the contents of which are incorporated herein in their entirety. Although Erali and Wittwer relates to selection of primers for scanning of exons, the teachings therein are also applicable to the selection of primer pairs for use in the confirmatory genotyping assays utilized in the present invention.

Accordingly, optimization of the PCR or other amplification reaction is also within the scope of the present invention. One of skill in the art will be readily able to optimize the amplification reaction based on factors including the DNA to be amplified, primer pairs, desired amplicon, reaction platform, desired annealing temperature, etc. Inclusion of a fluorescent dye in the amplification reactants is necessary to allow the amplification products to undergo HRMA, and the modification of the amplification reactants to include such a dye is within the capabilities of one of skill in the art. Therefore, in general, the practice of the present invention will employ, unless otherwise indicated, conventional techniques of molecular biology, which are within the skill of the art. Such techniques are explained fully in the literature. See, e.g., Sambrook, Fritsch & Maniatis, Molecular Cloning: A Laboratory Manual, Vols. I, II and III, Second Edition (1989); DNA Cloning, Vols. I and II (D. N. Glover ed. 1985); Oligonucleotide Synthesis (M. J. Gait ed. 1984); and, Nucleic Acid Hybridization (B. D. Hames & S. J. Higgins eds. 1984).

In another embodiment of the present invention, HRMA is utilized to determine the presence or absence of a mutation or other variant in an exon that has been subjected to a scanning assay or to an amplicon that has been subjected to a genotyping assay. HRMA is a technique well known to those of skill in the art, which is based on the inherent property of DNA to dissociate from a double stranded molecule into a single stranded molecule at the melting temperature ($T_m$). Information on HRMA can be found in the literature, including at Lyon and Wittwer, "LightCycler Technology in Molecular Diagnostics", J. Mol. Diagn. 2009 March; 11(2):93-101, and U.S. Pat. No. 5,871,908 granted Feb. 15, 1999 to Henco et al. The inclusion of a fluorescent dye in the amplification reactants ensures that the target DNA will contain fluorescent dye within the double stranded helix, such that when the target DNA is subjected to a temperature gradient, it is possible to monitor the dissociation of the target DNA into single stranded molecules by observing the fluorescence emitted during the temperature gradient (or, the thermal melt). One of skill in the art will be readily able to optimize the HRMA conditions based on the platform being utilized for the reaction, including optimizing the rate at which the temperature ramp occurs.

As described above, the HRMA utilized herein requires the detecting a level of fluorescence or emitted light from the molecule(s) that varies as a function of relative amounts of binding. In addition to the situation described above, wherein a dye is introduced into the amplification reagents, it is also an embodiment of the present invention that in one configuration, the detecting of fluorescence involves a first molecule and a second molecule, wherein the first molecule is a fluorescence indicator dye or a fluorescence indicator molecule and the second molecule is the target molecule to be assayed. In one embodiment, the fluorescence indicator dye or fluorescence indicator molecule binds or associates with the second molecule by binding to hydrophobic or hydrophilic residues on the second molecule. The methods of detecting optionally further comprise exciting the fluorescence indicator dye or fluorescence indicator molecule to create an excited fluorescence indicator dye or excited fluorescence indicator molecule and discerning and measuring an emission or quenching event of the excited fluorescence indicator dye or fluorescence indicator molecule. In one embodiment, the second molecule is the amplified exon or amplicon that is to undergo scanning and/or genotyping assays.

In addition, or separate from, fluorescence or emitted light detection as described above, detecting a property of the molecule(s) being assayed may optionally comprise the use of, e.g., fluorescence spectroscopy involving, e.g., fluorescence polarization, fluorescence resonance energy transfer (FRET), fluorescence lifetime imaging microscopy, molecular beacons, fluorescence correlation spectroscopy (FCS), circular dichroism, or the like. Similarly, a change in the thermal parameters of a system involving the molecule(s) can be monitored. Yet another method of detecting a property of the molecule(s) being assayed comprises monitoring the UV absorbance of the molecule(s).

As described above, an additional embodiment of generating thermal property curve as part of the HRMA comprises measuring a change in the fluorescence of one molecule that is correlative or proportional to a change in a physical property of another molecule(s) due to a change in temperature. A further embodiment includes generating a thermal property curve control curve by measuring fluorescence of a first molecule in the presence of a second molecule as a function of temperature, where the first molecule is a fluorescence indicator dye or molecule and the second molecule is: a protein, a polypeptide, an enzyme, an enzyme complex, a nucleic acid (either single-stranded or double-stranded), a ligand, a peptide nucleic acid, a cofactor, a receptor, an antibody, an antigen, or a substrate. In one embodiment, the second molecule is the amplified exon or amplicon that is to undergo scanning and/or genotyping assays. Other methods of monitoring dissocation of a DNA molecule from double stranded to single stranded are known to those of skill in the art and can be equally employed in the methods and systems of the present invention.

It is an embodiment of the present invention that the techniques utilized here can be used for carrier screening or diagnosis of any disease or disorder wherein more than a single mutation is causative of the disorder or disease. In general, the methodology includes: (a) providing one or more primer pairs to allow amplification of each exon of the gene, (b) amplifying each exon and performing high resolution melting analysis (HRMA) on the amplified exon, (c) comparing the HRMA of the amplified exon with a control HRMA, wherein a deviation from the control HRMA is indicative of the presence of a mutation (d), providing one or more primer pairs to amplify each section of an exon containing the location of a known disease-causing mutation, (e) amplifying each known mutation location and performing HRMA on the amplification product, (f) comparing the HRMA of the amplification product with a control HRMA, wherein a deviation from the control is indicative of the presence of a mutation (where the control HRMA is from wildtype DNA) or wherein a match with the control is indicative of the presence of a mutation (where the control HRMA is from a mutation containing sample).

In a further embodiment, specific portions of exons can be analyzed to determine whether common, non-disease-causing variants are present. This can be done in addition to, in combination with, or in lieu of, determining whether a disease-causing mutation is present, as described above and herein. Analysis of a sample for common variants can similarly be accomplished via providing one or more primer pairs to amplify each section of an exon containing the location of a known common variant, (a) amplifying each known variant location and performing HRMA on the amplification product, (b) comparing the HRMA of the amplified location with a control HRMA, wherein a deviation from the control is indicative of the presence of a variant (where the control HRMA is from wildtype DNA) or wherein a match with the control is indicative of the presence of a variant (where the control HRMA is from a variant-containing sample).

It is within the scope of the invention that such methodology can be repeated in a manner appropriate for each individual disease or disorder, based upon the number of exons to be scanned, and the number of known mutations and/or variants found in each exon. It is within the scope of the present invention that all of the exons could first be scanned followed by further genotyping of only those exons showing a positive result for a mutation and/or variant in order to identify the particular mutation and/or variant. Alternatively, the exons can be scanned sequentially, with a positive result for a mutation and/or variant preventing the scanning of another exon and instead causing a genotyping analysis to be performed to identify the mutation and/or variant. If no mutation or variant is found, another exon could then be scanned. If a mutation or variant is found, the testing could end or, the testing could continue with the next exon if so desired. The order in which exons are scanned can be altered depending on the likelihood of the presence of a mutation, the number of common variants, etc. One of skill in the art would be able to determine an order for the exons to be scanned that would provide efficient results without requiring that the exons be scanned in any particular order (for instance, the order in which they are located may not be a desirable order in which the exons should be scanned).

It is a further embodiment of the present invention that successive iterations of this methodology can be utilized. For instance, multiple exons could first be scanned together, followed by individual exons being scanned if the joint exon scan indicated a mutation or variant was present. Alternatively or in addition, upon confirming the presence of a single mutation or variant, the testing could be ended, particularly in those instances where a single mutation is sufficient to indicate a disease or carrier state.

It is also within the scope of the present invention that the order in which the exons are scanned, or that the order in which individual mutations or variants are analyzed, is determined based on population frequency; in utilizing population frequency, those exons that have a higher percentage of mutations or variants can be scanned first (or before exons having a lower population frequency of mutations and variants), or genotyping for specific mutations or variants having high population frequency are tested first (or before genotyping assays for mutations and variants having a lower population frequency). It is another facet of the invention that genotyping for individual mutations or variants could be performed prior to scanning exons, particularly where a defined number of mutations are known to cause a majority of the incidences of a disease in a given population, or where a particular variant is known to be prevalent in a given population.

Thus, in one embodiment of the present invention, there is provided a method of determining whether a mutation or variant is present in a gene comprising combining scanning exons and genotyping assays for particular mutations. In a further embodiment, the methods of the present invention may include one or more of the following steps, the order of which can be altered as desired based on the particular features of the gene of interest:

A. Scan individual exon;
B. Scan multiple exons;
C. Genotyping assay to confirm presence of mutation or variant following scan of individual exon;
D. Genotyping assay to confirm presence of mutation or variant following scan of multiple exons;
E. Genotyping assay to confirm presence of mutation or variant based on population frequency of the mutation or variant; and
F. Genotyping assay to confirm presence of select mutation(s) or variant(s) based on population frequency within a given ethnicity.
G. Genotyping assay to confirm presence of disease causing mutation, followed by genotyping assay of common variant if no disease causing mutation is found.

In a further embodiment, examples of the reflexive assays that are within the scope of the present application include:

Option I
(1) Scan individual exon
(a) if HRMA indicates mutation or variant is present, then Genotyping assay to confirm presence of mutation or variant following scan of individual exon
   (i) stop if mutation found
   (ii) if no mutation found, then repeat step (1) with next exon
(b) if HRMA indicates no mutation or variant present, then repeat step (1) with next exon (2) following completion of scanning of all exons, if no mutation or variant is indicated, then test result is negative for the presence of mutations in the gene of interest.

Option II
(1) Scan individual exon
(a) HRMA indicates mutation or variant is present,
   (i) genotyping assay for disease-causing mutation If negative, then test for common variant
   (ii) stop if mutation found
   (iii) if no mutation found or common variant found, then repeat step (1) with next exon
(b) if HRMA indicates no mutation or variant present, then repeat step (1) with next exon
(2) following completion of scanning of all exons, if no mutation or variant is indicated, then test result is negative for the presence of mutations in the gene of interest.

Option III
(1) Scan all exons, either sequentially or together
(a) if HRMA indicates mutation or variant is present, then Genotyping assay(s) to confirm presence of mutation or variant for the indicated exon(s)
(b) if no mutation or variant is indicated, then test result is negative for the presence of mutations in the gene of interest.

Option IV
(1) Genotyping assay for one or more of the mutations having a high population frequency;
(a) if mutation is found, stopping test where a single mutation is sufficient to give rise to a finding of the sample being a carrier or having a disease/disorder;
(b) if no mutation is found, continuing to step (2);
(2) Scan individual exon
(a) if HRMA indicates mutation or variant is present, then Genotyping assay to confirm presence of mutation or variant following scan of individual exon
   (i) stop if mutation found
   (ii) if no mutation found, then repeat step (2) with next exon
(b) if HRMA indicates no mutation or variant present, then repeat step (2) with next exon
(3) following completion of scanning of all exons, if no mutation or variant is indicated, then test result is negative for the presence of mutations in the gene of interest.

Option V
(1) Genotyping assay for one or more of the mutations having a high population frequency;
(a) if mutation is found, stopping test where a single mutation is sufficient to give rise to a finding of the sample being a carrier or having a disease/disorder;
(b) if no mutation is found, continuing to step (2);
(2) Genotyping for 1-10 individual mutations or variants based on population frequency determined for the sample's ethnicity;
(a) if mutation is found, stopping test where a single mutation is sufficient to give rise to a finding of the sample being a carrier or having a disease/disorder;
(b) if no mutation is found, continuing to step (3);
(3) Scan individual exon
(a) if HRMA indicates mutation or variant is present, then Genotyping assay to confirm presence of mutation or variant following scan of individual exon
   (i) stop if mutation found
   (ii) if no mutation found, then repeat step (3) with next exon
(b) if HRMA indicates no mutation or variant present, then repeat step (3) with next exon (4) following completion of scanning of all exons, if no mutation or variant is indicated, then test result is negative for the presence of mutations in the gene of interest.

For the purposes of the present invention, it is contemplated that any of Options I-V described above may be added to, altered, combined, or may have steps removed based on the particular characteristics of the gene of interest that will be the subject of the testing. For instance, genes that have a small number of known mutations in a few exons may be more suitable to scanning multiple exons at single time than a gene that is known to have multiple mutation sites in the majority of the exons. Similarly, if the incidence of disease-causing mutations for a gene varies greatly over different ethnicities, such a gene would be a good candidate for a series of genotyping panels, wherein specific mutations or variants were grouped by their frequency in a given ethnicity. Based on the ethnicity of a sample, the respective genotyping panel could be the first test run, followed by scanning of exons if no mutation or variant is detected. In another embodiment, it is within the scope of the present application that a gene which is known to have only a small number of potential mutation or variant sites may only have those particular exons scanned where the potential mutation or variation sites are found. It may not be necessary or desirable to scan exons which are not known as having any potential sites for mutations or variants. Alternatively, the proposed reflexive assays herein can be altered to reflect any clinical diagnostic algorithm for a genetic disease or disorder.

In one example of an embodiment according to the present invention, the main disease-causing mutation of the CFTR gene is the F508del homozygote. Therefore, a biological sample can be analyzed for the presence or absence of a cystic fibrosis causing mutation, where a positive test for a mutation results in discontinuing further testing, and where a negative test for a mutation is followed by the next sequential test for further mutations, comprising the steps of (a) screening said sample for the F508del homozygote (b) screening said sample for a predetermined panel of population-based mutations determined by the subject's ethnicity; and, (c) screening said sample for mutations in each exon of the CFTR gene, wherein each exon is scanned sequentially based on the population frequency of CF-causing mutations found in each exon, wherein the exons are scanned in order from the highest to lowest population frequency, wherein a positive test for a mutation in a particular exon is confirmed by testing the sample for each of the specific mutations found in that exon; and wherein a negative test for a mutation in a particular exon is followed by scanning the next sequential exon.

In a further embodiment, the testing can be arranged such that all exons are tested, or that only a subset of exons are tested based on criteria including population frequency of mutations in those exons. Similarly, genotyping to confirm individual mutations or common variants can be performed for all known mutations/variants or for a subset of known mutations and/or variants selected on the basis of criteria including population frequency of the individual mutations and variants.

In one object of the present invention, a positive test for a mutation is indicative of a carrier or disease state. It is within the scope of the present invention that the carrier or disease state is cystic fibrosis or medium chain acyl-CoA dehydrogenase deficiency. It is yet a further object of the present invention that a positive result indicating the presence of a mutation is confirmed by a subsequent test prior to the cessation of further testing.

In one object of the present invention, the step of determining whether thermal melt analysis results indicate the presence or absence of a mutation in the amplified exon comprises comparing the thermal melt analysis results for the amplified exon with known thermal melt results for wildtype DNA of the amplified region. In another object of the present invention, the step of determining whether thermal melt analysis results indicate the presence or absence of a mutation in the amplified exon comprises comparing the thermal melt analysis results for the amplified exon with known thermal melt results for DNA of the amplified region comprising a homozygous or heterozygous mutation.

In yet another embodiment of the present invention, the genetic testing can be automatically reflexive, whereby the platform on which the testing is run will select the next test, move on to another exon, do a genetoyping assay for confirmation, stop testing, etc., based on a provided script that takes into account the gene being tested, the number and location of potential mutations or variants, the population frequency of the potential mutations or variants, including population frequency across various ethnicities, the ethnicity of the sample, etc. Such reflexive testing will allow the practitioner to select a disorder or disease to test for, provide information regarding the subject, and will cause the platform to carry out each successive stage of the testing until such time as a positive or negative result has been obtained.

In a further embodiment of the present invention, the genetic testing may be carried out on a microfluidic platform, including that which has been developed by Canon U.S. Life Sciences, such as is described in United States Published Patent Application No. 2007/0026421, which is incorporated herein in its entirety. In one embodiment, the reflexive genetic testing described herein can be performed on a system comprising a microfluidic device, which refers to a device having fluidic channels or chambers that are generally fabricated at the micron to sub-micron scale, e.g., the channel or chamber typically having at least one cross-sectional dimension in the range of less than about 1 mm. The channels in a microfluidic device are sometimes referred to as "microfluidic channels".

The reflexive genetic testing of the present invention can therefore be carried out on a microfluidic system comprising a microfluidic device having body structure containing at least one fluidic microchannel; a fluid direction system for controllably moving reagents into and through the microchannel; at least one energy source for controllably heating the reagents in the microchannel; a source of a fluorescence indicator dye or fluorescence indicator molecule fluidly coupled to the microchannel; a source of one or more sample molecules to be assayed fluidly coupled to the microchannel; an excitation source for the fluorescence indicator dye or fluorescence indicator molecule; a detector proximal to the body structure for detecting a change in a physical property of the one or more sample molecules; and, a computer operably coupled to the detector, containing an instruction set for acquiring data from the detector and for constructing thermal melt curves and control curves from the data.

In another embodiment, the integrated system or microfluidic devices of the invention include a fluid direction system which, during operation, controllably determines the selection of one or more reagent(s) to be added to the microchannel; the amount of one or more reagent(s) to be added to the microchannel; the time at which one or more reagent(s) is to be added to the microchannel; and the speed at which one or more reagent(s) is to be added to the microchannel.

In another embodiment, the integrated system or microfluidic devices of the invention include at least one energy source which, during operation, elevates the temperature of the molecule(s) in the microchannel by either joule heating, non-joule heating or both joule heating and non-joule heating.

EXAMPLES

The present invention is described by reference to the following Examples, which are offered by way of illustration and are not intended to limit the invention in any manner. Standard techniques well known in the art or the techniques specifically described below were utilized.

1. Cystic Fibrosis Screening

Materials and Methods

Figure 6A:
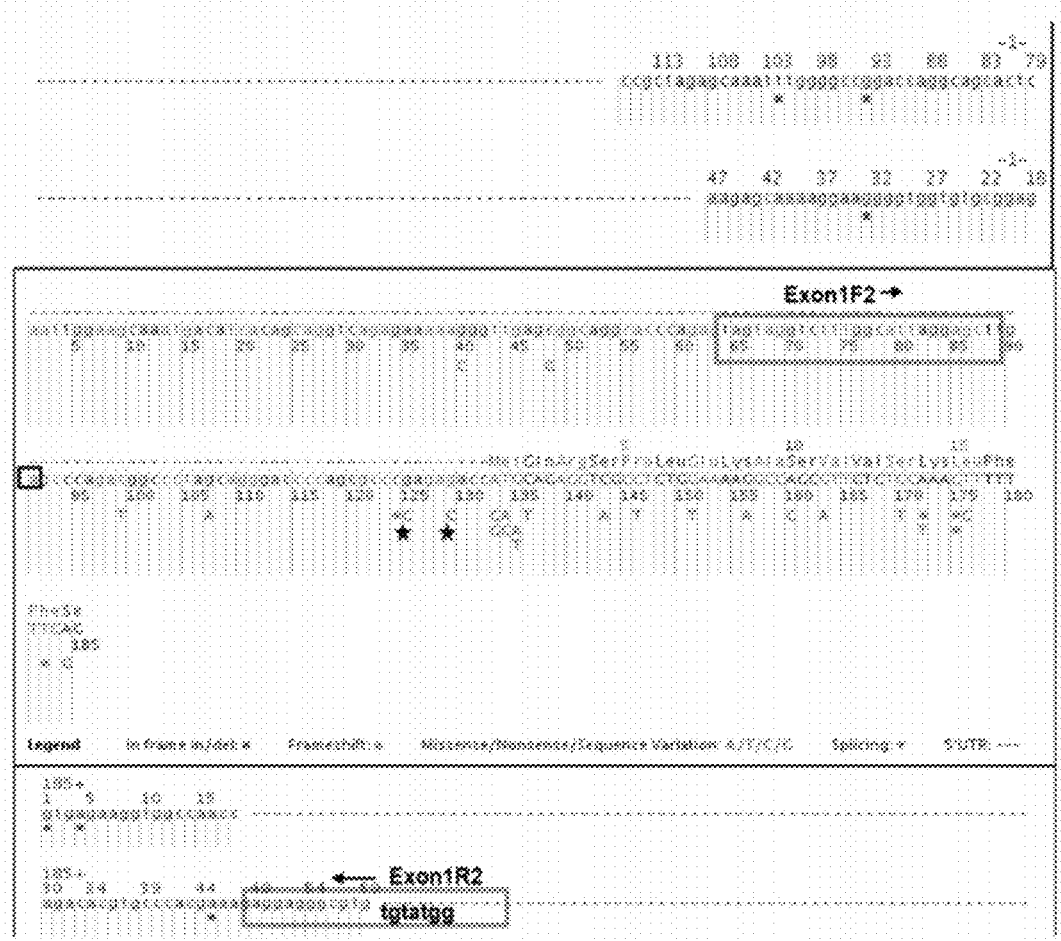
FIG. 6A-AA are charts depicting the placement of the scanning primers in the CFTR exons.
Figure 6B:
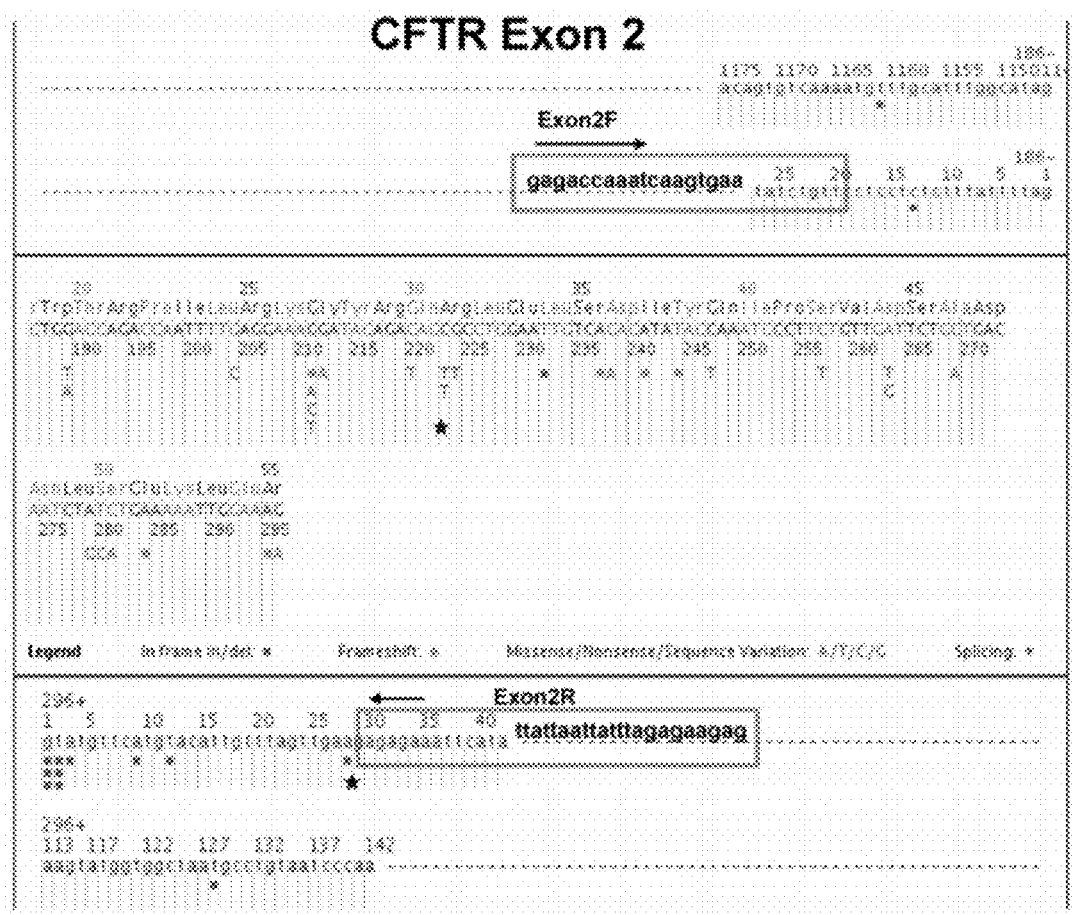
Figure 6C:
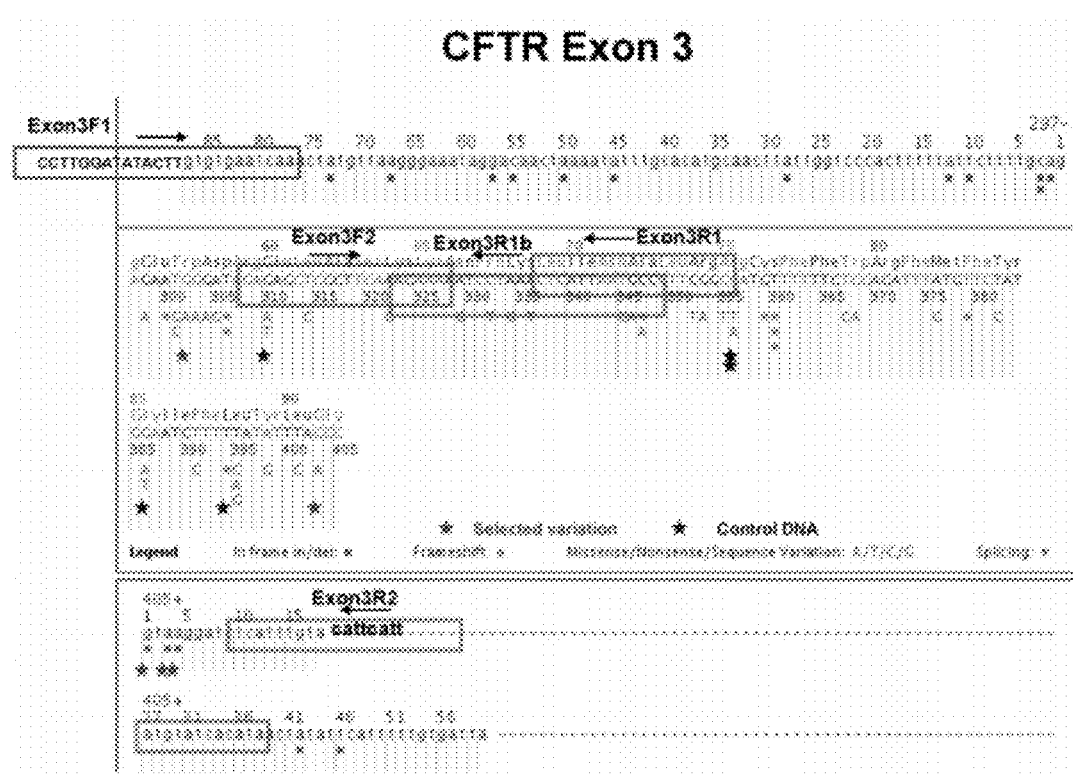
Figure 6D:
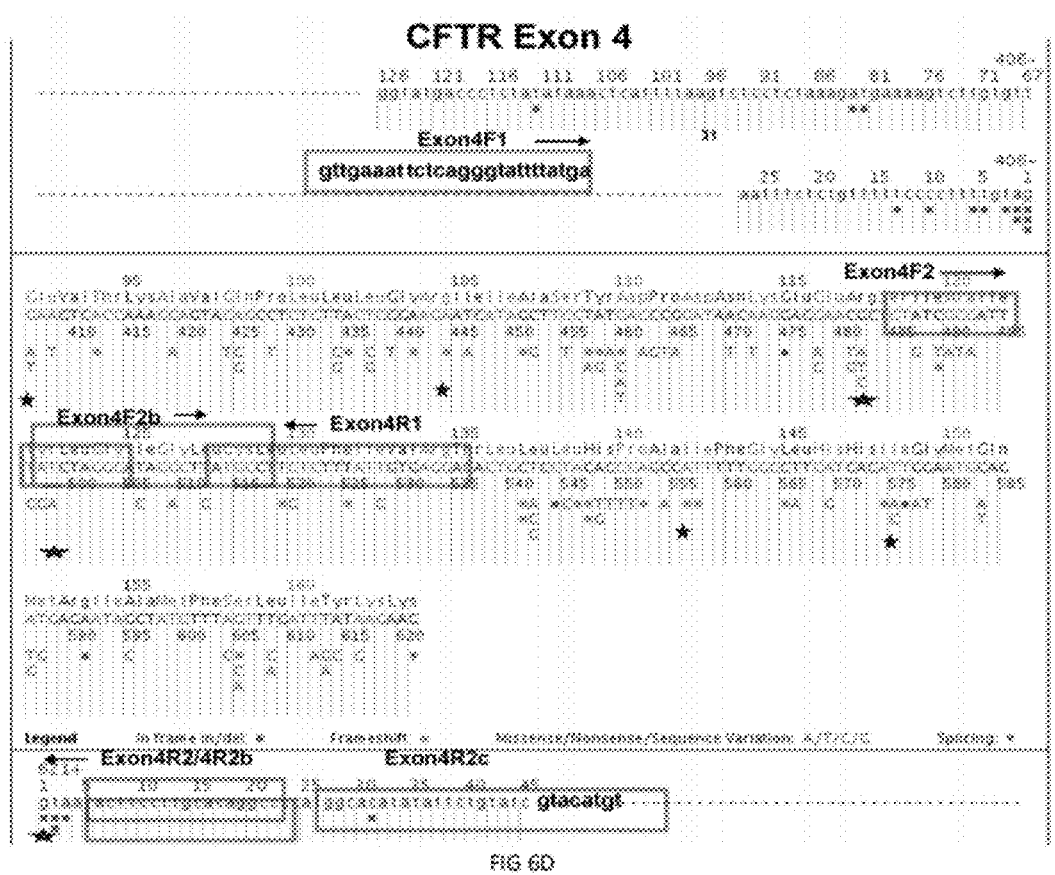
Figure 6E:
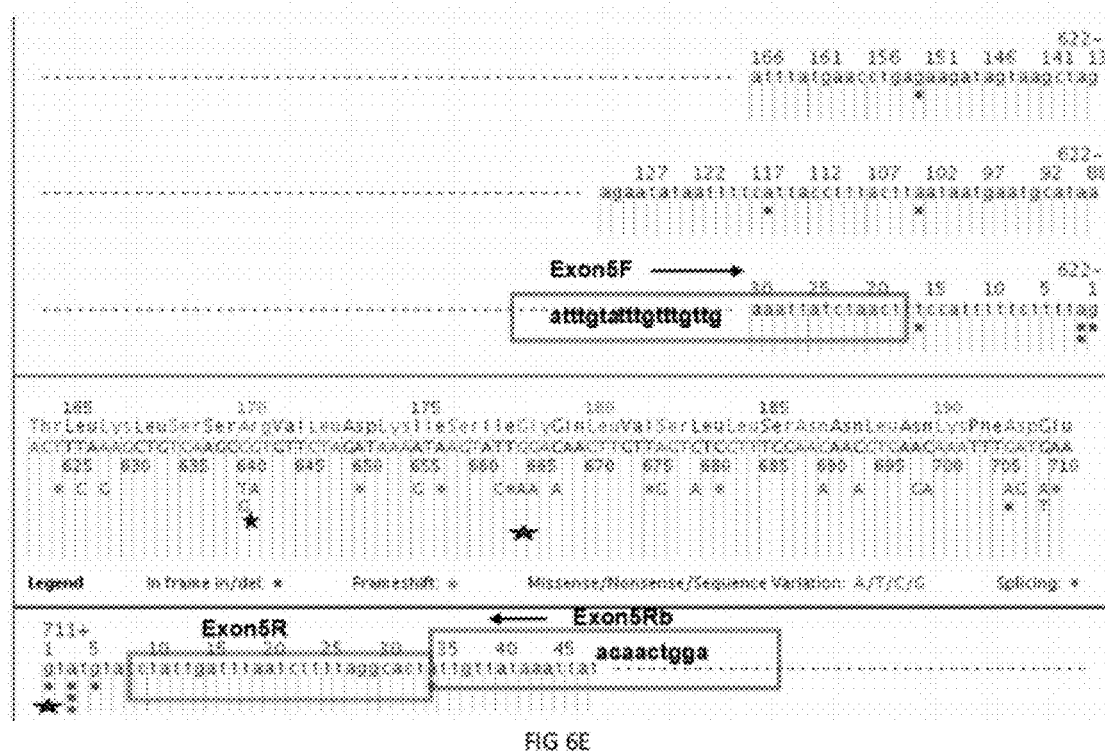
Figure 6F:
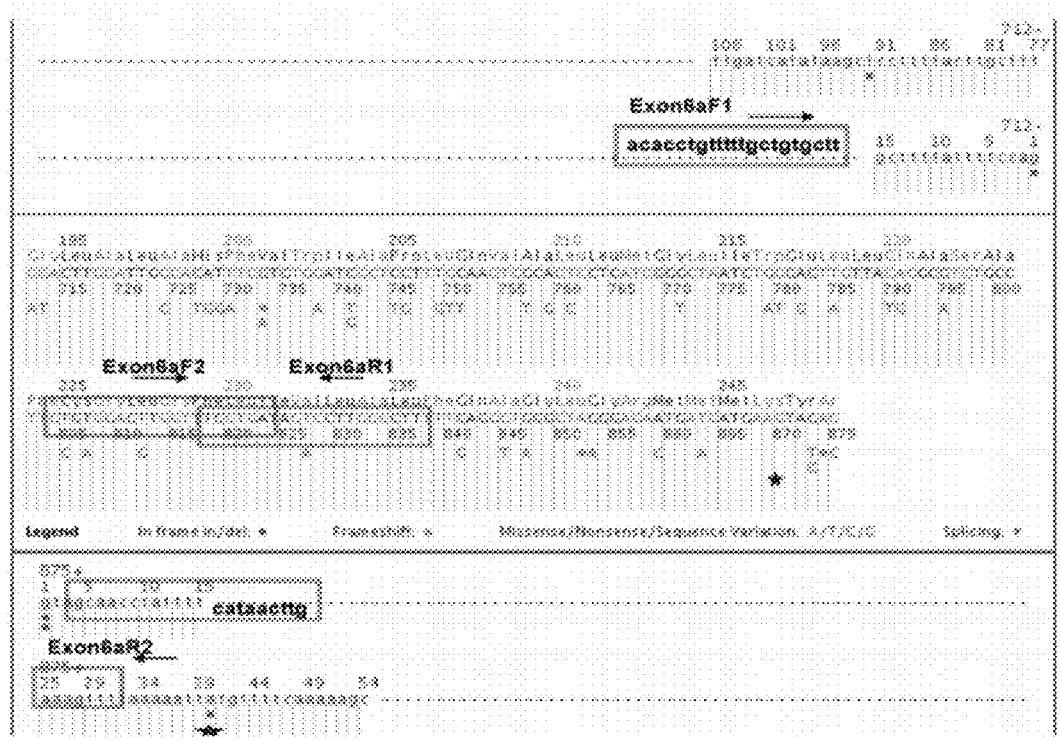
Figure 6G:
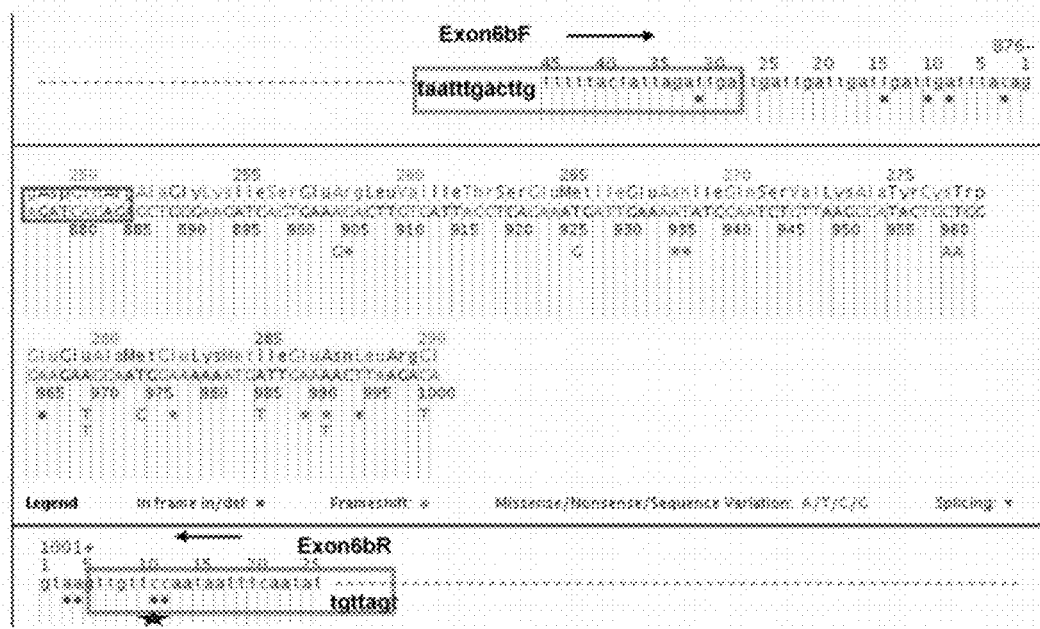
Figure 6H:
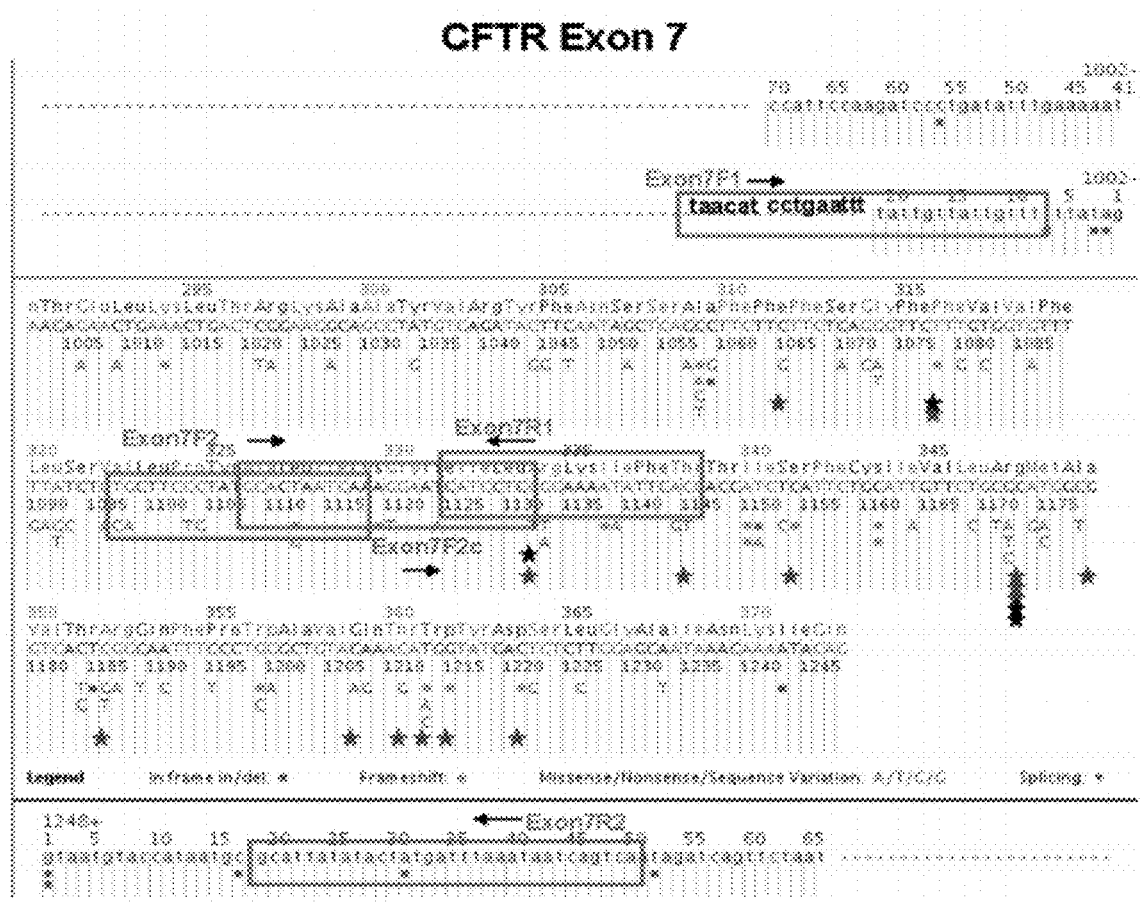
Figure 6I:
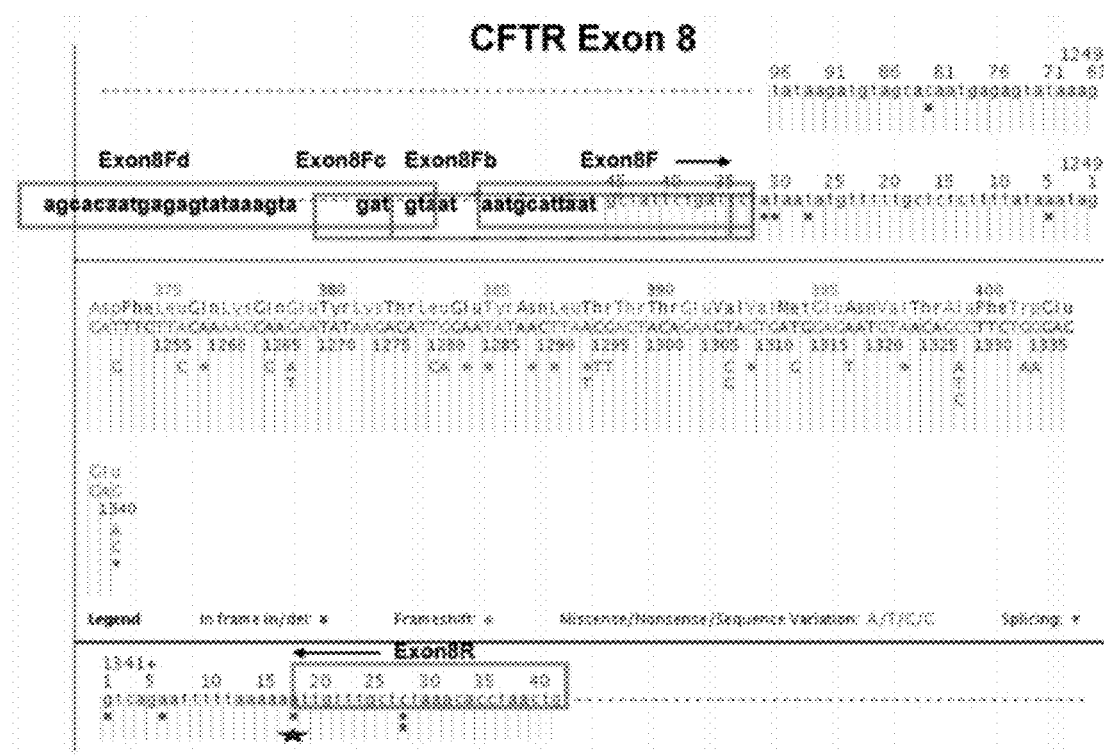
Figure 6J:
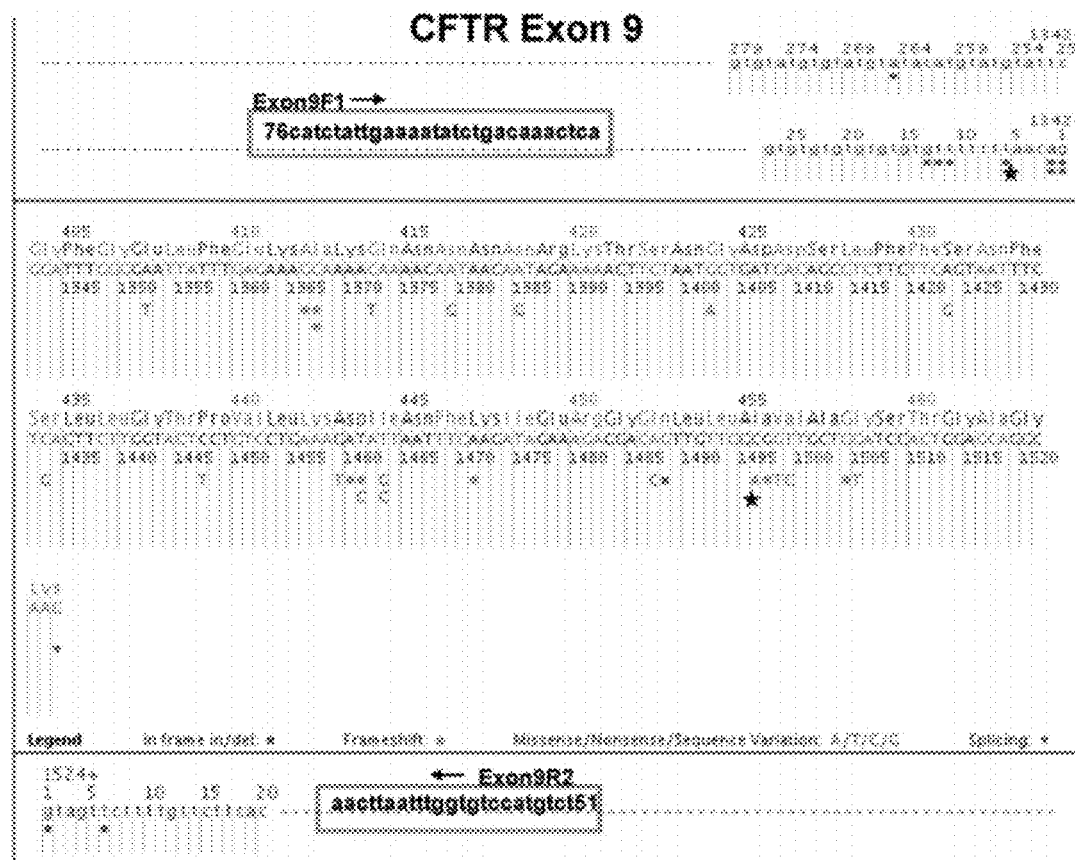
Figure 6K:
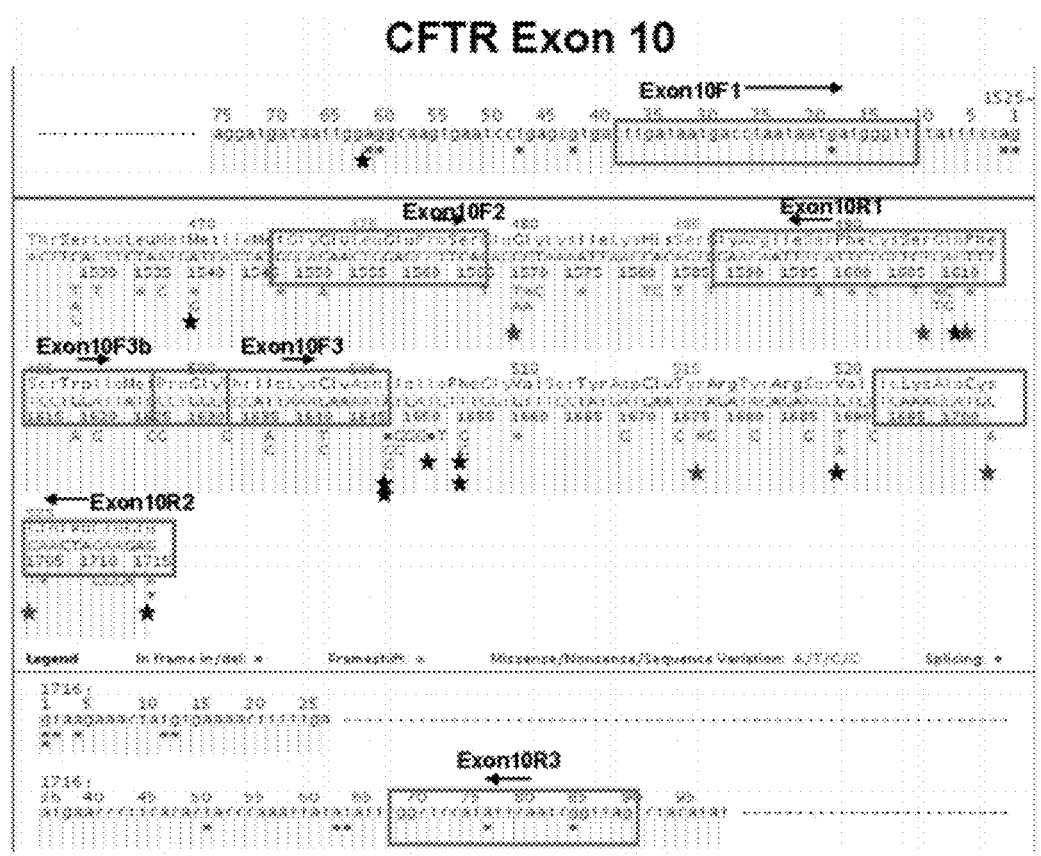
Figure 6L:
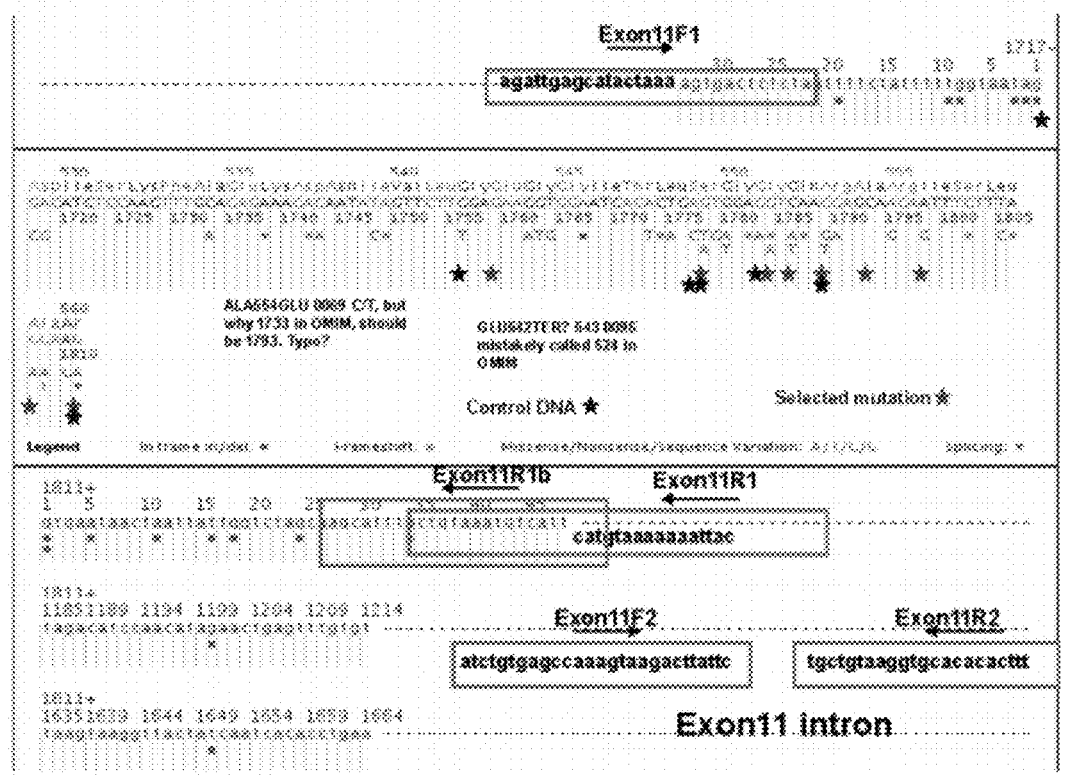
Figure 6M:
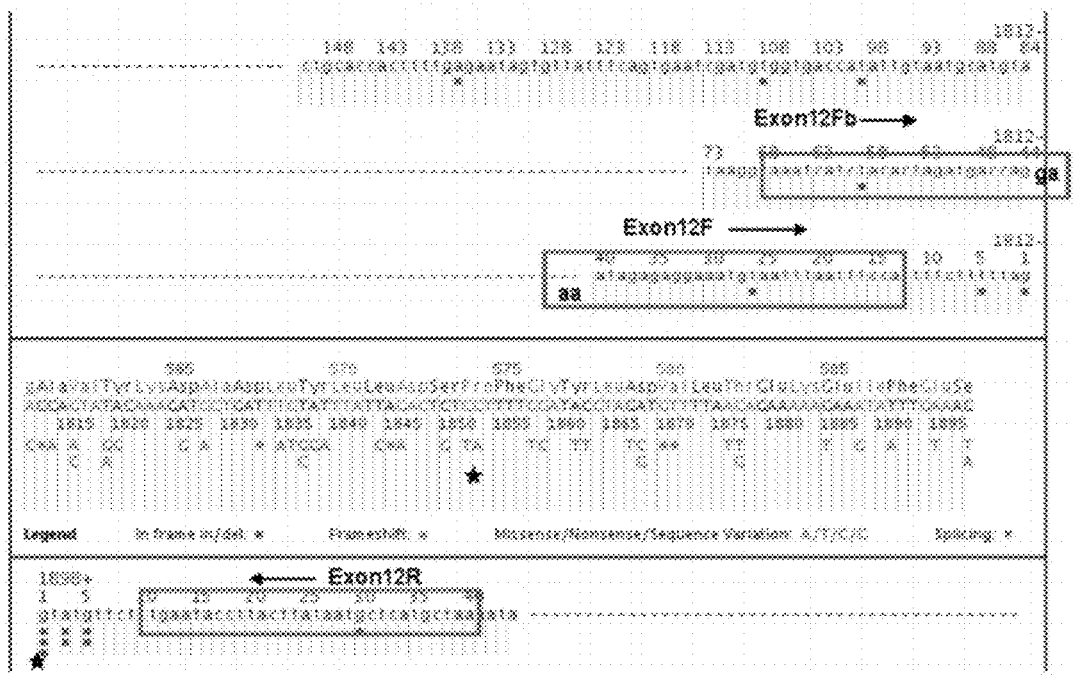
Figure 6N:
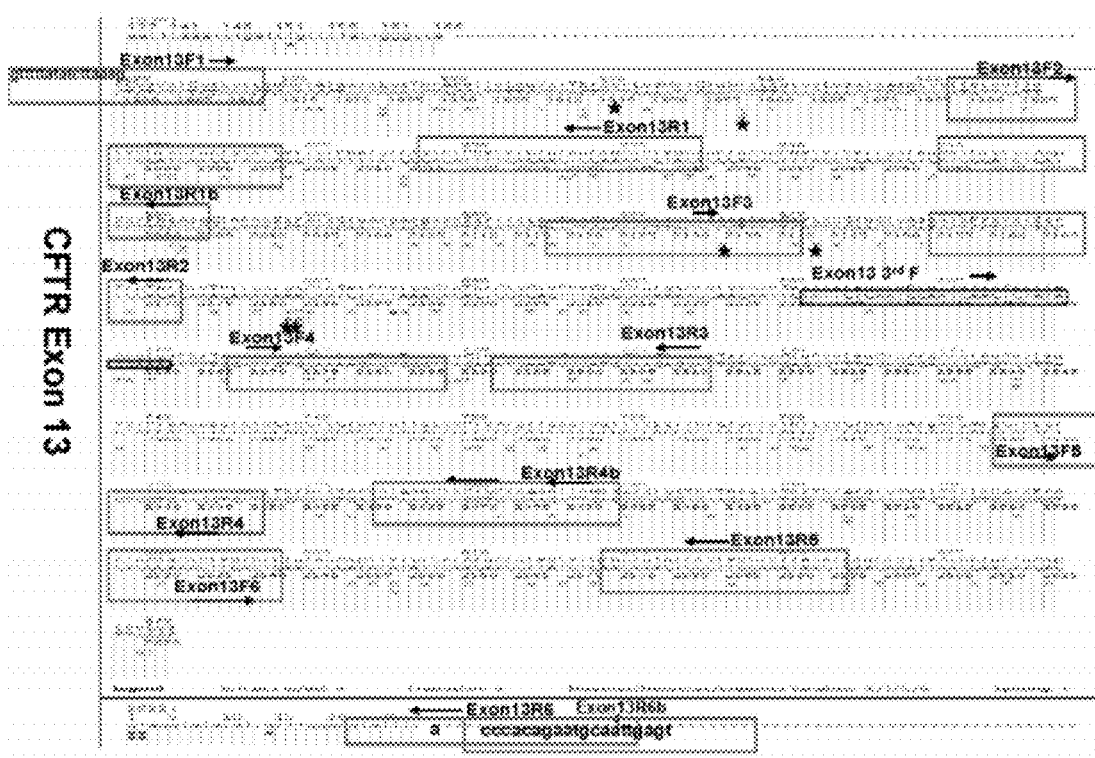
Figure 6O:
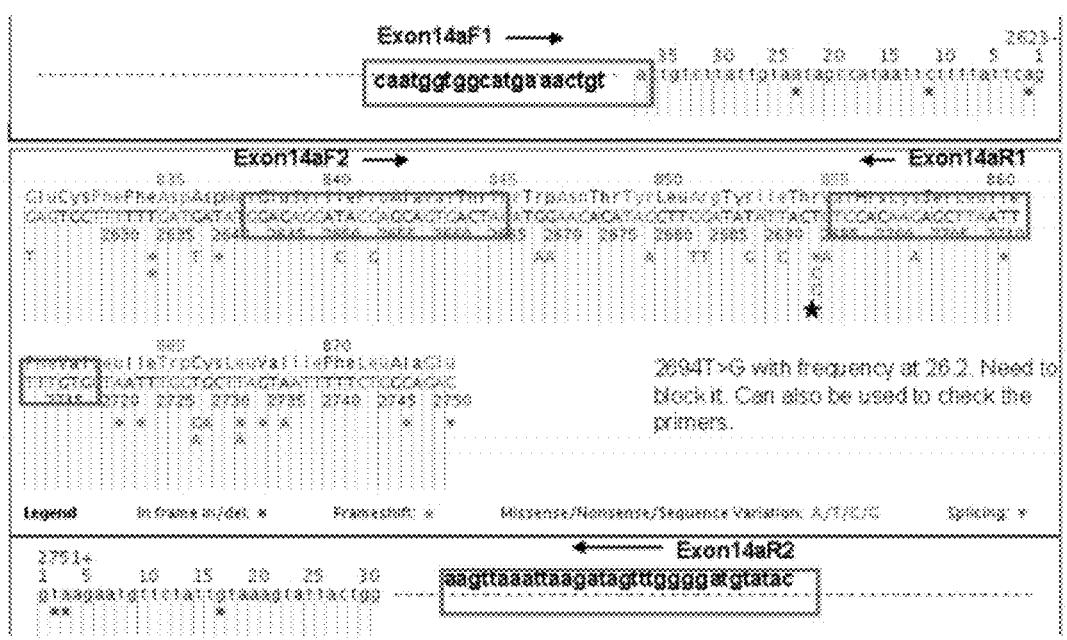
Figure 6P:
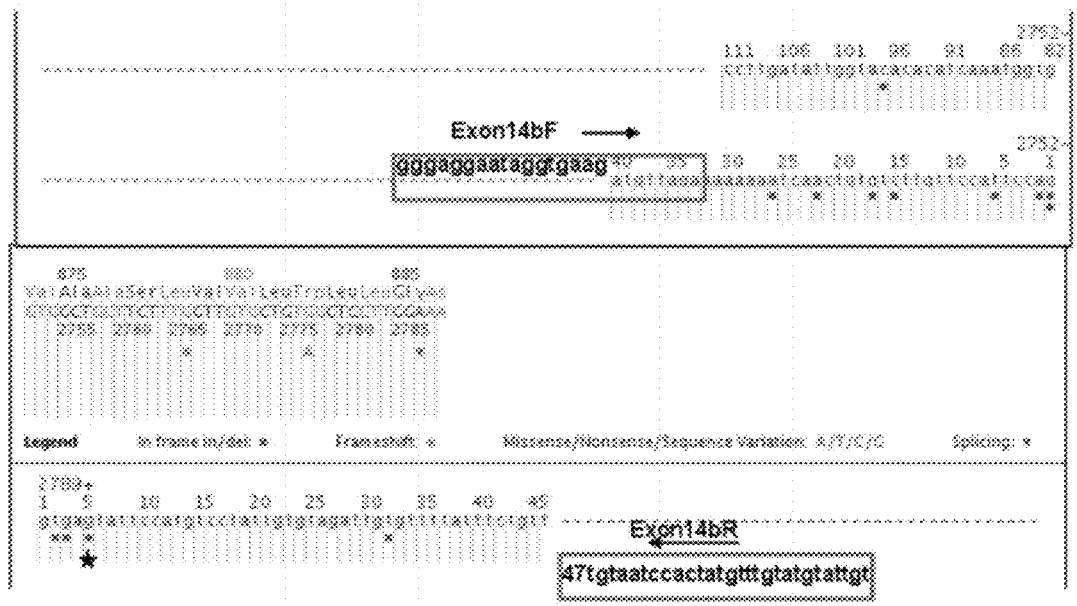
Figure 6Q:
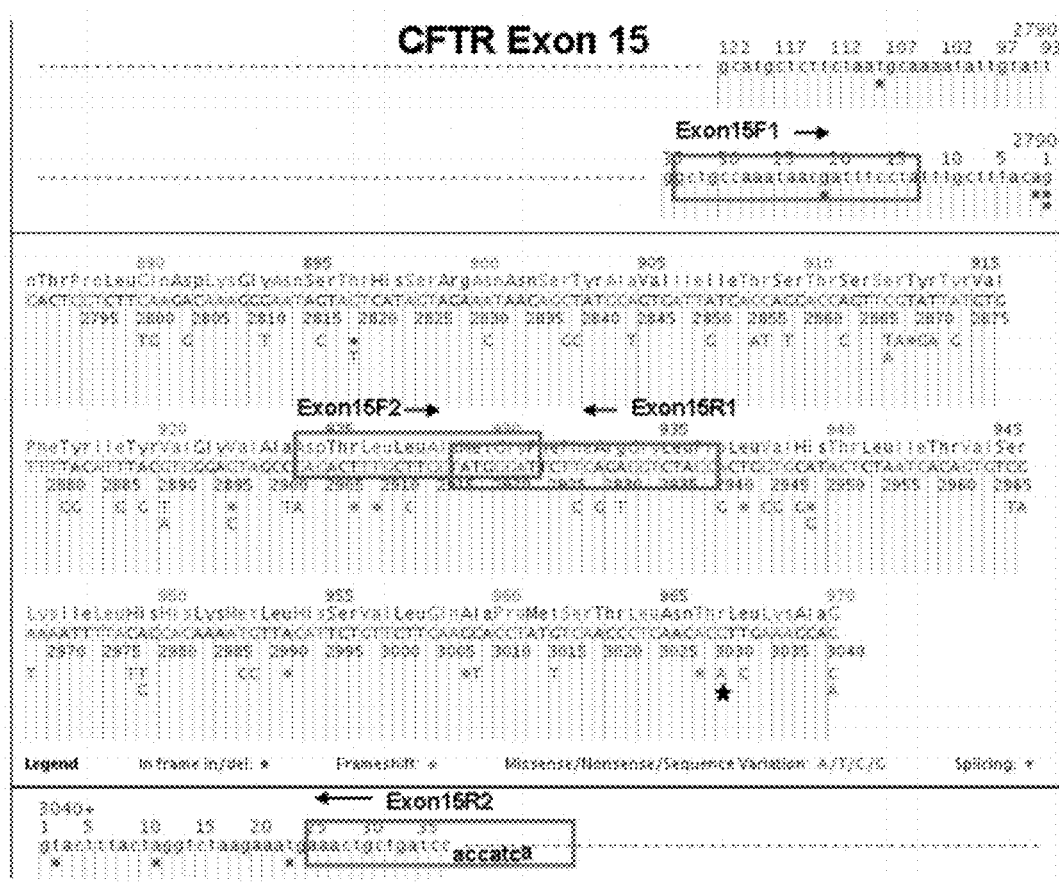
Figure 6R:
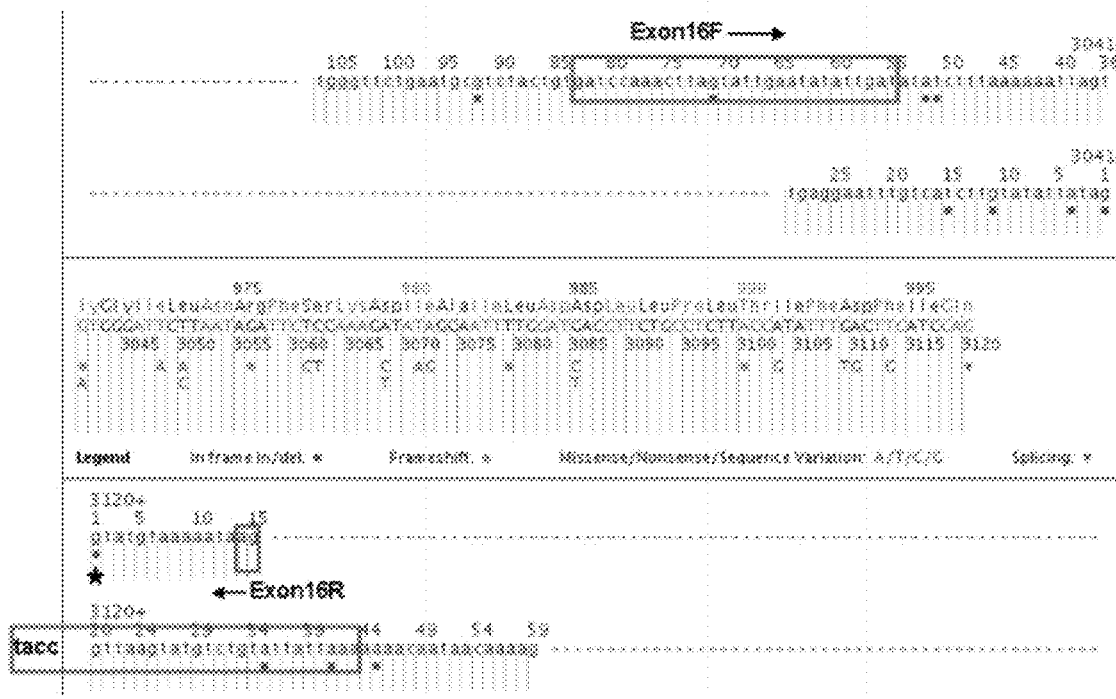
Figure 65:
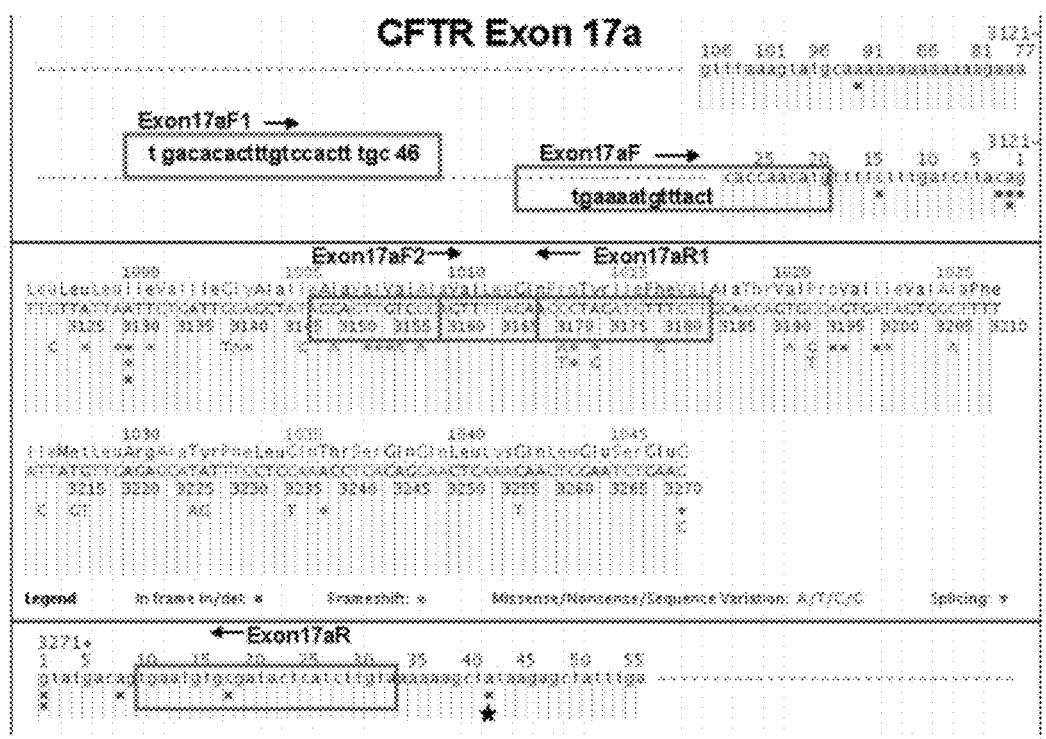
Figure 6T:
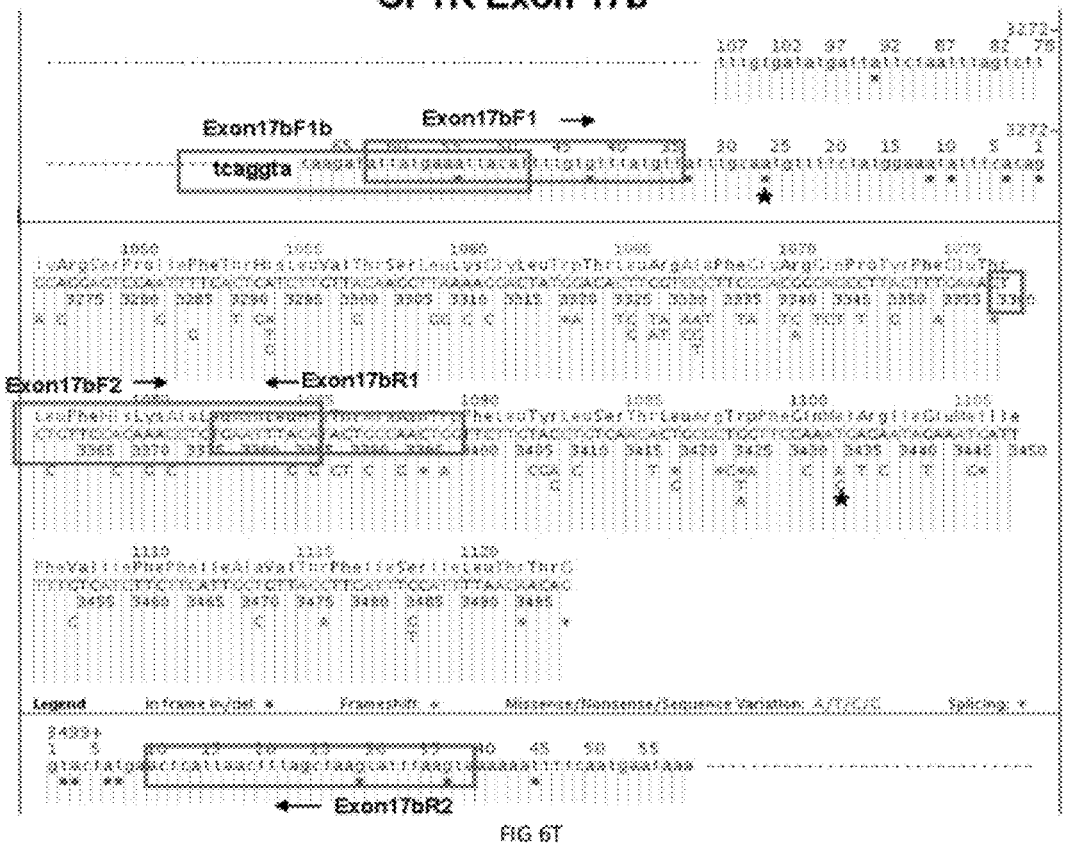
Figure 6U:
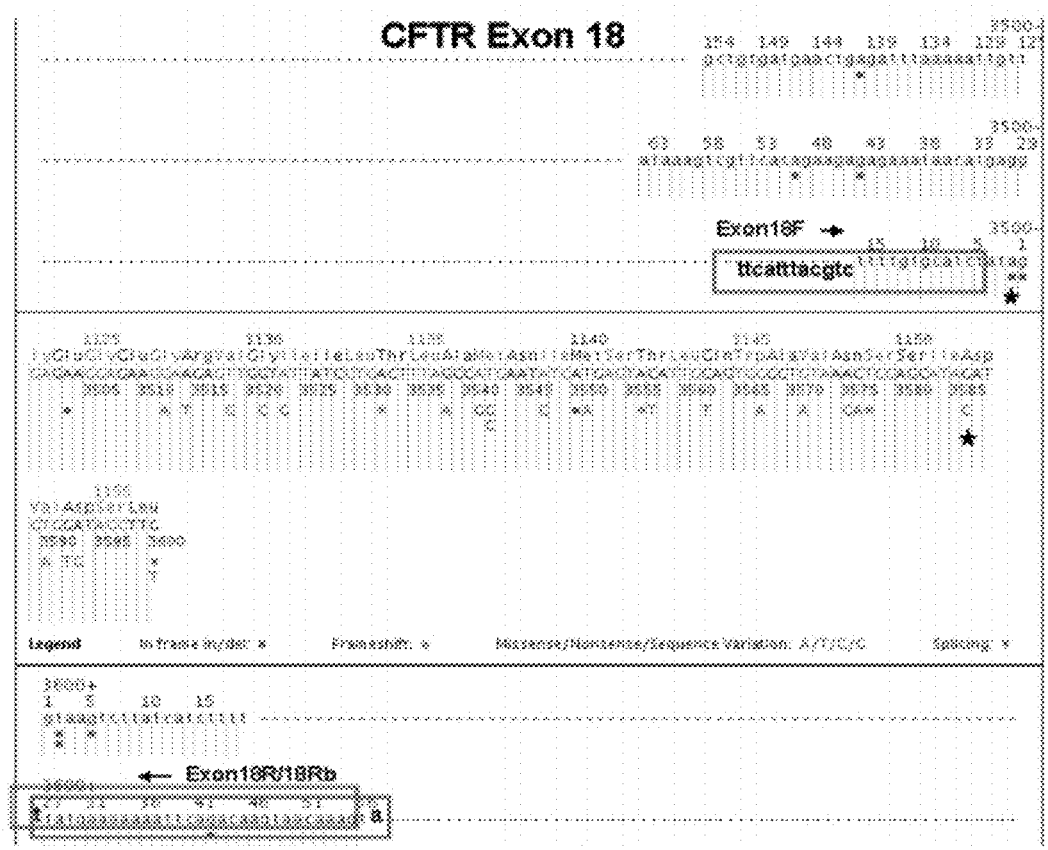
Figure 6V:
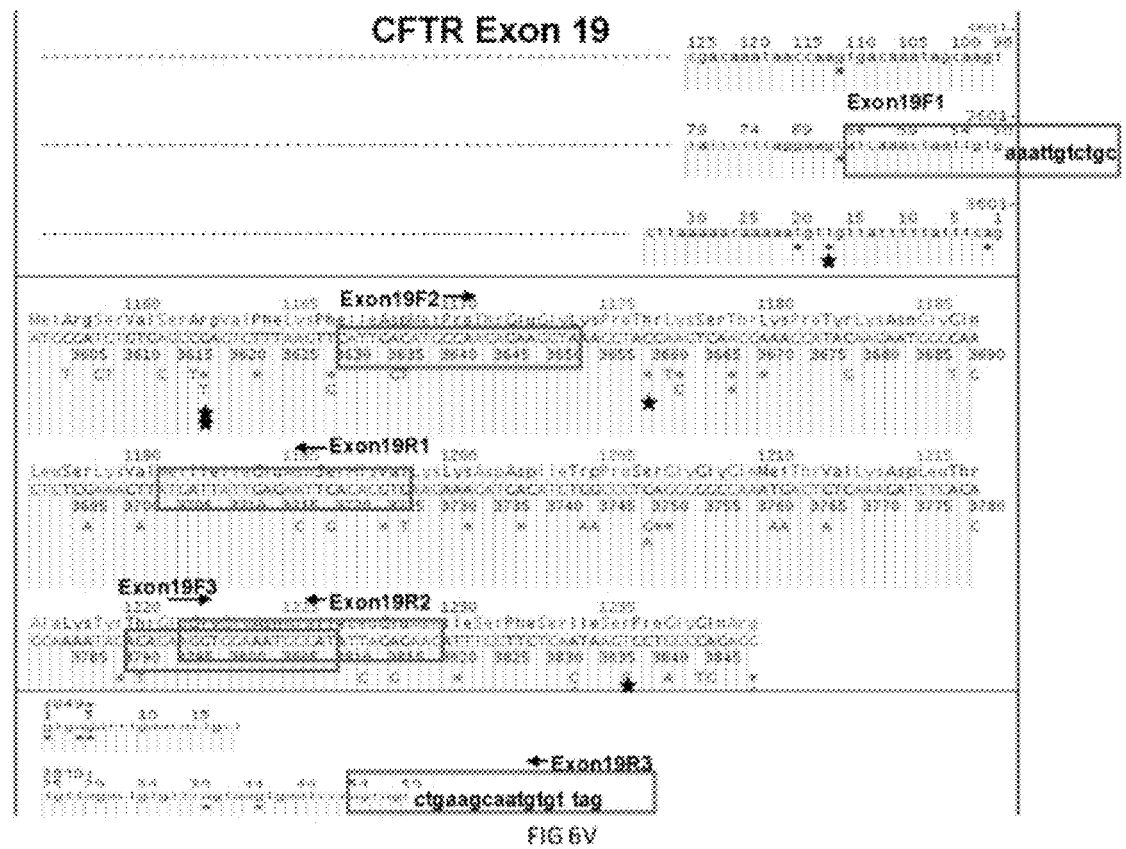
Figure 6W:
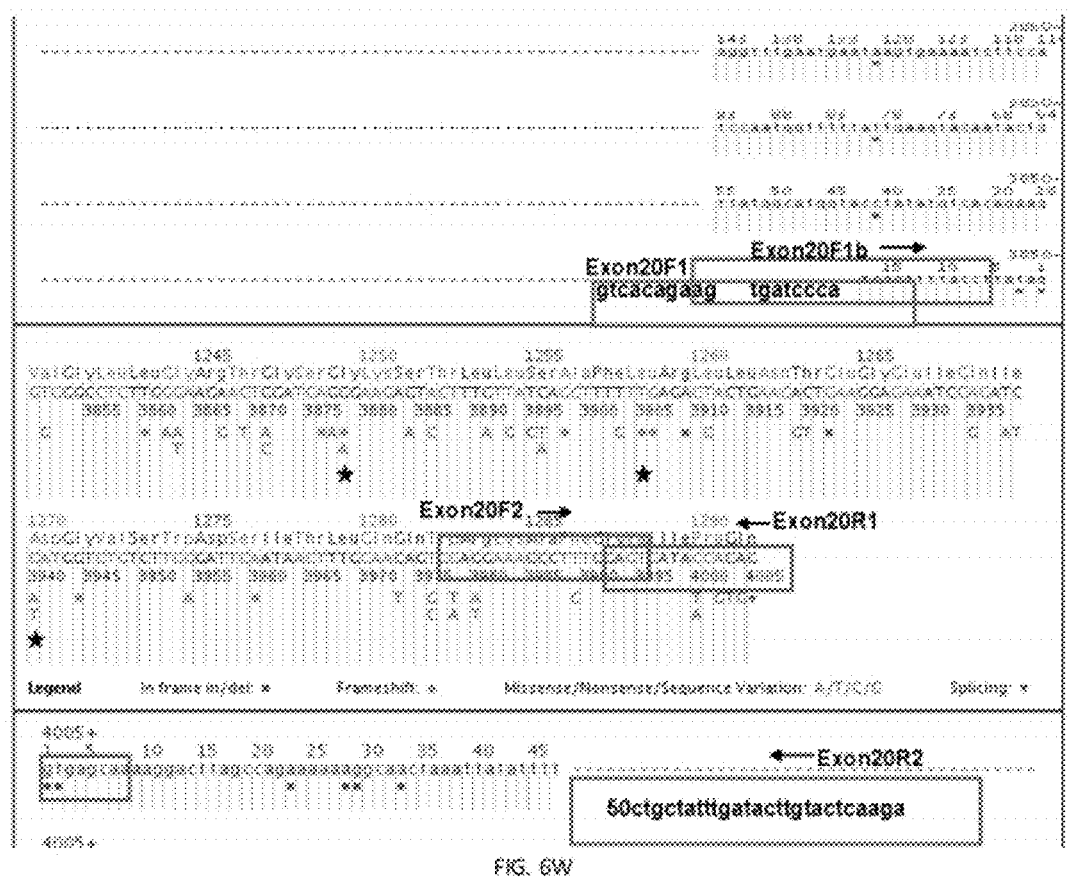
Figure 6X:
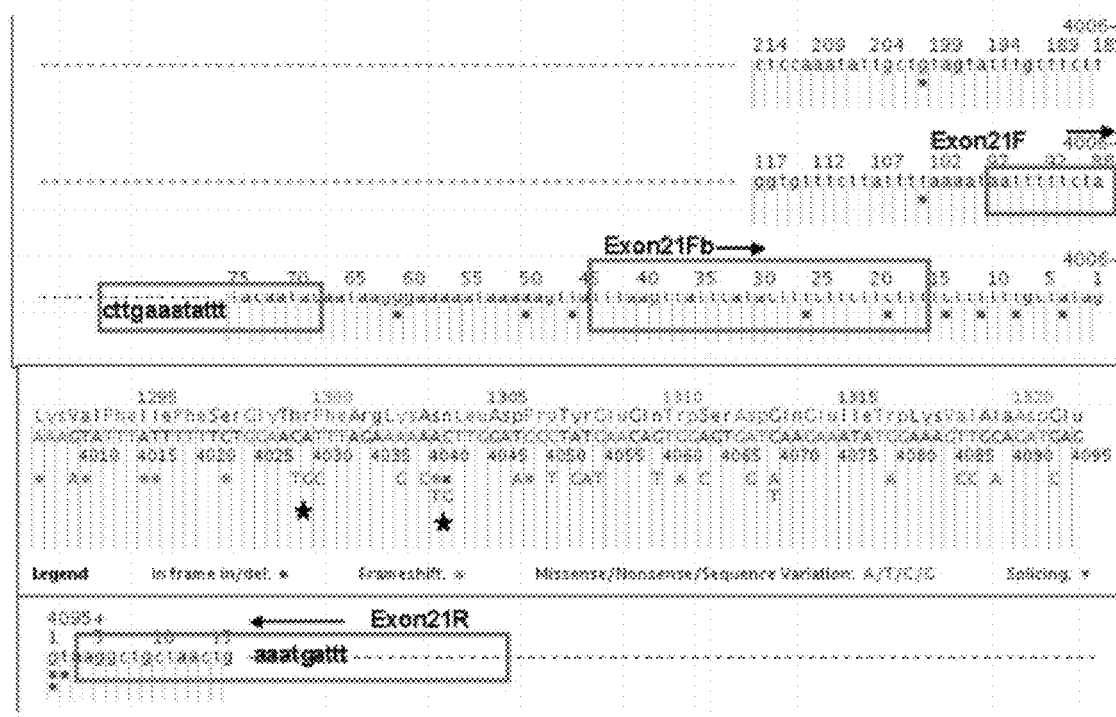
Figure 6Y:
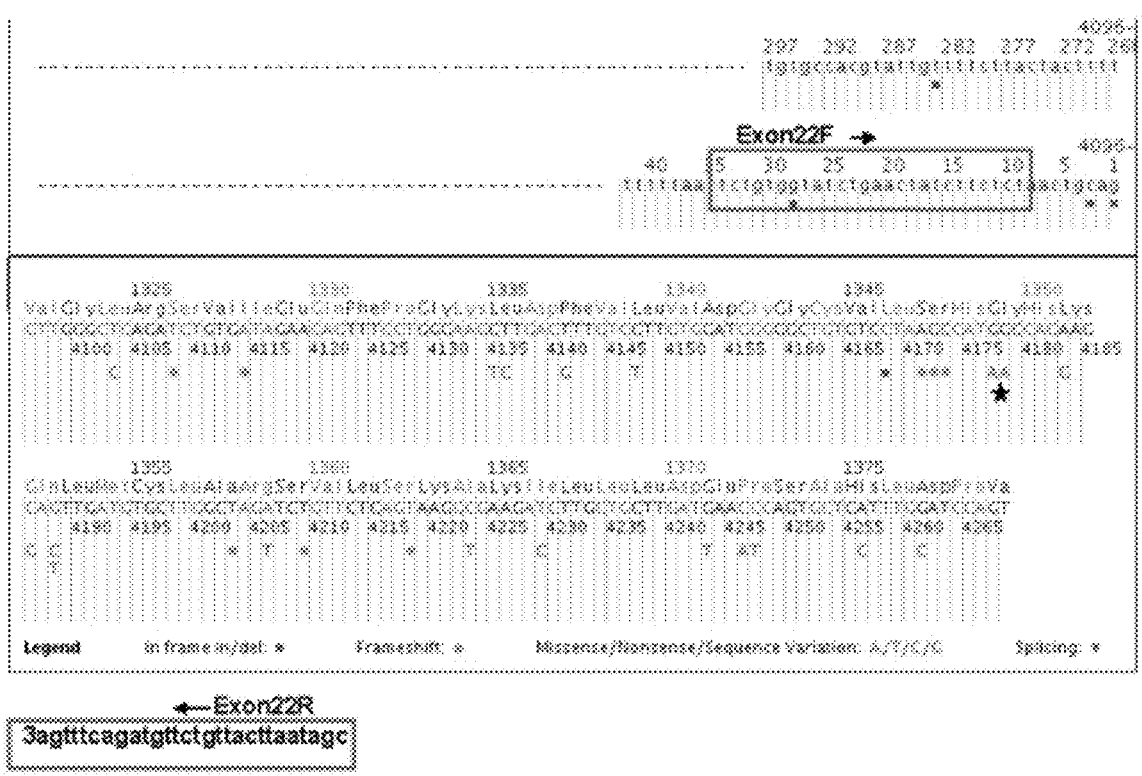
Figure 6Z:
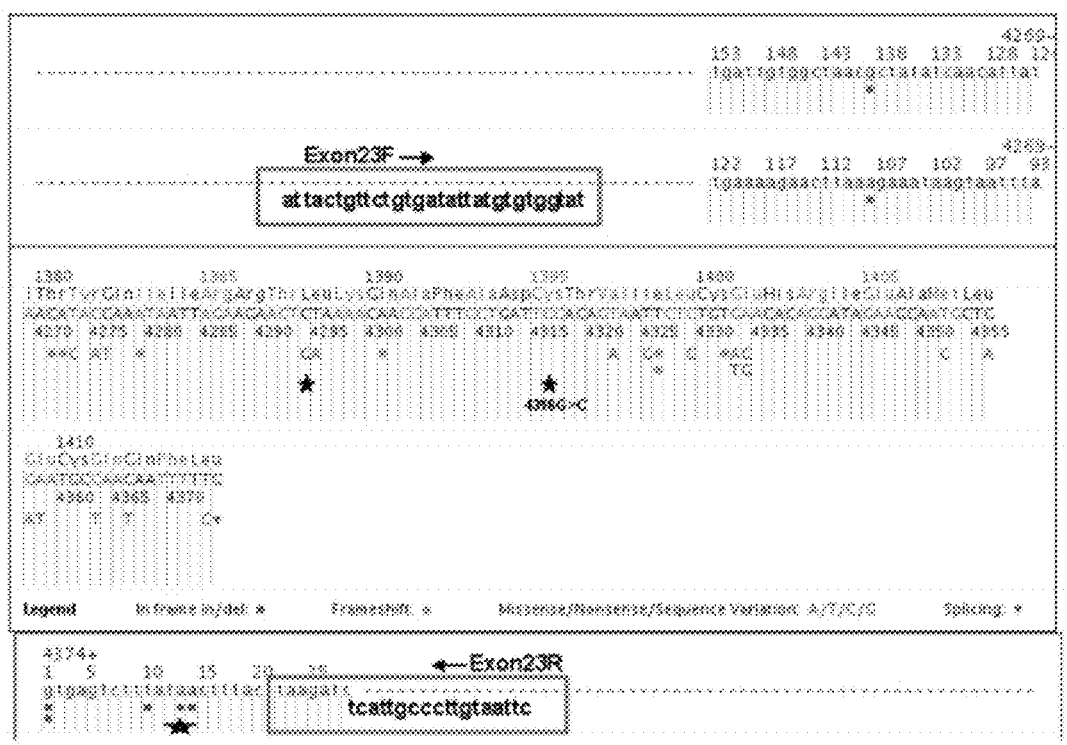
Figure 6A:
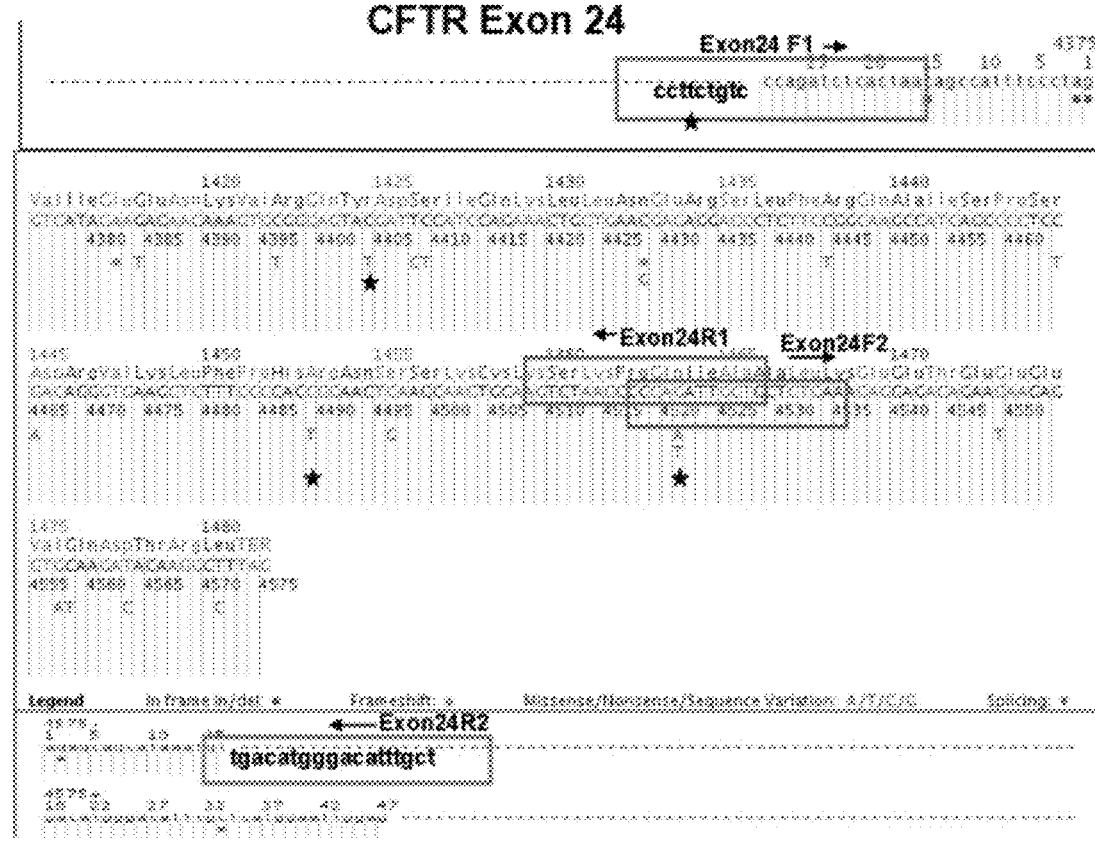
Figure 7A:
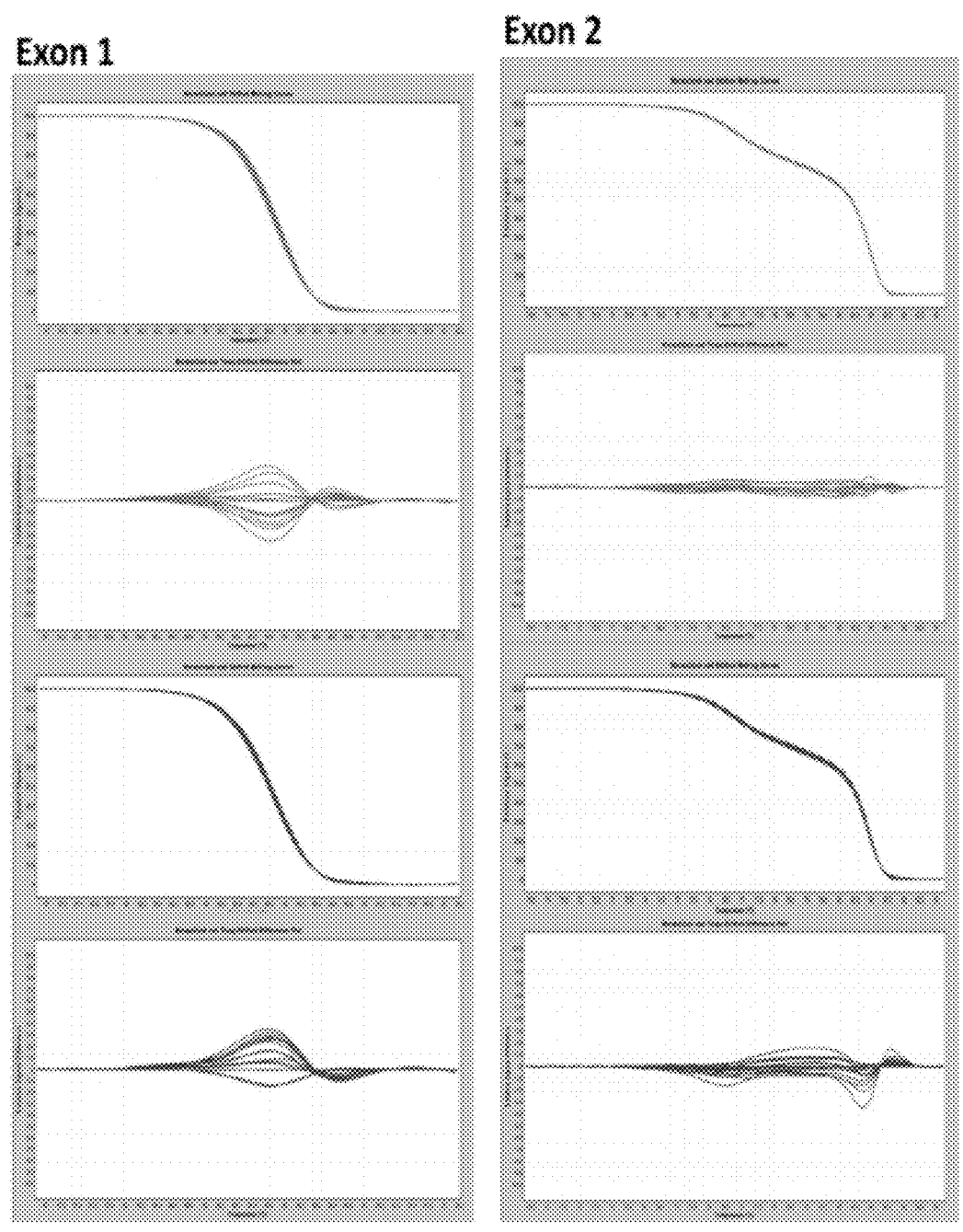
Figure 7B:
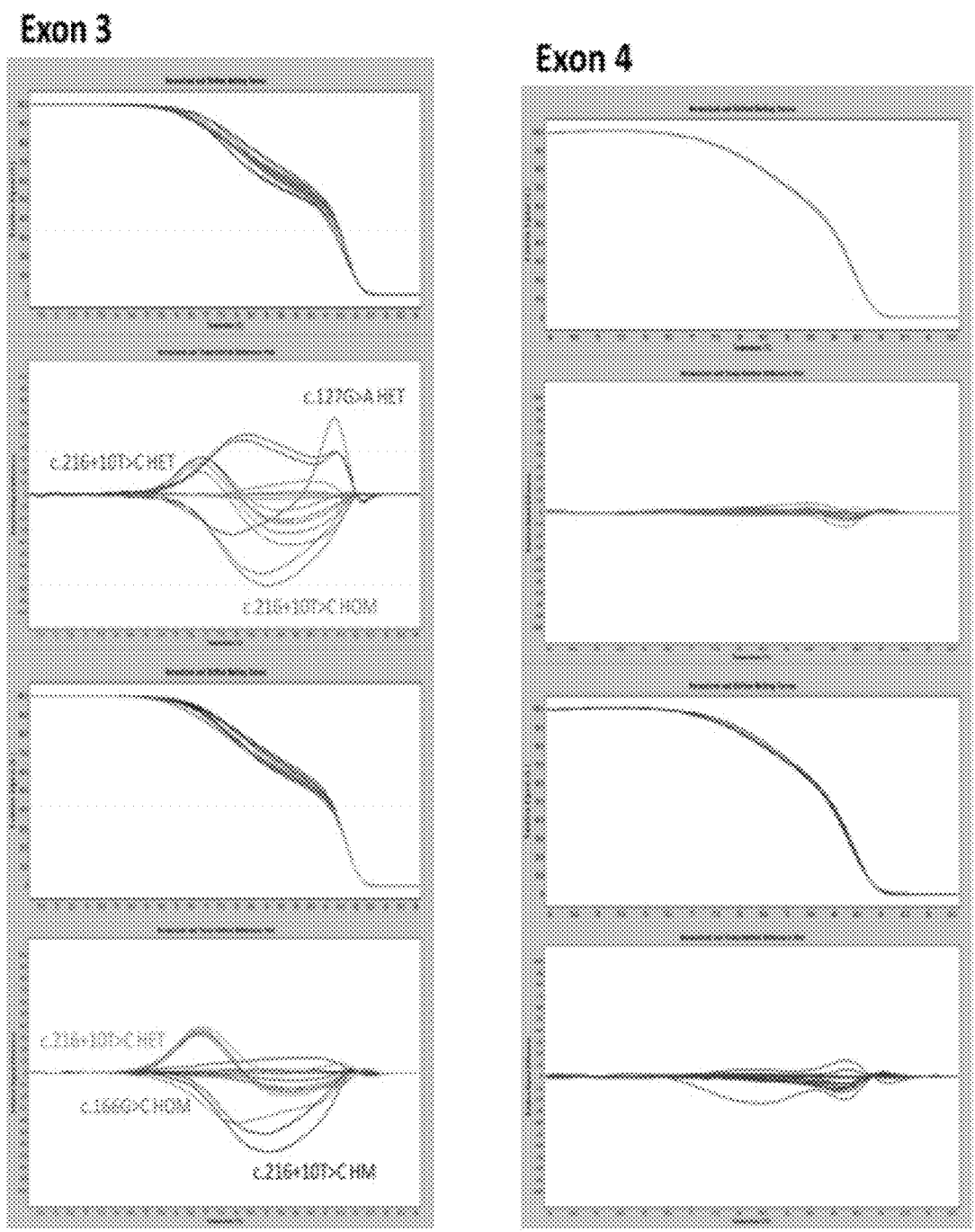
Figure 7D:
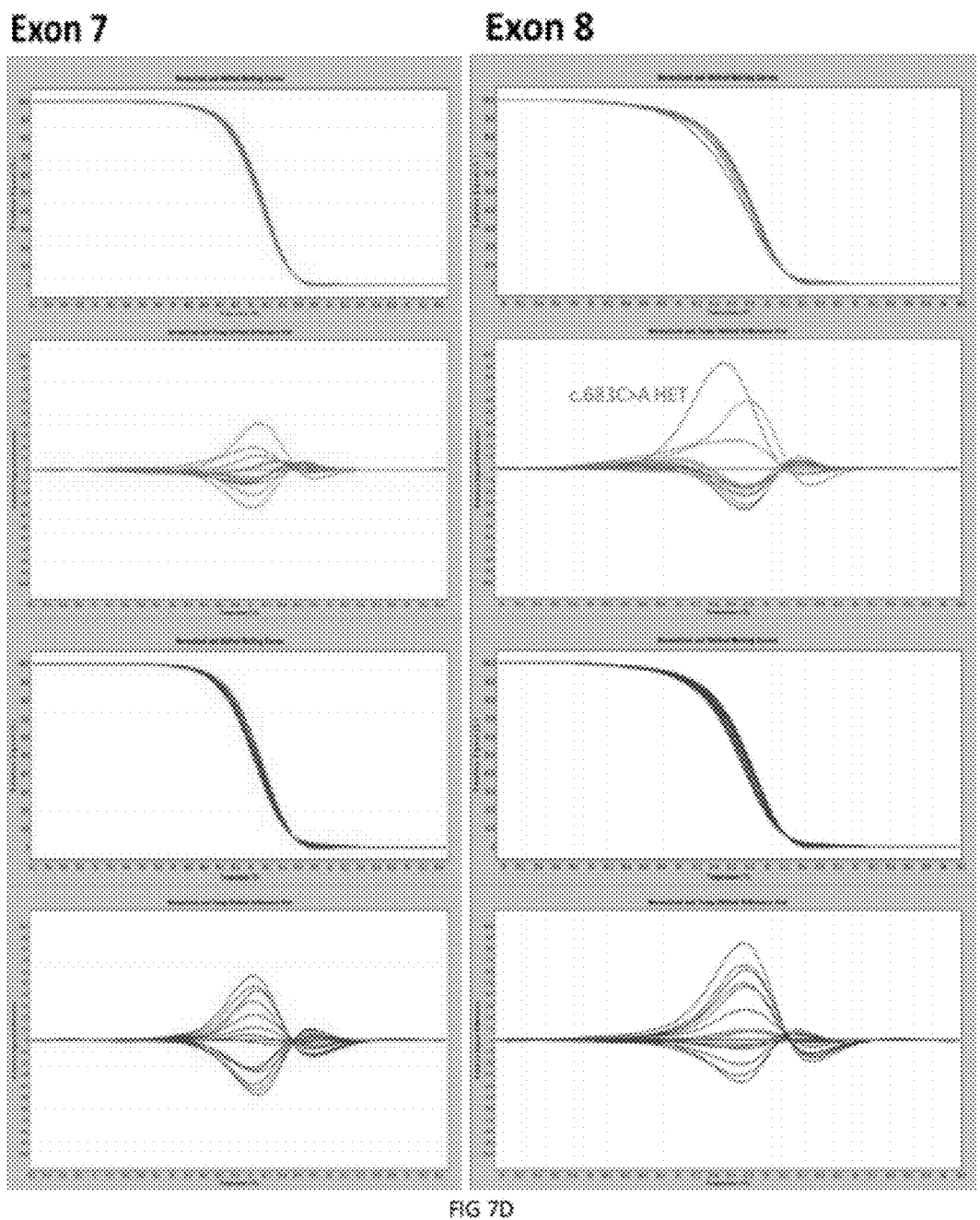
Figure 7G:
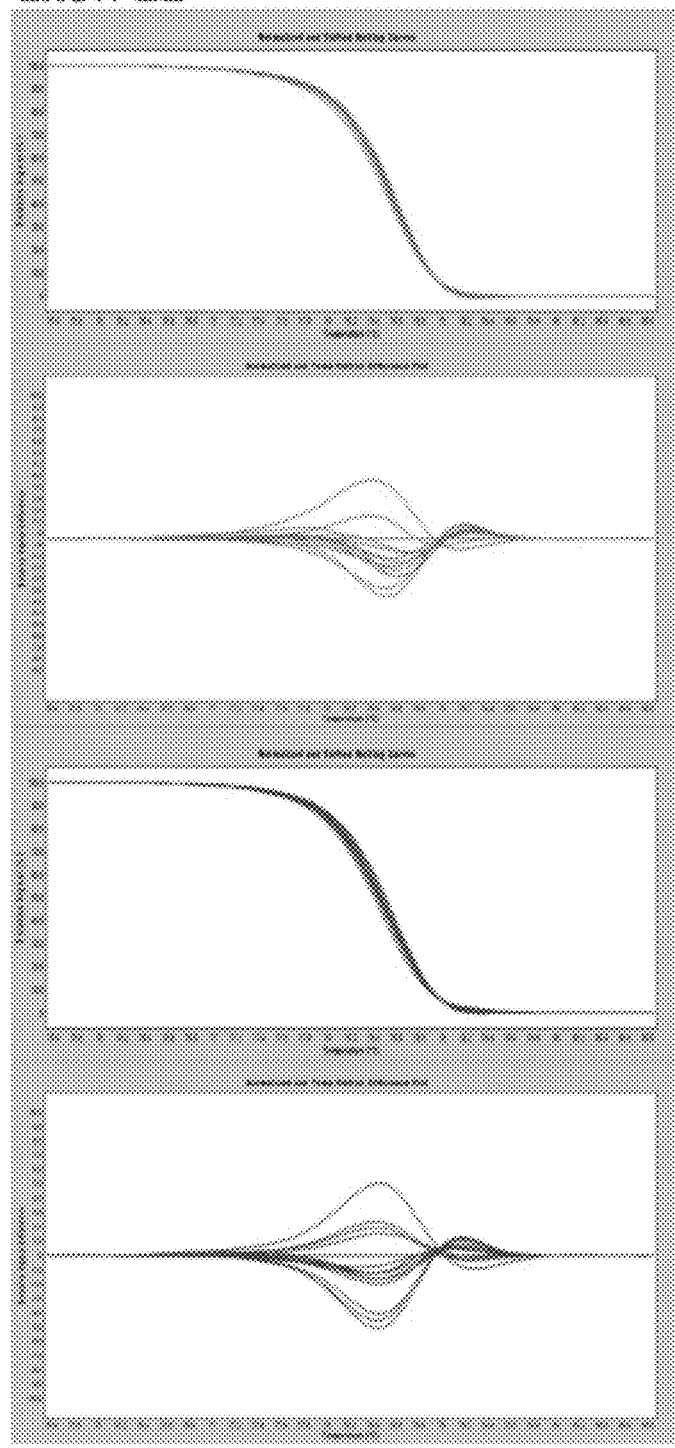

The CFTR gene resides on Chromosome 7 and contains 27 exons. Exon size ranges up to 800 bp. To maximize scanning sensitivity, primers were designed with amplicon size of less than 250 bp in most cases, so multiple primer sets were used to amplify some exons. A total 45 pairs of primers were needed to cover all the 27 CFTR exons and the intron-exon junctions (Table 1). All the designed primers were mapped to the CFTR mutation data base(FIG. 6A-6AA). Primers were ordered from Sigma.

TABLE 1

CFTR scanning primers
CFTR SCANNING PRIMERS

| EXONS/INTRONS | # PRIMERS NEEDED TO COVER EACH EXON |
|---|---|
| 1 | 1 |
| 2 | 1 |
| 3 | 2 |
| 4 | 2 |
| 5 | 1 |
| 6a | 2 |
| 6b | 1 |
| 7 | 2 |
| 8 | 1 |
| 9 | 1 |
| 10 | 3 |
| 11 | 1 |
| 12 | 1 |
| 13 | 6 |
| 14a | 2 |
| 14b | 1 |
| 15 | 2 |
| 16 | 1 |
| 17a | 1 |
| 17b | 2 |
| 18 | 1 |
| 19 | 3 |
| 20 | 2 |
| 21 | 1 |
| 22 | 1 |
| 23 | 1 |
| 24 | 2 |
| Total 27 | 45 |

Initial screening of all the designed primers were conducted by PCR and HRMA on the LightCycler480 using the conditions shown in Table 2:

TABLE 2a

Reagent Concentrations in Master mix

| | 20 uL | | | |
|---|---|---|---|---|
| Volume of Reaction | Stock | Units | Final | Vol add |
| 2X CULS Buffer | 2 | x | 1 | 10 |
| Forward Primer | 10 | uM | 1 | 2 |
| Reverse Primer | 10 | uM | 1 | 2 |
| LC Green Plus | 10 | x | 1 | 2 |
| H2O | | | | 1.264 |
| dNTPs (ThermoScientific) | 25 | mM | 0.37 | 0.296 |
| 3 mM MgCl2 | 250 | mM | 3 | 0.24 |
| Takara Taq Polymerase | 5 | U/uL | 1 | 0.2 |
| Total | | | | 18 |

TABLE 2b

LightCycler480 conditions

| 1 cycle | 95 C. | 10 sec |
|---|---|---|
| 40 cycles | 94 C. | 5 sec |
| | 58 C. | 5 sec |
| | 72 C. | 6 sec |
| 1 cycle | 94 C. | 5 sec |
| | 45 C. | 3 sec |
| Melt | 40 C. | 15 sec |
| | 95 C. | 10 acquisitions |

CULS 2× buffer comprised 2M Betaine, 100 mM Tris pH 8.0, 100 mM KCl, 0.02 mM EDTA, 0.08% Tween20, 4% DMSO. As described in table 2a, the CULS 2× buffer was diluted 1:2 in the final preparation.

For each reaction, gDNA was present as 2 µl of 50 ng/µl (100 ng final amount for a 20 µl reaction) or for plasmid DNA as 2 ul of 0.066 pg/µl (0.132 pg final amount for a 20 µl reaction).

Each set of primers was used to amplify genomic or plasmid DNA as described in Table 2b, and amplification curves were generated by plotting fluorescence as a function of the cycle number as shown in FIG. 2A-2H. Amplified products were subjected to HTRM as described in Table 2b, and flourescence was plotted as a function of temperature to generate the melting curves shown in FIG. 2A-2H.

Primer sets were evaluated for the presence of plateau amplification or aberrant amplification as shown in FIG. 3. 27 primer sets had the desired plateau amplification. 17 primer sets showed aberrant amplification. Primer sets with aberrant amplifications will be redesigned.

Five exons were selected (exons 3, 7, 10, 11 and 13) were subjected to a blinded study utilizing no template controls (NTC). The primer sets for the selected exons was used to amplify genomic or plasmid DNA as described above and in Table 2b, and amplification curves were generated by plotting fluorescence as a function of the cycle number as shown in FIG. 4A-4F. A flat NTC curve is visible in the amplification curves. Amplified products were subjected to HTRM as described in Table 2b, and fluorescence was plotted as a function of temperature to generate the melting curves shown in FIG. 4A-4F.

Once scanning primer designs are completed, primer sets will be designed for direct genotyping of pathogenic mutations known to occur in each Exon. For instance, primers will be designed for each of the 23 known CF mutations encompassed by the ACOG CF panel. Genotyping primers would be used as a reflexive testing if a positive scanning assay result was obtained on a patient.

Figure 5A:
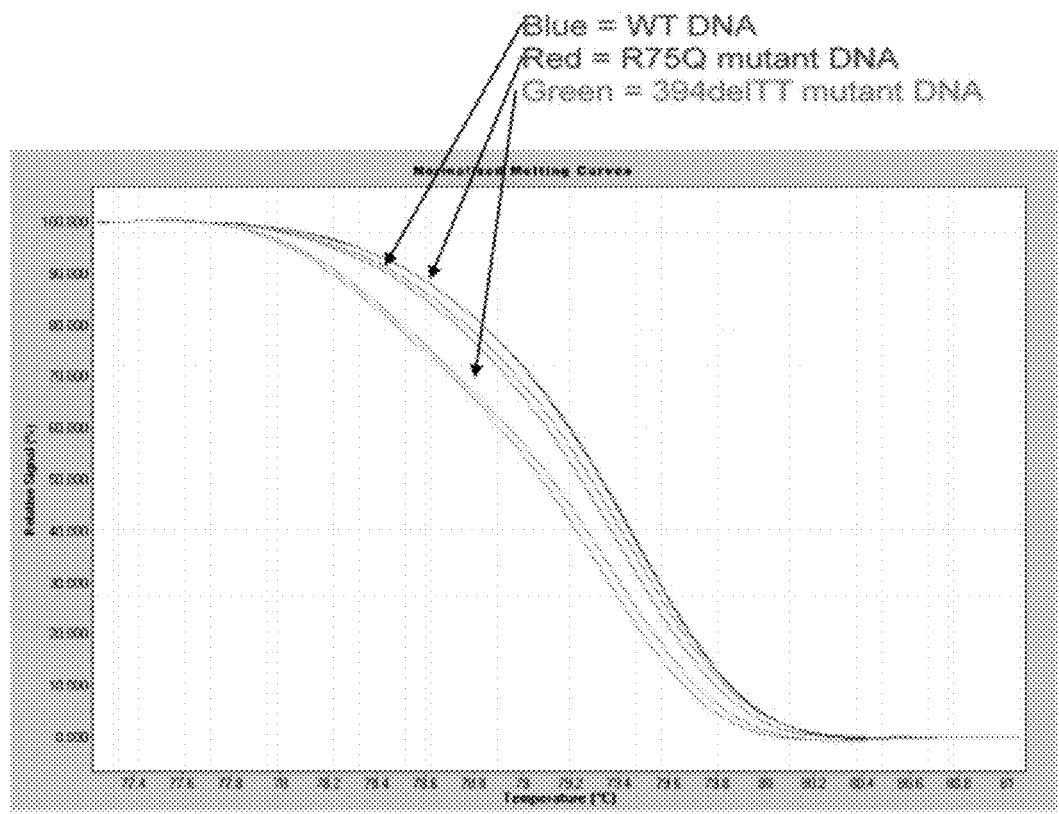
FIG. 5A is a sample melting curve (% Relative Signal vs. Temperature in ° C.) showing wildtype DNA and two mutant DNA samples.
Figure 5B:
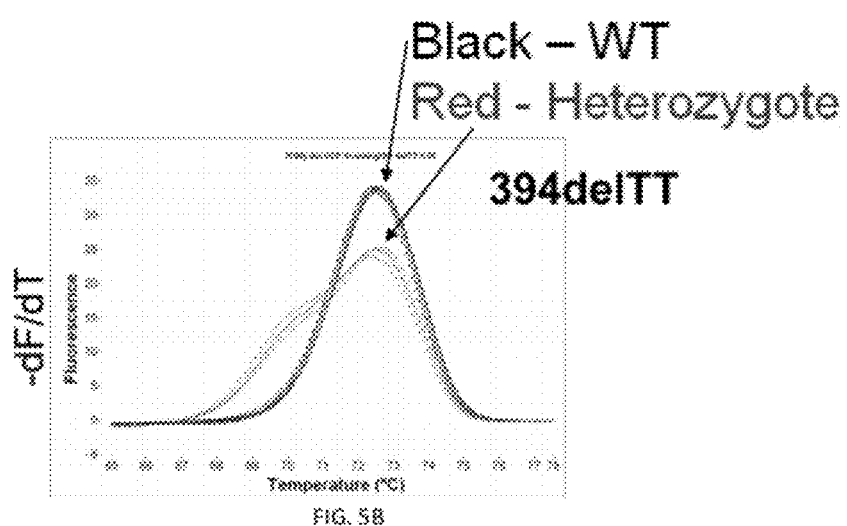
FIG. 5B is a differential plot (–dF/dT, Fluorescence v. Temperature in ° C.) showing the difference between a wildytpe and heterozygote DNA sample.

An example of the data to be obtained by using the genotyping primers is shown in FIG. 5A-5B, which depicts a normalized melting curve and the derivative plot which distinguishes between wildtype and heterozygous DNA for the tested mutation (394delTT).

2. Medium Chain Acyl-CoA Dehydrogenase Deficiency Screening

Materials and Methods:

A scanning panel for all 12 exons of the ACADM gene followed by small amplicon genotyping assays is presented for confirmation of two point mutations that have been associated with clinical disease. Scanning PCR primers used to amplify the 12 MCAD exons were derived from designs described by McKinney et al., (McKinney et al. 2004, Rapid, comprehensive screening of the human medium chain acyl-CoA dehydrogenase gene; *Molecular Genetics and Metabolism.* 82:112-120) and in-house designs from ARUP and Canon U.S. Life Sciences, Inc. laboratories (Table 3). Confirmation of known clinically relevant mutations was performed by reflex testing using small amplicon assays. Assays were designed for the most common pathogenic mutation (c.985A>G) and one suspected mild mutation (c.199T>C) that has been detected through newborn screening. In addition, small amplicon assays for two common variants (c.216+10T>C and c.1161A>G) were used (Table 3).

PCR and HRMA were performed using the LightScanner® 32 System with conditions shown in Table 4. Scanning assays for all 12 exons along with 4 genotyping assays were tested against 14 samples from ARUP Laboratories and 15 samples from the Coriell Institute for Medical Research, for a total of 29 clinical specimens (Table 5). Genomic DNA from the 14 ARUP samples was whole genome amplified (WGA) using the Qiagen REPLI-g® Mini kit for 2.5 µl template DNA to ensure enough DNA was available for replicate analysis. Samples from Coriell were not whole genome amplified. All samples were run twice with each assay (13 Scanning, 4 Genotyping), and one no template control was used for each run.

Sequence confirmation was performed on representative samples within a HRMA cluster or pattern to validate the result if previous sequence verification on the source DNA had not been performed.

TABLE 3

Primer designs (SEQ ID NOS 1-34, respectively, in order of appearance) for scanning and genotyping assays:

| Assay | F Primer Sequence | R Primer Sequence | Amplicon Length |
|---|---|---|---|
| *Exon 1 | GACCCGTGTATTATTGTCCGAG | TGCTCCGACACCACAATACC | 131 |
| *Exon 2 | CAGTAGTCTCTTATCTGATTAATGTTTAACTTATCAAATT | AAAGCTTCATATGTATAAGTTTAAAGTCAAAAGATAGAAC | 205 |
| *Exon 3 | CCTTGTTATCCAGTTTTAACTTTTCTAAATAATTTTC | CAGATAGTTTGATTACATAATCTTGTAAAAAATGT | 212 |
| *Exon 4 | CATTTTTTACAAGATTATGTAATCAAACTATCTGGATTTCAA | GAGTTCCACAATTTTTCTTACTCATATGCATTCCAG | 205 |
| *Exon 5 | ATAGTTTACCTTTATTTCTATTGTGATGTACTACATATT | TTCAGGAGTAACTATCTCATTAACAAGAGC | 233 |
| **Exon 6 | GCATCTCTGAATTTACATATCCAAT | AAGTGTGAAATAAAGCGGCA | 181 |
| #Exon 7 | CATTTAATTTCATTTCTCTTGTTTTTA | AGAAAAAATATACAAAGATGTTTTGA | 203 |
| *Exon 8 | GAGCAATCACCATGTGTTAT | AATGTTTTTATTAAAGGAAAGTTAAGTAATTT | 258 |
| *Exon 9 | TGATCCCTGTTTTAGGTAATTGC | GAGAAACACACTGAACATACAATTTT | 342 |
| *Exon 10 | ATAGACACTTAGGCAGATATTGTG | AAATTGATTAGTTTGTGGTTTAAAAATCAT | 264 |
| #Exon 11_1 | ACTTTTAAGTTTTCTCAATAAATATCCTTTAAT | TATCTCCAGCAAATGCCTTT | 198 |
| #Exon 11_2 | GTCGAAATACCTATTATGCTTCT | ATATTCTCTCTCCTTGCAAAC | 197 |
| #Exon 12 | AAAGATATTTAACCTACACTTATATTTTTC | ACAGTGGCTTGTGTTCT | 154 |
| **c.199T > C | GAAATCATCCCAGTGGCT | ACCTACTTCACCAGTTTTATCA | 48 |
| **c.216 + 10T > C | ATGATAAAACTGGTGAAGTAGGTA | AAAGATTTTTCCCTCTTTAAAATGT | 52 |
| **c.985A > G | CTGGCTGAAATGGCAATG | CTCTGGTAACTCATTCTAGC | 50 |
| **c.1161A > G | GGCAATGGATTTAATACAGA | GCATCCCTCATTAGTTTTTC | 50 |

*designed by ARUP laboratories,
**designed by Canon U.S. Life Sciences, Inc., and
derived from McKinney et al. 2004.

TABLE 4

PCR and HRM Conditions; a) Reagent concentrations in the master mix, b) PCR Protocol, c) HRM Protocol.

a) Master Mix

| Reagent | Concentration |
| --- | --- |
| dNTPs | 0.37 mM |
| $Mg^{2+}$ | 3 mM |
| F Primer | 1 μM |
| R Primer | 1 μM |
| LCGreen ® Plus+ | 1 X |
| Taq Polymerase | 0.05 U/μL |
| Template DNA | 50 ng per reaction |
| BAS | 250 μg/mL | b) PCR Protocol

| Hot Start | 95° C. | 2 min |
| --- | --- | --- |
| Denaturation | 95° C. | 5 sec |
| Annealing | 58° C. | 10 sec |
| Extension | 72° C. | 15 sec |
| Post-PCR | 95° C. | 10 sec |
| | 45° C. | 10 sec |

The denaturation/annealing/extension cycle is performed 35 times for scanning assays, and 40 times for genotyping assays.
Table 4c) HRM Protocol
"High-res melt" Data Collection
65° C. → 95° C. at 0.3° C./second

TABLE 5

DNA from the Coriell Institute for Medical Research.

NA01954
NA07523
NA08684
NA11319
NA14439
NA14448
NA14501
NA17137
NA09820
NA07441
NA07552
NA08338
NA11282
NA11284
NA11254

Results

Scanning assay results produced expected patterns for HRMA in all 29 specimens tested demonstrating the ability of the assay to detect variants in all exons tested. Results were presented as difference plots and were grouped according to DNA source used for the assay, WGA or genomic (FIG. 7A-7G). Samples used as difference plot baselines were chosen for each assay from those that fell in the middle of the normal cluster pattern. Scan results for genomic DNA samples and those amplified by WGA are shown separately since these two sample types will display different normal patterns, though variants are easily distinguishable from the normal population in most cases. Known benign variants in Exons 1, 2, 4, 7, 12 that were located in the primer binding region or outside of it showed no differences as expected.

Variants were detected in all other exons. In exons where both WGA and genomic samples contained the same variant, the variant was easily identified in both sample types (FIG. 7, exons 3, 5, 11). Variants that were represented in only a single sample type were also distinguishable from the normal population with two exceptions. The amplified region of exon 9 appears to contain three melt domains which did not generate reproducible melt patterns, and the heterozygous samples can fall within the cluster of normal population sequences (FIG. 7, exon 9). A similar case was observed with the first amplified domain of exon 11 (FIG. 7, exon 11_1). These two amplification targets would need to be redesigned to assure that a consistent difference in pattern could be detected. Variation in amplification of normal sequences created a different pattern on replicate assay runs in exon 7 (FIG. 8). While the overall difference plots appeared dissimilar, the extent of overall difference (10 units) remained the same. This occurred only in this exon and no difference in assay buffer or conditions were identified to explain this.

Figure 9A:
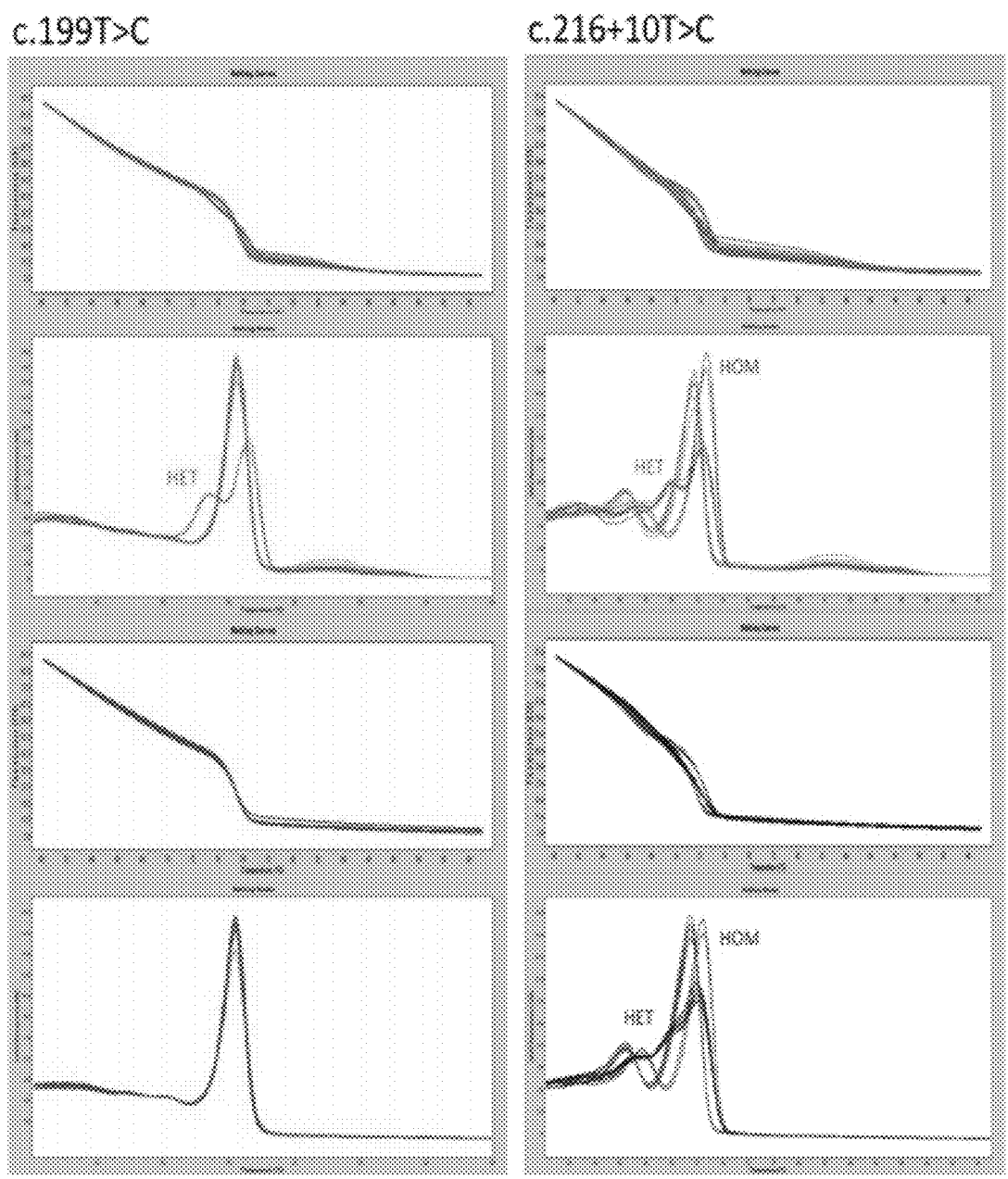
FIG. 9 are images of the small amplicon genotyping assays for four targets: c.199T>C, c.216+10T>C, c.985A>G, and c.1161A>G. Melt curves and melt derivatives are shown for whole genome amplified samples and genomic DNA samples separately for each assay. Whole genome amplified samples that appear normal in any given assay are colored light green; genomic DNA samples that appear normal in any given assay are colored dark green. All other variants are labeled with a matching color in the relevant plot. The c.216+10T>C assay has an additional melt feature at a lower Tm for all DNAs. A smaller product was seen on a gel run with these PCR products in addition to the expected product, which may explain this extra feature. This assay is currently being redesigned. From top to bottom, the four plots for each assay are: Melting Curves—Whole Genome Amplifed samples (Fluorescence vs. Temperature in ° C.); Melting Peaks—Whole Genome Amplified samples (–(d/dT) Fluorescence vs. Temperature in ° C.); Melting Curves—genomic DNA samples (Fluorescence vs. Temperature in ° C.); and, Melting Peaks—genomic DNA samples (–(d/dT) Fluorescence vs. Temperature in ° C.).
Figure 9B:
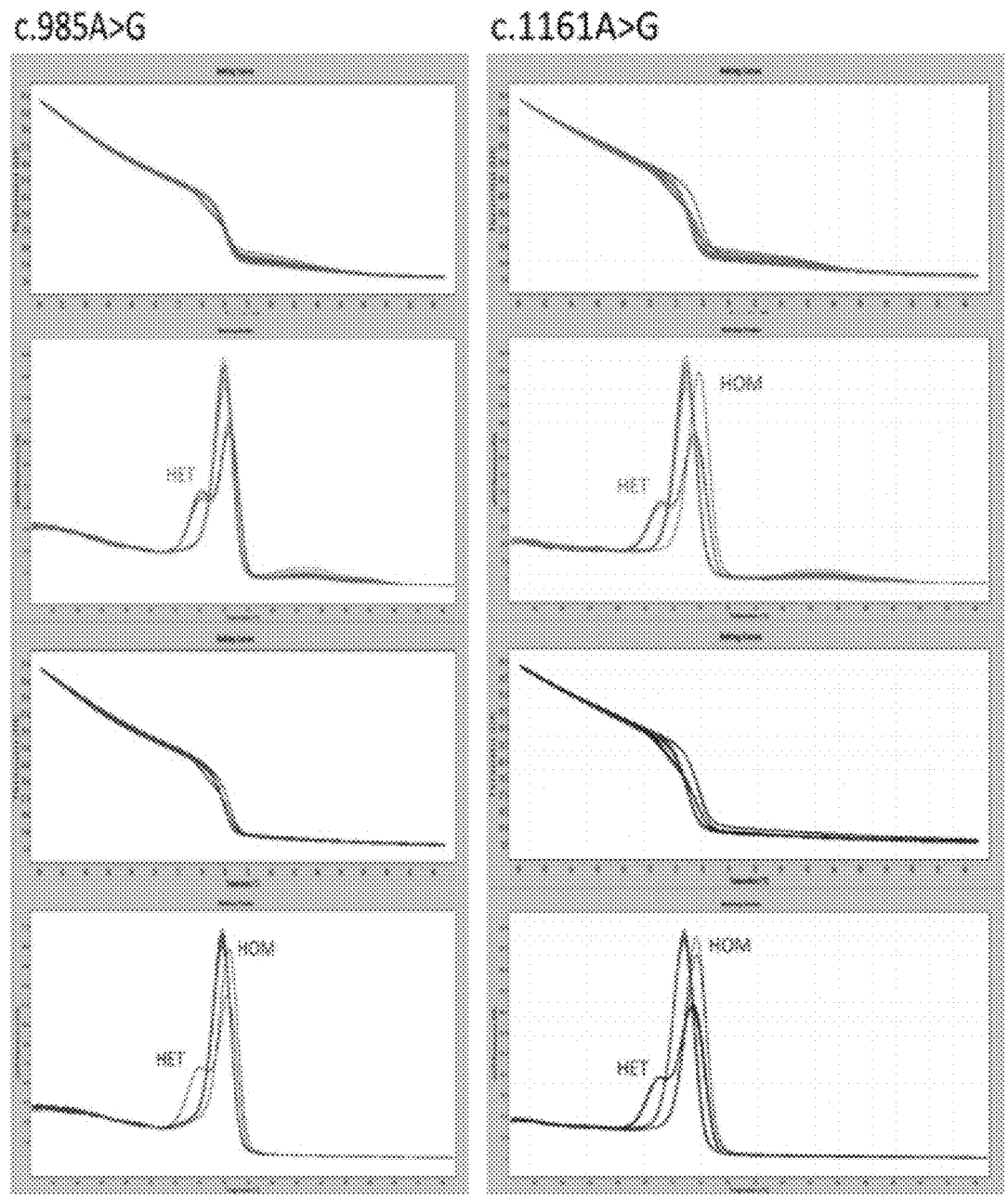

Samples with variants identified in the scanning of exons 3 and 11 were reflex tested by small amplicon genotyping to distinguish if the variants were clinically relevant (FIG. 9). Samples without variants were included in the assay for reference. All samples were correctly identified by reflex testing.

CONCLUSIONS

It has been demonstrated that gene scanning using HRMA is an effective rapid method for identifying variants in the ACADM gene. Thorough testing of amplification target is essential to be able to establish reliable patterns for the observed variation in the normal population and to demonstrate that variants can be distinguished. Use of WGA DNA can be invaluable during assay development since it shows similar ability in performance to genomic DNA at distinguishing variants from the normal population. Identification of baseline sequences that produce consistent patterns and defining the normal spread of difference across normal sequences are crucial to validation of HRMA scanning methods. Sequence confirmation of mutation scanning can take several days to move through testing and data review procedures. Rapid turnaround of confirmation testing by HRMA genotyping assays from positive screening results for errors of inborn metabolism such as MCAD would allow for early dietary intervention. Using genotyping to distinguish between common variants and clinically relevant mutations by HRMA rather than by sequencing allows the entire test cycle to be completed within a single laboratory shift.

Having thus described in detail preferred embodiments of the present invention, it is to be understood that the invention defined by the appended claims is not to be limited to particular details set forth in the above description, as many apparent variations thereof are possible without departing from the spirit or scope of the present invention. Modifications and variations of the method and apparatuses described herein will be obvious to those skilled in the art, and are intended to be encompassed by the following claims.

What is claimed is:

1. A method of sequentially analyzing a biological sample for the presence of a disease causing mutation comprising the steps of:
   (a) obtaining the biological sample and amplifying at least one exon of a gene of interest in the biological sample;
   (b) finding at least one exon having a mutation by screening each amplified exon of the gene of interest in the biological sample for the presence of a mutation to find each exon having a mutation without genotyping the mutation;
   (c) for the at least one exon having a mutation found in step (b), subjecting to amplification in a separate amplification reaction each location containing a particular mutation within the at least one exon having a mutation by using primers specific to the particular mutation, each separately amplified section being shorter than the exon; and
   (d) separately screening each amplified section within each exon found in step (b) for each particular mutation occurring in that specific exon to genotype the mutation identified in step (b).

2. The method of claim 1, wherein the screening performed in steps (b) and (d) utilizes high resolution melt analysis including comparing results of the high resolution melt analysis of each amplified exon and each of the at least one exon section with a control, wherein deviation from the control is indicative of a mutation.

3. The method of claim 1, wherein the method is performed in a microfluidic device.

4. The method of claim 1, wherein a positive test for a mutation according to step (b) is indicative of a presence of the mutation.

5. The method of claim 4, wherein a carrier or disease state caused by the mutation is cystic fibrosis or medium chain acyl-CoA dehydrogenase deficiency.

6. The method of claim 4, wherein the positive test according to step (b) indicating the presence of a mutation is confirmed by genotyping prior to the cessation of further testing.

7. A method of sequentially analyzing a biological sample for the presence of a disease causing mutation or a common variant comprising the steps of:
   (a) obtaining the biological sample and amplifying at least one exon of a gene of interest in the biological sample;
   (b) finding at least one exon having a mutation by screening each amplified exon in the biological sample for the presence of a mutation or variant to identify each exon having the mutation or variant without genotyping the mutation or variant;
   (c) for the at least one exon having a mutation found in step (b), subjecting to amplification in a separate amplification reaction each location containing a particular mutation within the at least one exon having a mutation by using primers specific to the mutation or variant, each amplified section being shorter than the exon; and
   (d) screening each amplified section within each exon identified in step (b) for each particular mutation or variant to occur in that specific exon to genotype the mutation or variation identified in step (b).

8. A method of analyzing a biological sample for the presence of a genetic mutation in a gene of interest comprising the steps of:
   (a) selecting one or more primers to amplify an exon of the gene of interest and amplifying the exon;
   (b) finding at least one exon having a mutation by performing a thermal melt analysis on the amplified exon by generating melting curves for the entire amplified exon and determining whether the thermal melt analysis results indicate the presence of a mutation or common variant in the amplified exon without genotyping of the mutation or common variant;
   (c) if the determination of step (b) is indicative of the presence of a mutation in the amplified exon, then
      (1) selecting one or more primers to amplify each portion of the at least one exon from step (b) including the site of one or more mutations or common variants;

(2) subjecting to amplification each of the at least one portions of the exon using the primers from step (1) in a separate amplification reaction, each of the at least one separately amplified portions being shorter than the exon;

(3) performing a thermal melt analysis on the amplification products of step (2);

(d) based upon the thermal melt analysis results of step (3) genotyping the mutation or common variant;

(e) repeating steps (a) through (b) for each exon in the gene of interest, until each exon has been amplified and subjected to thermal melt analysis.

9. The method of claim 8, wherein the step (b) of determining whether thermal melt analysis results indicate the presence of a mutation in the amplified exon comprises comparing the thermal melt analysis results for the amplified exon with known thermal melt results for wildtype DNA of the amplified region.

10. The method of claim 8, wherein the step (b) determining whether thermal melt analysis results indicate the presence of a mutation in the amplified exon comprises comparing the thermal melt analysis results for the amplified exon with known thermal melt results for DNA of the amplified region comprising a homozygous or heterozygous mutation.

11. The method of claim 8, wherein the presence of a mutation is indicative of a disease or carrier state.

12. The method of claim 11, wherein the disease or carrier state caused by the mutation is cystic fibrosis or medium chain acyl-CoA dehydrogenase deficiency.

13. A method of sequentially analyzing a biological sample for the presence of a disease causing mutation comprising the steps of:

(a) obtaining the biological sample and amplifying each exon of a gene of interest in the biological sample;

(b) finding at least one exon having a mutation by screening an amplified exon of the gene of interest in the biological sample for the presence of a mutation without genotyping the mutation by generating melting curves for the entire amplified exon;

(c) for the at least one exon having a mutation found in step (b), subjecting to amplification in a separate amplification reaction each location containing a particular mutation within the at least one exon having a mutation by using primers specific to the mutation, each amplified section being shorter than the exon;

(d) separately screening each amplified section of the exon found in step (b) to have the mutation for each particular mutation that occurs in that specific section of the exon in order to genotype the mutation found in step (b); and (e) optionally repeating steps (b) and (c) for more than one exon.

14. The method of claim 13, wherein the method occurs in a microfluidic device.

* * * * *